(12) United States Patent
Amano et al.

(10) Patent No.: US 11,504,747 B2
(45) Date of Patent: Nov. 22, 2022

(54) DRUG SORTING DEVICE, SORTING CONTAINER, AND DRUG RETURN METHOD

(71) Applicant: YUYAMA MFG. CO., LTD., Osaka (JP)

(72) Inventors: Hirokazu Amano, Osaka (JP); Tomohiro Sugimoto, Osaka (JP); Yasuyuki Yoshikawa, Osaka (JP); Maki Matsunaga, Osaka (JP); Koji Ito, Osaka (JP); Yuta Higuchi, Osaka (JP)

(73) Assignee: YUYAMA MFG. CO., LTD., Osaka (JP)

( * ) Notice: Subject to any disclaimer, the term of this patent is extended or adjusted under 35 U.S.C. 154(b) by 375 days.

(21) Appl. No.: 16/604,617

(22) PCT Filed: Apr. 12, 2018

(86) PCT No.: PCT/JP2018/015338
§ 371 (c)(1),
(2) Date: Oct. 11, 2019

(87) PCT Pub. No.: WO2018/190394
PCT Pub. Date: Oct. 18, 2018

(65) Prior Publication Data
US 2020/0156120 A1 May 21, 2020

(30) Foreign Application Priority Data

Apr. 14, 2017 (JP) .............................. JP2017-080623
Mar. 15, 2018 (JP) .............................. JP2018-048554

(51) Int. Cl.
*A61J 1/03* (2006.01)
*B07C 5/342* (2006.01)
(Continued)

(52) U.S. Cl.
CPC ............... *B07C 5/3422* (2013.01); *A61J 1/03* (2013.01); *A61J 3/00* (2013.01); *B07C 5/362* (2013.01); *A61J 2205/40* (2013.01)

(58) Field of Classification Search
CPC . A61J 2205/40; A61J 1/03; A61J 3/00; B07C 5/3422; B07C 5/362; G16H 20/13
See application file for complete search history.

(56) References Cited

U.S. PATENT DOCUMENTS 5,522,512 A 6/1996 Archer et al.
6,688,037 B2 * 2/2004 Keller .................... A01C 7/042
414/737
(Continued)

FOREIGN PATENT DOCUMENTS

JP      H10160554 A      6/1998
JP      10246702 A  *    9/1998
(Continued)

OTHER PUBLICATIONS

Notice of Reasons for Refusal issued in Japanese Application No. 201914665 dated Jan. 28, 2020 (5 pages) along with English translation (7 pages), for a total of 12 pages.
(Continued)

*Primary Examiner* — Patrick H Mackey
(74) *Attorney, Agent, or Firm* — Robert P. Michal, Esq.; Carter, DeLuca & Farrell LLP

(57) ABSTRACT

A medicine sorting device includes: a discrimination part for discriminating a type of a medicine based on an image captured by a first camera; and a conveyance/sorting unit for sorting, by each type, a plurality of types of medicines accommodated in a mixed state in a first accommodating part based on a discrimination result of the discrimination part, and storing the medicines in a second accommodating part.

20 Claims, 39 Drawing Sheets

(51) Int. Cl.
  *A61J 3/00* (2006.01)
  *B07C 5/36* (2006.01)

(56) References Cited

U.S. PATENT DOCUMENTS

| | | | | |
|---|---|---|---|---|
| 7,417,203 | B2* | 8/2008 | Lofquist | B07C 5/365 |
| | | | | 209/44.2 |
| 10,565,545 | B2* | 2/2020 | Yonaha | G16H 20/10 |
| 10,872,688 | B2* | 12/2020 | Swarvar | A61J 7/0076 |
| 11,065,180 | B2* | 7/2021 | Grosfils | G01N 21/31 |
| 11,136,223 | B2* | 10/2021 | Sato | B07C 5/368 |
| 2008/0051935 | A1 | 2/2008 | Handfield et al. | |
| 2011/0060448 | A1 | 3/2011 | Gotou et al. | |
| 2012/0293623 | A1* | 11/2012 | Nygaard | G06T 7/0004 |
| | | | | 348/46 |
| 2013/0142406 | A1* | 6/2013 | Lang | G06K 9/6293 |
| | | | | 382/128 |
| 2015/0154750 | A1 | 6/2015 | Royaee | |
| 2015/0350570 | A1* | 12/2015 | Helgason | H04N 5/33 |
| | | | | 382/128 |
| 2016/0076643 | A1* | 3/2016 | Pellerito | F16H 59/46 |
| | | | | 701/62 |
| 2017/0140601 | A1 | 5/2017 | Kohama et al. | |
| 2017/0305589 | A1 | 10/2017 | Yuyama et al. | |

FOREIGN PATENT DOCUMENTS

| | | | |
|---|---|---|---|
| JP | H10246702 | A | 9/1998 |
| JP | 2004115128 | A | 4/2004 |
| JP | 2013055970 | A * | 3/2013 |
| JP | 2013055970 | A | 3/2013 |
| JP | 2013215343 | A | 10/2013 |
| JP | 2015051040 | A | 3/2015 |
| JP | 2016116942 | A | 6/2016 |
| WO | 2010113436 | A1 | 10/2010 |
| WO | 2015170761 | A1 | 11/2015 |
| WO | 2016047569 | A1 | 3/2016 |
| WO | 2016027849 | A1 | 4/2017 |

OTHER PUBLICATIONS

Written Opinion of the International Searching Authority issued by the Japanese Patent Office acting as the International Searching Authority in relation to International Application No. PCT/JP2018/015338 dated Jul. 10, 2018 (10 pages).
International Search Report issued by the Japanese Patent Office acting as the International Searching Authority in relation to International Application No. PCT/JP2018/015338 dated Jul. 10, 2018 (5 pages) along with English language translation (3 pages).
Office Action issued by the Japanese Patent Office in relation to Japanese Application No. 2020-132570 dated Dec. 15, 2020 (4 pages) along with English language translation (4 pages).
Office Action issued by the Japanese Patent Office in relation to Japanese Application No. 2020-132570 dated Jan. 26, 2021 (4 pages) along with English language translation (4 pages).
Extended European Search Report issued by the European Patent Office in relation to European Application No. 18784624.1 dated Jan. 11, 2021 (9 pages).

* cited by examiner

FIG. 4
(a)
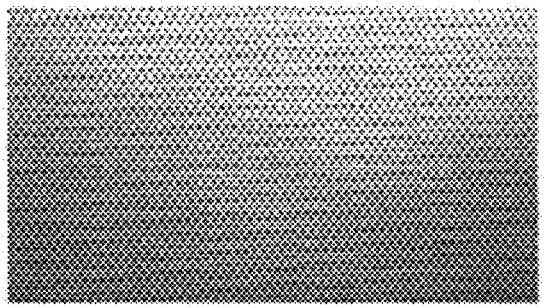
(b)
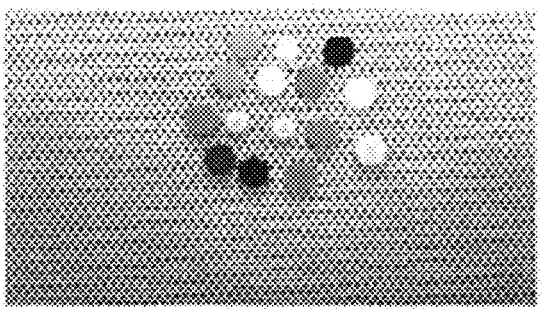
(c)
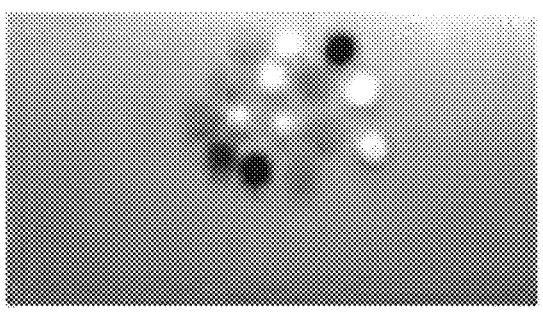
(d)
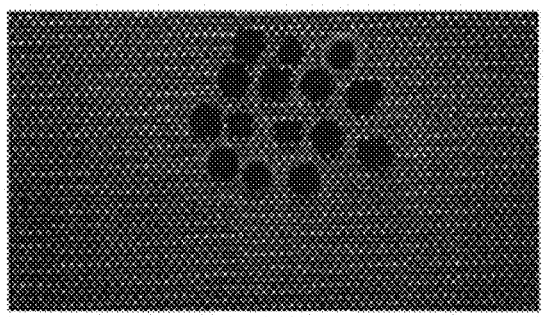

FIG. 20
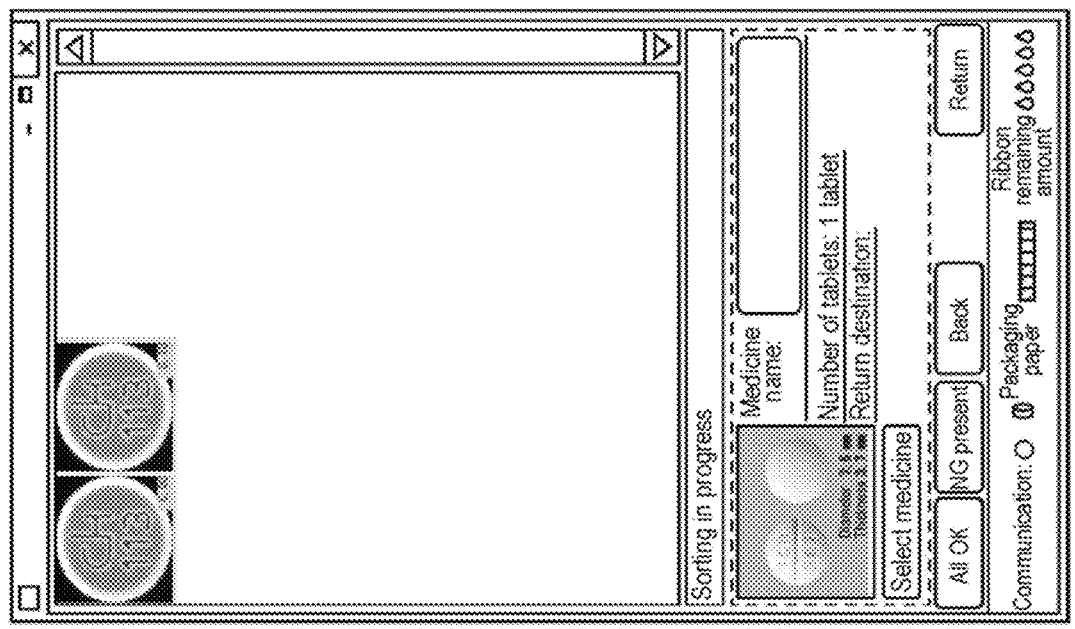
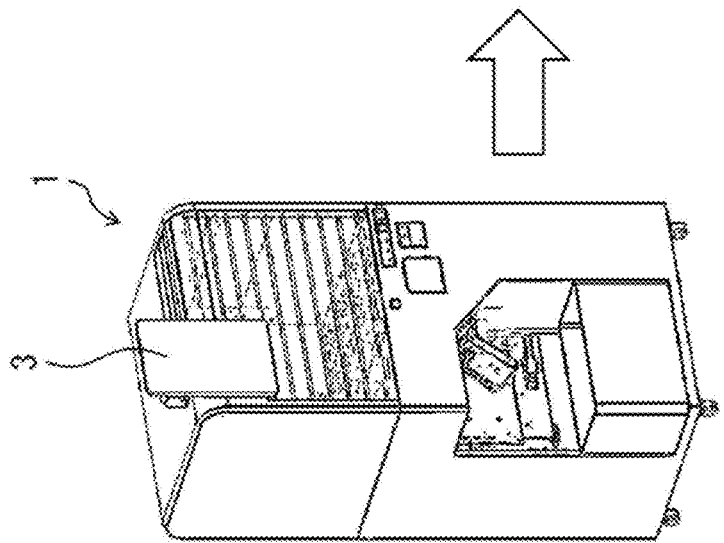

FIG. 21
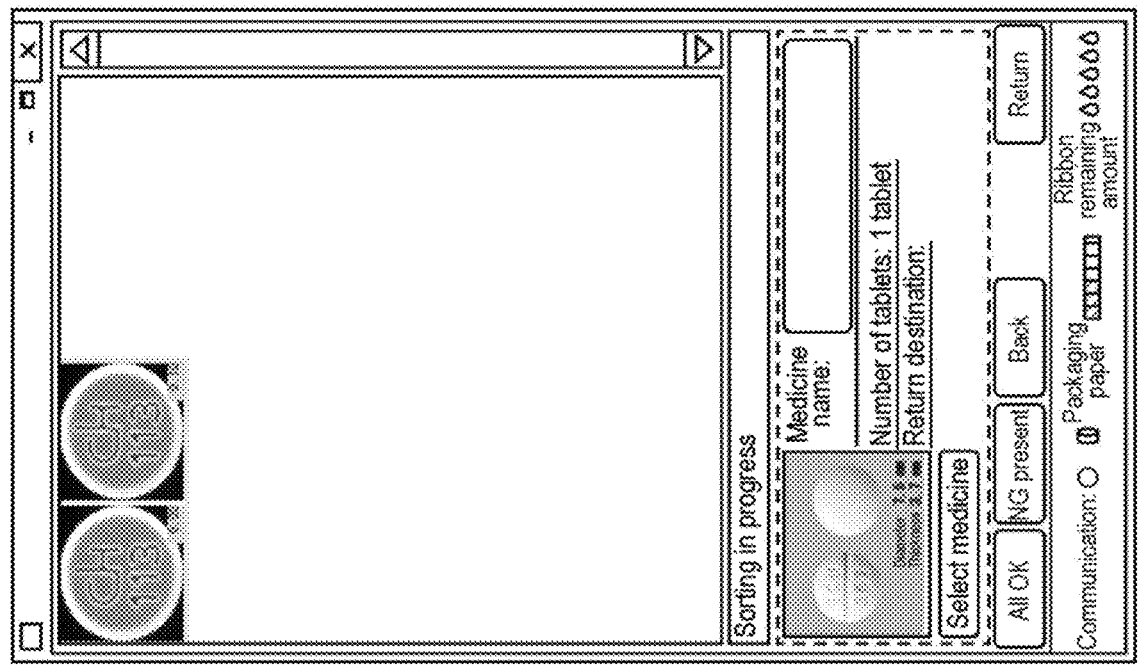
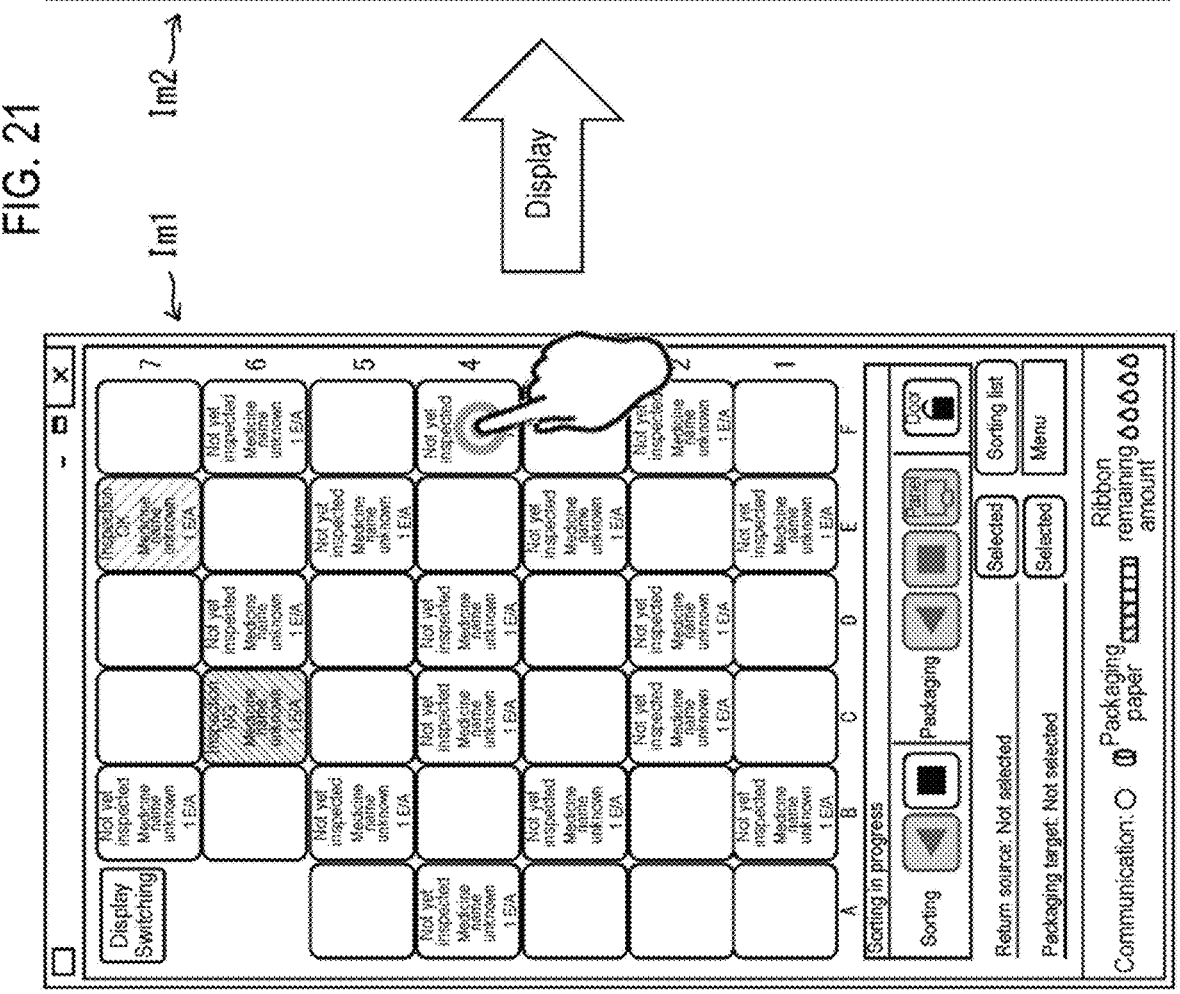

■ Tablet return sorting result ■

Inspection date　: 2006/05/11
Inspection time　: 14:48:57
Inspector　　　　: Pharmacist Medicine name　: AAA 25mg Engraving : @ 221:
Total number of medicines : 15 tablets
Sum of medicine prices : 1,500 Yen
Sorting container : D-7

Return destination 1: ○○○ device 1
　　　　　Cassette No.: 112
　　　　　Stock: 15 tablets
Return destination 2:　 device 2
　　　　　Cassette No.: 113
　　　　　Stock: 20 tablets
Medicine shelf: A-001

(b)　Jo2

[Inspection NG]
■ Tablet return sorting result ■

※ Please manually enter the number of tablets
Inspection date　: 2006/05/11
Inspection time　: 14:48:57
Inspector　　　　: Pharmacist Medicine name　: AAA 25mg Engraving : @ 221:
Total number of medicines : 14 tablets
Sum of medicine prices : 1,500 Yen
Number of inspection NO: 1 tablet
Sorting container : D-7

Return destination 1: ○○○ device 1
　　　　　Cassette No.: 112
　　　　　Stock: 15 tablets
Return destination 2:　 device 2
　　　　　Cassette No.: 113
　　　　　Stock: 20 tablets
Medicine shelf: A-001

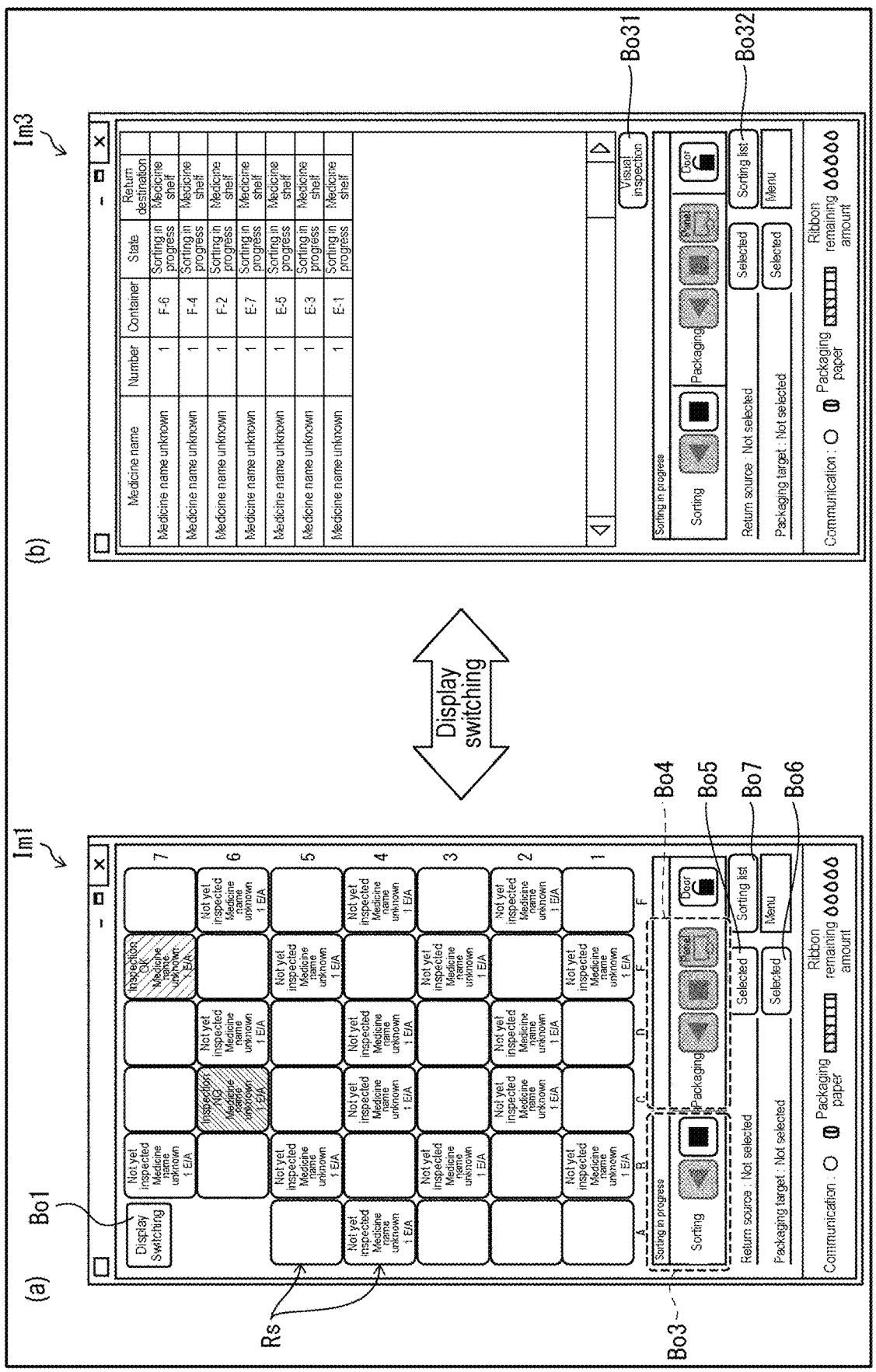

[Totalization result output]

2017/05/25 17:01:56
Start totalization: 2017/05/20
End totalization: 2017/05/24

[1]Medicine 00000000001
　Number of sorted
　medicines : 152

[2]Medicine 00000000002
　Number of sorted
　medicines : 153

[3]Medicine 00000000003
　Number of sorted
　medicines : 154

Total number of sorted
medicines : 459
Total sum of medicine
prices: 15,633-Yen (b)

[Totalization result output]

2017/05/25 19:02:10
Start totalization: 2017/05/20
End totalization: 2017/05/24

[1]Medicine 00000000001
　Sum of medicine
　prices: 5,210-Yen

[2]Medicine 00000000002
　Sum of medicine
　prices: 5,211-Yen

[3]Medicine 00000000003
　Sum of medicine
　prices: 5,212-Yen

Total number of sorted
medicines : 459
Total sum of medicine
prices: 15,633-Yen (c)

[Totalization result output]

2017/05/25 16:56:11
Start totalization: 2017/05/20
End totalization: 2017/05/24

[1]Medicine 00000000001
　Number of sorted
　medicines : 152
　Sum of medicine
　prices: 5,210-Yen

[2]Medicine 00000000002
　Number of sorted
　medicines : 153
　Sum of medicine
　prices: 5,211-Yen

[3]Medicine 00000000003
　Number of sorted
　medicines : 154
　Sum of medicine
　prices: 5,212-Yen Total number of sorted
medicines : 459
Total sum of medicine
prices: 15,633-Yen (d)

[Totalization result output]

2017/05/25 19:22:45
Start totalization: 2017/05/20
End totalization: 2017/05/24

Total number of sorted
medicines : 459
Total sum of medicine
prices: 15,633-Yen

DRUG SORTING DEVICE, SORTING CONTAINER, AND DRUG RETURN METHOD

CROSS-REFERENCE TO RELATED APPLICATIONS

This application is a 35 U.S.C § 371 national stage filing of International Application No. PCT/JP2018/015338, filed on Apr. 12, 2018, which claims the benefit of Japanese Patent Application No. 2017-080623, filed on Apr. 14, 2017 and Japanese Patent Application No. 2018-048554, filed on Mar. 15, 2018, the entire contents of each of which are incorporated by reference herein.

TECHNICAL FIELD

The present invention relates to a medicine sorting device for sorting medicines.

BACKGROUND

Conventionally, a plurality of types of returned medicines have been manually sorted by each type by a pharmacist or physician. A returned medicine is a dispensed medicine that is prescribed or has been prescribed to various patients. Therefore, when compared to a dispensing task in which, based on prescription information per one patient, one or a plurality types of medicines (tablets) are collected (packaged) for each dosing time from a medicine type group (medicine cassette) that is prepared in advance for each medicine type in a dispensing device or the like, returned medicines have a great many types since the medicines prescribed to a plurality of patients are collectively returned. Accordingly, it is highly useful to automatically sort and reuse the returned medicines. Further, in general, medicines to be dispensed for one dosing time are of two to three types, and are of ten types at most.

Further, to avoid the time and effort to be spent for a sorting task or to avoid a risk of erroneous medicine administration caused by a sorting mistake (mistaken return to a medicine cassette), there are some pharmacies or hospitals (precisely, in-hospital pharmacy departments) that discard returned medicines as they are.

Patent Document 1 discloses a medicine sorting device that automatically recognizes and stores returned ampoules or vials. This medicine sorting device recognizes the orientations and postures of ampoules or vials and the properties (e.g., a shape, a size, a type, and an expiration date) of the ampoules or vials. The medicine sorting device disposes ampoules or vials individually by associating storage areas set for the respective ampoules or vials in accordance with the sizes of the recognized ampoules or vials during storage with the identification information of the individual ampoules or vials, and thereby stores the individual ampoules or vials so as to be taken out.

Patent Document 1: International Publication No. WO2015/170761 (published on Nov. 12, 2015)

SUMMARY

However, a target to be returned disclosed in Patent Document 1 is an ampoule or vial, and is not a medicine itself such as a tablet or capsule that is not accommodated in a container or is not yet packaged. Therefore, Patent Document 1 does not assume to identify and automatically sort such a medicine (e.g., tablet or capsule) itself.

An object of one embodiment of the present invention is to realize a medicine sorting device capable of recognizing a medicine itself and automatically sorting the same.

To solve the above object, a medicine sorting device according to one embodiment of the present invention includes: a first accommodating part configured to accommodate a plurality of types of medicines in a mixed state; a second accommodating part configured to accommodate the medicines in a state of being sorted by each type; an imaging part configured to image the medicines; a discrimination part configured to discriminate the types of the medicines based on images captured by the imaging part; and a sorting part configured to sort the medicines by each type based on a discrimination result performed by the discrimination part and to store the sorted medicines in the second accommodating part.

According to the above-described configuration, it is possible to sort the medicines by each type by discriminating the types of the medicines, which are mixed and accommodated in the first accommodating part, by using captured images. Therefore, the medicine sorting device or a user (e.g., a medical worker such as a physician or a pharmacist) can efficiently and more safely perform post-sorting, processes (e.g., visual inspection, packaging, and return to a medicine shelf (a dispensing shelf)).

Further, the medicine is not an ampoule or a vial (in other words, a medicine accommodated in a container) but is a medicine that is not accommodated in a container or the like or is not yet packaged. Therefore, according to the above-described configuration, it is possible to automatically sort a plurality of types of medicines based on the discriminated result.

Further, the medicine sorting device according to one embodiment of the present invention may include a rotation part configured to rotate the imaging part such that the imaging part turns around a disposition area in which the medicine to be imaged is disposed. The imaging part may image the medicine disposed in the disposition area from a plurality of positions where the imaging part is rotated by the rotation part.

According to the above-described configuration, it is possible to image the medicine from a plurality of directions in the state where the medicine is disposed (fixed) in the disposition area.

Further, the medicine sorting device according to one embodiment of the present invention may include an image classification part configured to classify the image captured by the imaging part for each type of the medicine discriminated by the discrimination part.

According to the above-described configuration, it is possible to classify medicine images so as to coincide with the medicine discrimination results (sorting results). By looking at the images classified in this manner, it is possible for the user to confirm whether or not the sorted medicines are of the same type (to perform a visual inspection).

Further, in the medicine sorting device according to one embodiment of the present invention, the determination part may extract a feature of the medicine from each of the images captured by the imaging part, and may perform discrimination by collating the feature with a medicine database that manages a medicine data related to the plurality of types of medicines According to the above-described configuration, by performing the discrimination by collating the extracted feature with the medicine database, it is possible to sort the same type of medicines into the same position of the second accommodation part. Therefore, it is possible for the medicine sorting device or the user to perform the post-sorting process efficiently and more safely.

Further, in the medicine sorting device according to one embodiment of the present invention, the determination part may extract features of the medicine from each of the images captured by the imaging part, and may perform the discrimination in accordance with whether or not the features are the same by comparing the features with each other According to the above-described configuration, it is possible to sort the medicines that are regarded as having the same features into the same position in the second accommodating part. Therefore, it is possible for the medicine sorting device or the user to perform the post-sorting process efficiently and more safely. Further, even when the medicine data related to the imaged medicines is not included in the medicine database that manages medicine data related to a plurality of types of medicines (even if the medicine data is not registered in advance in the medicine database), it is possible to sort the medicine.

Further, in the medicine sorting device according to one embodiment of the present invention, when the images of the medicines imaged by the imaging part are used as reference images, the discrimination part may compare the features of the medicines in the images of the medicines, which are imaged by the imaging part after the reference images are acquired, with the features of the medicines in the reference images.

According to the above-described configuration, it is possible to sort a medicine that is not included in the medicine database.

Further, the medicine sorting device according to one embodiment of the present invention may include an ultraviolet light radiation part configured to radiate ultraviolet light to the medicine to be imaged. The discrimination part may perform the discrimination based on an imaging result of the medicine captured in the state where the ultraviolet light is radiated.

If ultraviolet light is radiated to a medicine, different fluorescences are emitted depending upon the components of the medicine. Therefore, by radiating the ultraviolet light to the medicine as described above and imaging the medicine, it is possible to discriminate the type of the medicine even if the medicines have the same color (e.g., white color). Therefore, since the performance of the type discrimination process is improved, it is possible to rapidly sort a huge amount of medicines.

Further, in the medicine sorting device according to one embodiment of the present invention, the discrimination part may perform the discrimination by narrowing down candidates of medicine data related to the imaged medicines from a medicine database that manages medicine data related to the plurality of types of medicines.

According to the above-described configuration, it is possible to narrow down the candidates of medicine data even if the medicines have the same color. That is, since the performance of narrowing down the candidates of medicine data is improved, it is possible to rapidly sort a huge amount of medicines.

Further, the medicine sorting device according to one embodiment of the present invention may include: a medicine placement table on which the medicine to be imaged is placed; and a movement mechanism configured to move the medicine placement table. The movement mechanism may move the medicine placement table from a placement area where the medicine is placed to a disposition area where the medicine is disposed such that the medicine is opposed to the imaging part, and may move the medicine placement table from the disposition area to a sorting standby area where the medicine placement table waits for sorting the medicine to the second accommodating part.

According to the above-described configuration, merely by placing a medicine to be imaged on the medicine placement table in the placement area, the sorting device can image the medicine in the disposition area, and may cause the medicine after imaging (after type discrimination) to wait for being sorted to the second accommodating part in the sorting standby area. In other words, since the medicine sorting device includes the medicine placement table and the movement mechanism, it is possible to smoothly perform the processes from the imaging of the medicine to just before the sorting of the medicine to the second accommodating part.

Further, in the medicine sorting device according to one embodiment of the present invention, two medicine placement tables may be provided and each of the medicine placement tables is provided at an end portion of a shaft portion. When one of the two medicine placement tables is disposed in the disposition area by turning the shaft portion, the movement mechanism may dispose the other of the two medicine placement tables in the placement area or the sorting standby area.

According to the above-described configuration, while a medicine placed on one of the medicine placement tables is being imaged, it is possible to place a medicine to be newly imaged on the other of the medicine placement tables, or to sort the imaged medicine placed on the other of the medicine placement tables into the second accommodating part. Therefore, since the medicine sorting device can perform the imaging of a medicine and the placement or sorting of a medicine in parallel, it is possible to shorten the processing time. Moreover, since it is not necessary to prepare another placement unit in each of the above areas, it is possible to achieve the downsizing of the medicine sorting device.

Further, in the medicine sorting device according to one embodiment of the present invention, when medicine data related to the medicine is uniquely specified by a user's visual inspection, the medicine data may be registered in a medicine database that manages medicine data related to the plurality of types of medicines.

According to the above-described configuration, it is possible to register the medicine data related to the medicine uniquely specified by visual inspection in the medicine database. Therefore, it is possible to register a new medicine in the medicine database, and thus it is possible to update the medicine database at any time. Further, in the stage of creating the new medicine database, it is not necessary that the medicine database includes medicine data related to all medicines.

Further, in the medicine sorting device according to one embodiment of the present invention, when the medicine whose type is discriminated corresponds to a sorting-unneeded medicine that does not need sorting, the discrimination part may exclude the sorting-unneeded medicine from a sorting target.

According to the above-described configuration, it is possible to exclude the medicine designated as a sorting-unneeded medicine from the sorting target. Therefore, it is possible to exclude an unnecessary process such as a sorting process or a visual inspection process for the sorting-unneeded medicine. Further, it is possible to shorten the time for the sorting process and the visual inspection process.

Further, in the medicine sorting device according to one embodiment of the present invention, the sorting part may include: an adsorption mechanism that moves to the first accommodating part in a position opposed to the first accommodating part to adsorb the medicine accommodated in the first accommodating part; and a sensor that detects a suction force for adsorbing the medicine by the adsorption mechanism. A first threshold value for determining whether or not the medicine exists in the vicinity of a tip portion of the adsorption mechanism and a second threshold value for determining that the medicine is adsorbed to the tip portion may set in the sensor.

According to the above-described configuration, it is possible to prevent the medicines stacked in the first accommodating part from collapsing due to the tip portion during the adsorption of a medicine.

Further, in the medicine sorting device according to one embodiment of the present invention, the discrimination part may perform a recognition process on a plurality of characters given to a medicine included in an image captured by the imaging part. Among the plurality of characters recognized in the recognition process, the discrimination part may determine characters, which are determined as having a size in a predetermined range and forming a string, as a plurality of characters actually formed in the medicine.

According to the above-described configuration, it is possible to improve the reading accuracy of a plurality of symbols given to a medicine.

Further, the medicine sorting device according to one embodiment of the present invention may include an imaging control part configured to control the imaging part. The imaging control part may determine whether or not an imaging position of the imaging part is a predefined position by comparing a pattern of a predetermined portion other than a medicine, which is included in an image captured by the imaging part, with a predetermined pattern included in an image captured in advance by the imaging part.

According to the above-described configuration, it is possible to determine whether or not the imaging position is the predefined position based on the pattern of the predetermined portion included in the captured image. Therefore, it is possible to confirm the imaging position by a simple method.

Further, the medicine sorting device according to one embodiment of the present invention may include a shaft portion that supports a medicine placement table which is disposed in the disposition area and on which the medicine to be imaged is placed. When the medicine placement table is disposed in the disposition area, the shaft portion may be parallel with an axial direction about which the imaging part is rotated. The patterns of the predetermined portion may be different in at least a portion in a circumferential direction of the shaft portion.

According to the above-described configuration, since the patterns of the predetermined portion are different in the circumferential direction of the shaft portion, it is possible for the imaging part to image different patterns at each of a plurality of positions. Therefore, it is possible to specify the imaging position based on the captured patterns.

Further, in the medicine sorting device according to one embodiment of the present invention, the sorting part may sort a medicine, which is one of the medicines and is specified as a target to be taken out from the medicine sorting device based on return destination information related to a return destination of a sorted medicine, to a medicine take-out side in the medicine sorting device.

According to the above-described configuration, the medicine, which is specified as the target to be taken out from the medicine sorting device based on the return destination information (that is, in accordance with the specification of the return destination) can be sorted to a position where the medicine is easily taken out from the medicine sorting device. Therefore, the user can easily take out the medicine.

Further, the medicine sorting device according to one embodiment of the present invention may include a medicine placement table on which the medicine to be imaged is placed. The imaging part may image the medicine from a first direction opposed to a placement surface of the medicine placement table on which the medicine is placed, or from a second direction opposite to the first direction. The determination part may determine whether or not the medicine is a tablet based on a shape of the medicine included in an image captured from the first direction or the second direction.

According to the above-described configuration, it is possible to determine whether the medicine is a tablet or a capsule by imaging the medicine from the first direction or the second direction.

Further, in the medicine sorting device according to one embodiment of the present invention, when the determination part cannot determine whether or not the medicine is a tablet based on the image captured from the first direction or the second direction, the imaging part may image the medicine from an oblique direction with respect to the placement surface, and the determination part may determine whether or not the medicine is a tablet based on the shape of the medicine included in the images captured from the first direction or the second direction and from the oblique direction.

When the medicine is a capsule, the shape when imaged from the first direction or the second direction and the shape when imaged from then oblique direction are substantially the same. However, when the medicine is a tablet, the abovementioned two shapes are different from each other. Therefore, it is possible reliably determine whether the medicine is a tablet or a capsule, by using the image captured from the oblique direction in addition to then image captured from the first direction or the second direction.

Further, the medicine sorting device according to one embodiment of the present invention may include a detection area changing part. The detection area changing part may change a detection area for detecting the medicine accommodated in a sorting container which is disposed in the second accommodating part and accommodates the medicine sorted by the sorting part, in accordance with whether or not an image obtained by imaging the sorting container includes at least a portion of a bottom portion of the sorting container, or may change a detection area for detecting the medicine accommodated in the first accommodating part in accordance with whether or not an image obtained by imaging the first accommodating part includes at least a portion of a bottom portion of the first accommodating part.

When the bottom portion is included in the image, it may be determined that the number of medicines accommodated in the sorting container or the first accommodating part is small. Therefore, according to the above-described configuration, by changing the detection area in accordance with whether the bottom portion is included in the image, it is possible to specify the detection area in accordance with the number of medicines accommodated in the sorting container or the first accommodating part may be specified. Therefore, it is possible to take out a medicine more reliably.

Further, in the medicine sorting device according to one embodiment of the present invention, a plurality of pieces of medicine-specific information for specifying a medicine may be assigned to each of the plurality of types of medicines. Among the plurality of pieces of medicine-specific information, at least one medicine-specific information related to the medicine sorted by the sorting part may be acquired from a return destination to which the sorted medicine is returned or a return assisting device for returning to the return destination. (1) The at least one medicine-specific information may be stored in an information recording medium provided in the sorting container that stores the sorted medicine, or (2) The at least one piece of medicine-specific information may be printed in a journal in which medicine data related to a medicine reflecting a user's visual inspection result is printed.

When a plurality of pieces of medicine-specific information related to any medicine and managed by the return destination or the return assisting device does not completely match a plurality of pieces of medicine-specific information related to the medicine and managed by the medicine sorting device, the medicine-specific information, which is stored in an information recording medium or printed in a journal by the medicine sorting device, may not be read by the return destination or the return assisting device. According to the above-described configuration, since the medicine-specific information used in the return destination or the return assisting device is stored in the information recording medium or printed in the journal, it is possible to reliably read the medicine-specific information by the return destination or the return assisting device.

Further, in the medicine sorting device according to one embodiment of the present invention, a plurality of sorting containers that accommodate medicines sorted by the sorting part may be disposed in the second accommodating part. In regard to a medicine, which a user desires to sort into a predetermined sorting container of the plurality of sorting containers, among medicines included in a medicine database that manages medicine data related to the plurality of types of medicines, sorting identification information for sorting the medicine to the predetermined sorting container may be given by a user input. The sorting part may sort the medicine, to which the sorting identification information is given, to the predetermined sorting container to which the sorting identification information is given.

According to the above-described configuration, it is possible to sort a predetermined medicine into a predetermined sorting container according to the user's desire.

Further, a sorting container according to one embodiment of the present invention is disposed in the second accommodating part of one of the medicine sorting devices configured above, and accommodates a medicine sorted by the medicine sorting device. An opening through which the medicine sorted by the medicine sorting device is inserted is formed at a top side of the sorting container. When viewed from the opening side, the sorting container has a rectangular shape. A convex portion is provided in at least one of a plurality of sides constituting an edge portion that is as an outer periphery of the opening.

According to the above-described configuration, by providing the convex portion on any of the plurality of sides constituting the edge portion, it is possible to easily take out a sorting container from the second accommodating part. Therefore, it is possible to improve the convenience of the sorting container.

Further, in the sorting container according to one embodiment of the present invention, the convex portion may be provided in each of two adjacent sides such that the convex portions are adjacent to each other, and adjacent portions of the convex portions, which are adjacent to each other, may have a same height.

According to the above-described configuration, it is possible to widen the convex portion, and thus it is possible improve the ease of handling the sorting container.

Further, in the sorting container according to one embodiment of the present invention, at a connection portion between the edge portion and an outer wall of the sorting container, the edge portion may protrude outwards from the outer wall.

According to the above-described configuration, by providing a protruding portion, it is possible to improve the ease of handling the sorting container.

Further, to solve the above object, a medicine return method according to one embodiment of the present invention includes: a medicine sorting step of sorting a plurality of types of medicines by each type; an inspection step of performing a visual inspection on the medicine sorted in the medicine sorting step; and a return step of returning a visually-inspected medicine to a return destination based on an inspection result in the inspection step.

Further, to solve the above object, a medicine return method according to one embodiment of the present invention includes: a medicine sorting step of sorting a plurality of types of medicines by each type; a display step of displaying an inspection image for performing a visual inspection on the medicine sorted in the medicine sorting step; and a return preparation step of performing a process for enabling a visually-inspected medicine to be returned to a return destination based on a visual inspection result obtained by using the inspection image displayed in the display step.

According to the above-described configuration, it is possible to return the sorted medicines to the return destination through the visual inspection.

Further, in the medicine return method according to one embodiment of the present invention, a plurality of sorting portions to which the medicines are sorted may be prepared in advance, and, by receiving a user input on the sorting position shown in a sorting image showing a sorting state of the medicine, the inspection image of the medicine associated with the sorting position may be displayed in the display step.

According to the above-described configuration, it is possible to display a desired inspection image by a user input on the sorting image.

Further, in the medicine return method according to one embodiment of the present invention, a sorting container for accommodating the sorted medicine may be disposed in each of the plurality of sorting positions to which the medicines are sorted. Data related to the medicine accommodated in the sorting container may be stored in an information recording medium provided in the sorting container. By reading the data related to the medicine, the inspection image of the medicine may be displayed in the display step.

According to the above-described configuration, it is possible to display a desired inspection image by reading the data related to the medicine accommodated in the sorting container.

Further, in the medicine return method according to one embodiment of the present invention, when the medicine sorted in the medicine sorting step is packaged, the inspection image of the medicine may be displayed in the display step by reading medicine data related to the medicine and given to a packaging paper in which the medicine is packaged.

According to the above-described configuration, even in the case where medicines are packaged, it is possible to display a desired inspection image.

Further, in the medicine return method according to one embodiment of the present invention, in the return preparation step, (1) medicine data related to the medicine reflecting the visual inspection result may be stored in an information recording medium provided in a sorting container that accommodates the sorted medicine, (2) a journal printed with the medicine data related to the medicine reflecting the visual inspection result may be issued, or (3) the medicine data related to the medicine reflecting the visual inspection result may be given to a packaging paper in which the medicine is packaged.

According to the above-described configuration, it is possible to read the medicine data related to the medicine reflecting the visual inspection result from the information recording medium of the sorting container, the journal, or the packaging paper. Therefore, it is possible to reliably return the medicine to a desired return destination.

The medicine sorting device according to one embodiment of the present invention has an effect that it is possible to recognize a medicine itself and automatically sort the same.

BRIEF DESCRIPTION OF THE DRAWINGS

FIG. 4 ((a) of FIG. 4) is a view showing an example of a sheet provided on a bottom portion of a first accommodating part provided in the medicine sorting device, and FIG. 4 ((b) to (d) of FIG. 4) is a view illustrating an image analysis process of an imaged sheet.

FIG. 20 is a view showing an example of a processing flow from medicine sorting to medicine return.

FIG. 21 is a view showing an example of an inspection image display method.

FIG. 25 is a view showing an examples of a journal.

FIG. 26 ((a) of FIG. 26) is a view showing an example of a sorting image, and FIG. 26 ((b) of FIG. 26) is a view showing an example of a sorted medicine list image showing information related to sorted medicines.

FIG. 31 ((a) to (d) of FIG. 31) is a view showing an output example when a totalization result is output by a journal.

DETAILED DESCRIPTION

Detailed descriptions are made as to an embodiment of the present invention with reference to FIGS. 1 to 12.

[Outline of Medicine Sorting Device 1]

Figure 1:
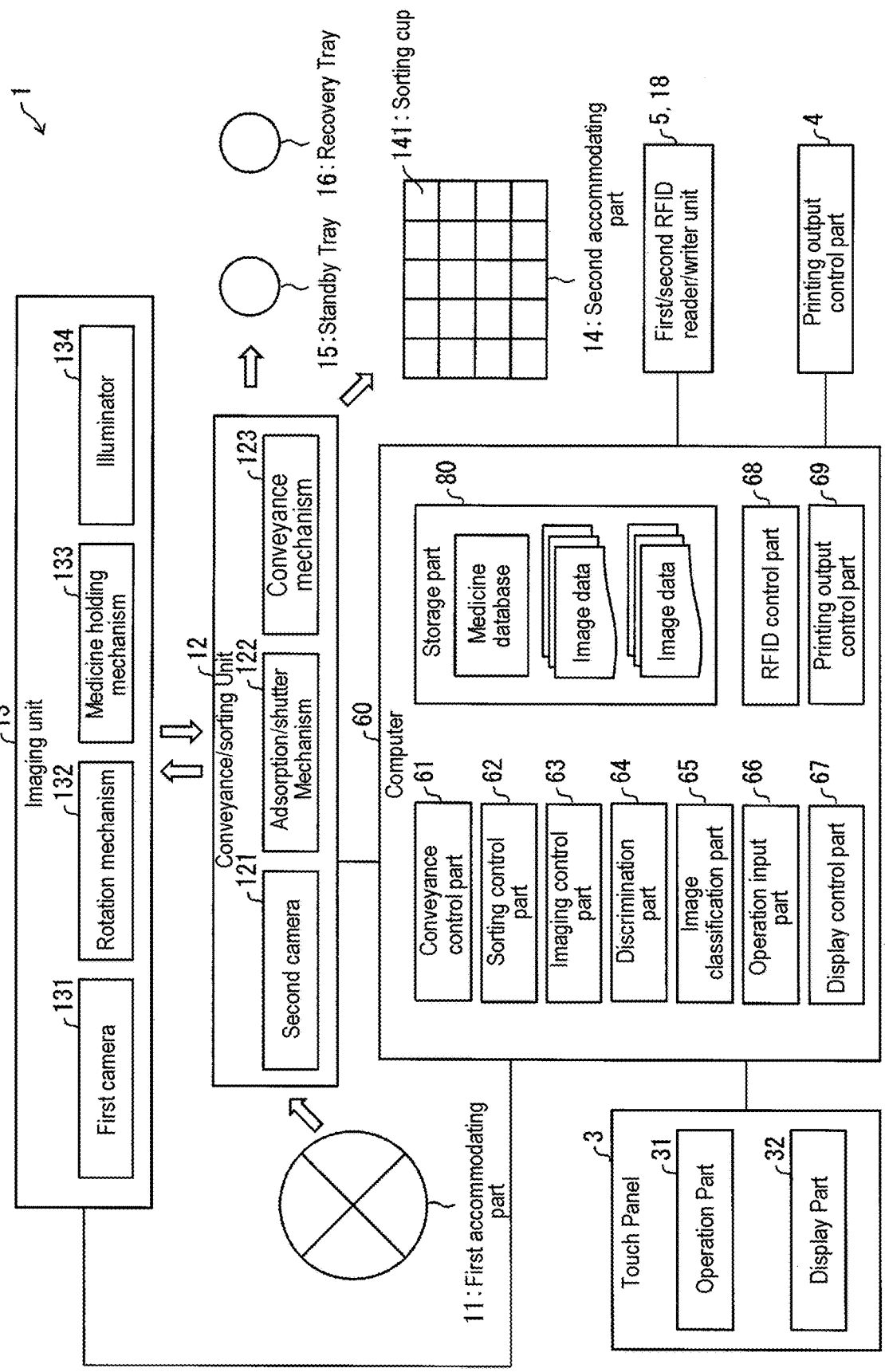
FIG. 1 is a block diagram showing the whole configuration of a medicine sorting device according to one embodiment.
Figure 2:
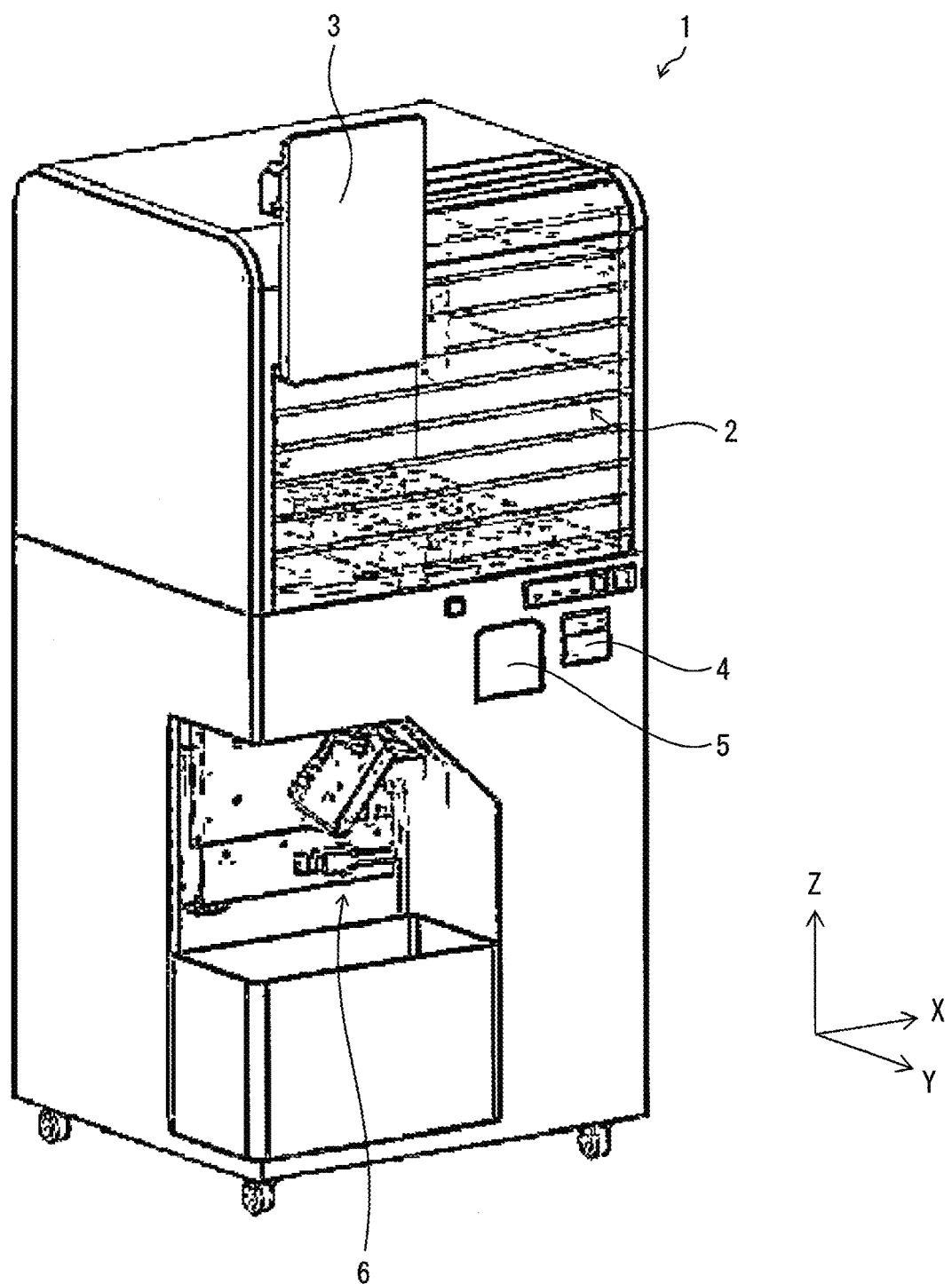
FIG. 2 is a perspective view showing the whole configuration of the medicine sorting device.

First, descriptions are made as to the outline of a medicine sorting device 1 with reference to FIGS. 1 and 2. FIG. 1 is a block diagram showing the whole configuration of the medicine sorting device 1. FIG. 2 is a perspective view showing the whole configuration of the medicine sorting device 1. As shown in FIGS. 1 and 2, the medicine sorting device 1 includes a medicine sorting area 2, a touch panel 3, a printing output part 4, a first radio frequency identifier (RFID) reader/writer unit 5, and a packaging mechanism 6.

The medicine sorting device 1 images each of a plurality types of medicines, discriminates the types of medicines based on the images captured as a result of imaging, and sorts the medicines by each type. Specifically, these processes are performed in the medicine sorting area 2. The medicine sorting area 2 (the internal configuration of the medicine sorting device 1) is described below. Further, the medicine sorted by each type is packaged or returned to a medicine shelf after a visual inspection is made by a user.

In this embodiment, the plurality of types of medicines are medicines that are not accommodated in containers or the like, or medicines that are not yet packaged. By way of example of such medicines, descriptions are made assuming that the medicines are tablets or capsules. Further, descriptions are made assuming that the plurality of types of medicines are returned medicines. The return of medicines includes: the case where medicines adopted in a pharmacy or a hospital are returned as "returned medicines" to the pharmacy or hospital; and the case where "brought medicines", which may include medicines issued from other pharmacies or hospitals, are returned to the pharmacy or hospital in addition to the adopted medicines. In other words, the concept of the returned medicine includes at least one of the above-mentioned "returned medicine" and "brought medicine." After medicines are returned, the medicine sorting device 1 can automatically perform the processes from image-capturing to sorting after medicines are returned.

The touch panel 3 receives various user inputs at an operation part 31, and displays various images (e.g., images showing how medicine are sorted, images for visual inspection) at a display part 32.

In response to a user input after visual inspection, the printing output part 4 prints a journal that shows medicine data related to the visually-inspected medicines (e.g., the data indicative of medicine names, manufacturers, or components). The medicine data may include image data that indicates an image unique to the medicine.

The first RFID reader/writer unit 5 reads data (e.g., the number of stored medicines, medicine data, and image data acquired by the imaging unit 13) which is stored in an RFID tag (not shown) provided in a bottom portion of each sorting cup 141 of a second accommodating part 14, and which is related to the medicines stored in each sorting cup 141. The data may include medicine data determined by the visual inspection (the medicine data after visual inspection). Further, the medicine data after visual inspection may be written in the RFID tag. The medicine data after visual inspection is used at the following: (1) when the medicines stored in the corresponding sorting cup 141 are packaged by the packaging mechanism 6 or a packaging device different from the medicine sorting device 1, or (2) when the medicines stored in the corresponding sorting cup 141 are returned to a medicine shelf.

The packaging mechanism 6 packages the sorted medicines. The packaging mechanism 6 is an optional mechanism. When the packaging mechanism 6 is provided in the medicine sorting device 1, the medicine sorting device 1 can collectively perform the processes from sorting the returned medicines to packaging the medicines after the visual inspection. In particular, when the medicines are input to the packaging mechanism 6 by a conveyance/sorting unit 12, the processes from the sorting to the packaging can be automatically performed except the visual inspection.

A tablet packaging device or a packaging part of a powder medicine packaging device, which have been used conventionally, may be used as the packaging mechanism 6. In this case, the medicines in the sorting cup 141, which are sorted by, for example, the same medicine type, may be packaged into one package or a plurality of packages. Further, during the packaging process, the medicine names of the medicines in the sorting cup 141, which are stored in the RFID tag of the sorting cup 141, are printed on a packaging paper by a printing mechanism provided in the packaging mechanism 6. Further, a bar code including medicine name information of the medicines is printed on each package. These printings are utilized when the medicines are returned to the medicine shelf, or when the medicines are returned to the tablet packaging device.

[Basic Configuration of Medicine Sorting Area 2]

Figure 3:
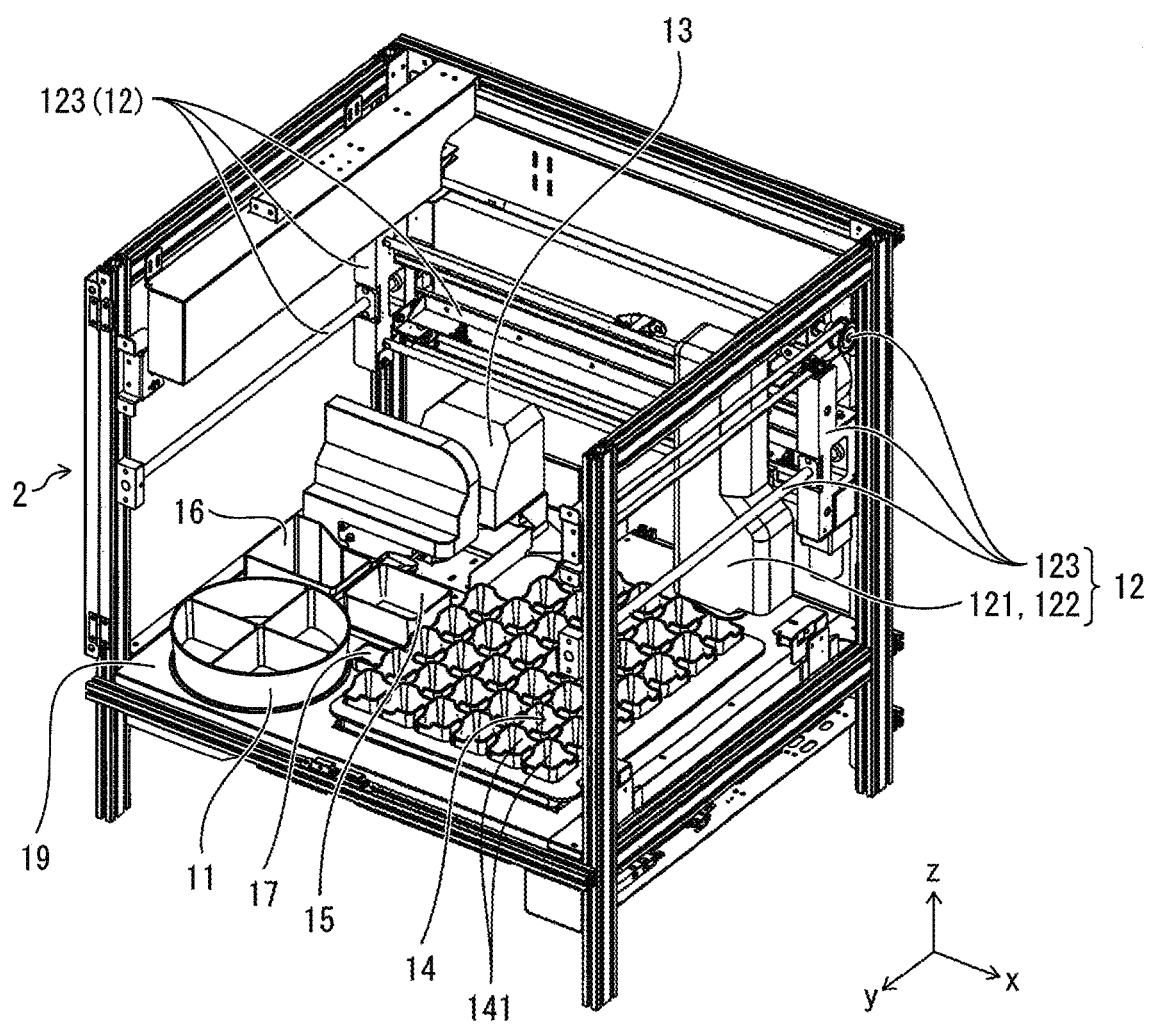
FIG. 3 is a perspective view showing a basic configuration of a medicine sorting area provided in the medicine sorting device.

Next, the basic configuration of the medicine sorting area 2 (the internal configuration of the medicine sorting device 1) is described with reference to FIGS. 1 and 3. FIG. 3 is a perspective view showing the basic configuration of the medicine sorting device 2.

As shown in FIGS. 1 and 3, the medicine sorting area 2 mainly includes, as hardware, a first accommodating part 11, a conveyance/sorting unit 12 (sorting part), an imaging unit 13, a second accommodating part 14, and a standby tray 15, a recovery tray 16, a medicine inlet 17, and a second RFID reader/writer unit 18. Each member except the conveyance/sorting, unit 12 is provided on a pedestal 19. The main functions of the conveyance/sorting unit 12, the imaging unit 13, and the second RFID reader/writer unit 18 are described in detail in the descriptions on each process to be described below.

The first accommodating part 11 accommodates, in a mixed state, a plurality of types of medicines that are returned by a user. In this embodiment, the first accommodating part 11 is divided into a plurality of accommodating portions. In this case, for example, if all the medicines accommodated in one accommodating portion are conveyed by the conveyance/sorting unit 12, then the medicines accommodated in another accommodating portion adjacent to the accommodating portion become a target to be conveyed. Further, the first accommodating part 11 may be provided to be rotatable about a Z-axis (a center of a column shape). In this case, a control part of a computer 60 (hereinafter, simply referred to as a control part) may rotate the first accommodating part 11 such that the conveyance/sorting unit 12 can easily acquire the medicines, for example, at the timing when one accommodating portion becomes empty.

The first accommodating part 11 has a column shape. With this shape, it is possible to increase an accommodation capacity. If this point is not taken into consideration, the shape of the first accommodating part is not limited to the column shape, and it can has any shape as long as it can accommodate a plurality of types of medicines. Further, a dot-shaped pattern or unevenness may be provided on a bottom portion of the first accommodating part 11. In this case, the control part can specify that the first accommodating part 11 is empty, by analyzing an image captured by a second camera 121.

When said dot shape is represented by a pattern, is realized, for example, by a sheet (see (a) of FIG. 4) in which black dots sufficiently smaller than medicines to be detected are printed at equal intervals. The sheet is white paper and the interval between black dots is substantially the same as a size of the black dot. Further, when said dot shape is represented by unevenness, it is realized by a sheet in which concave portions or convex portions sufficiently smaller than the medicines to be detected are provided at equal intervals. The black dots or the unevenness may be provided directly on the bottom portion of the first accommodating part 11 instead of the sheet. Further, the same pattern or unevenness may also be provided on the bottom portion of the sorting cup 141.

The second accommodating part 14 includes a plurality of sorting cups 141 that accommodate medicines in the state where the medicines are sorted by each type. The control part discriminates the types of medicines based on the images of the medicines imaged by the imaging unit 13, and determines the sorting cup 141 for storing the medicines based on the discrimination result. The medicines are conveyed to and stored in the determined sorting cup 141 by the conveyance/sorting unit 12.

The standby tray 15 is an accommodating part for temporarily containing medicines, whose types are discriminated by the control part other than medicines stored in all the sorting cups 141 when all the sorting cups store the medicines. After the medicines are removed from the sorting cup 141, the medicine may be conveyed from the standby tray 15 to the sorting cup 141.

The recovery tray 16 is an accommodating part for storing objects whose types cannot be discriminated by the control part (e.g., foreign matters other than medicines). Examples of the foreign matters other than medicines may include fragments of a PTP (Press Through Pack) sheet. There is a possibility that the fragments of the PTP sheet may be mixed to the first accommodating part 11 when medicines are returned.

When the medicine sorting device 1 is provided with the packaging mechanism 6, the medicine inlet 17 is used for conveying the medicines stored in the second accommodating part 14 to the packaging mechanism 6 by the conveyance/sorting unit 12. Naturally, when the medicine sorting device 1 is not provided with the packaging mechanism 6, the medicine inlet 17 is unnecessary.

Further, as shown in FIG. 1, the medicine sorting device is provided with a computer 60 that integrally controls the above-mentioned each member (hardware) of the medicine sorting device 1. The computer 60 mainly includes, as control parts (software), a conveyance control part 61, a sorting control part 62, an imaging control part 63, a discrimination part 64, an image classification part 65, an operation input part 66, a display control part 67, and an RFID control part 68, and a printing output control part 69. The conveyance control part 61, the sorting control part 62, the imaging control part 63, the discrimination part 64, and the image classification part 65 are described in detail in the descriptions on each process to be described below.

The operation input part 66 and the display control part 67 control the operation part 31 and the display part 32 of the touch panel 3, respectively. The RFID control part 68 controls the first RFID reader/writer unit 5 and the second RFID reader/writer unit 18. The printing output control part 69 controls the printing output part 4 in response to the user input received by the operation input part 66. Further, when the medicine sorting device 1 is provided with the packaging mechanism 6, the computer 60 includes, as control part, a packaging control part that controls the packaging mechanism 6.

Further, the computer 60 includes a storage part 80. The storage part 80 stores, for example, a medicine database (medicine master) for managing medicine data related to a plurality of types of medicines, and image data imaged by a first camera 131. Further, the storage part 80 stores data in which discrimination results of the discrimination part 64 are associated with medicine sorting positions determined by the sorting control part 62. This data may be referred to as sorting state data in which medicines and sorting positions are associated with each other from the start of sorting to the completion of sorting.

Further, the medicine database, the image data, and the sorting state data may not be managed by the storage part 80, and may be managed by, for example, an external device. In this case, the control part may acquire the medicine database, the image data, and the sorting state data from the external device via a communication line, such as the Internet, when necessary. Further, the medicine database may be updated by adding new medicine data thereto.

[Outline of Processes in Medicine Sorting Device 1]

In the medicine sorting device 1, the conveyance/sorting unit 12 conveys each medicine, which is returned to the first accommodating part 11, to the imaging unit 13. The imaging unit 13 sequentially images each conveyed medicine. The control part discriminates the type of each medicine based on captured images, and determines the sorting position of each discriminated medicine in the second accommodating part 14. The conveyance/sorting unit 12 conveys each medicine to the determined sorting positions. Information on the medicines stored in the second accommodating part 14 is written in the RFID tags of the sorting cups 141, or is stored in the storage part 80, or is displayed on the touch panel 3. Further, when the user manipulates the touch panel 3 after the sorting of the medicines is completed or during the sorting of the medicines, the processes such as visual inspection and packaging are performed. Hereinafter, each process is described specifically.

[Medicine Conveyance Process to Imaging Unit 13]

Figure 5:
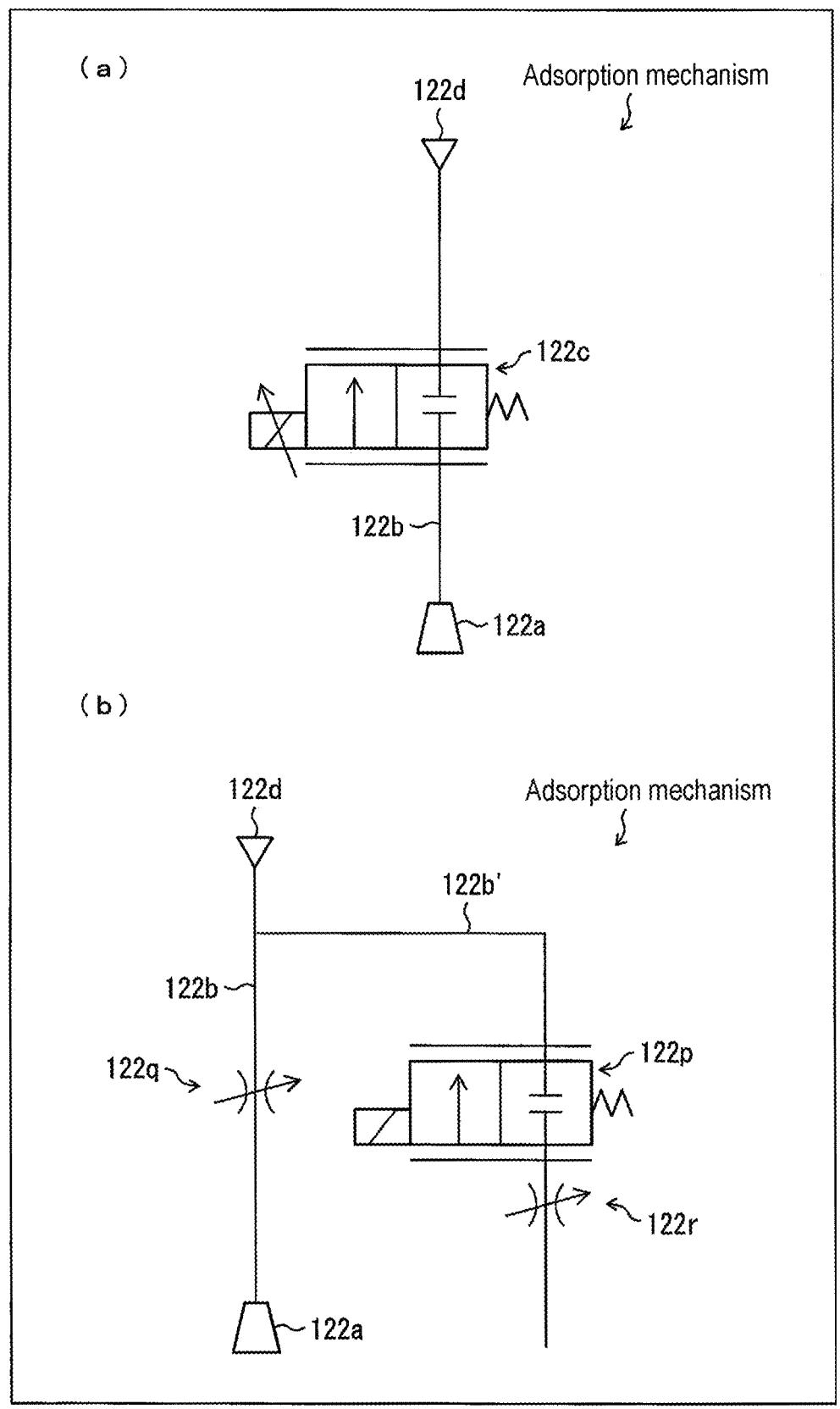
FIG. 5 ((a) and (b) of FIG. 5) is a schematic view showing an example of a control valve provided in an adsorption mechanism provided in the medicine sorting device.

First, a medicine conveyance process from the first accommodating part 11 to the imaging unit 13 is described with reference to FIGS. 1 and 3 to 5. In FIG. 4, (a) of FIG. 4 is a view showing an example of a sheet provided on the bottom portion of the first accommodating part 11, and (b) to (d) of FIG. 4 are views illustrating an image analysis process of imaged sheets. In FIG. 5, (a) and (b) of FIG. 5 are schematic views each showing an example of a control valve provided in an adsorption mechanism. The medicine conveyance process is mainly performed by the conveyance/sorting unit 12 and the conveyance control part 61.

Figure 6:
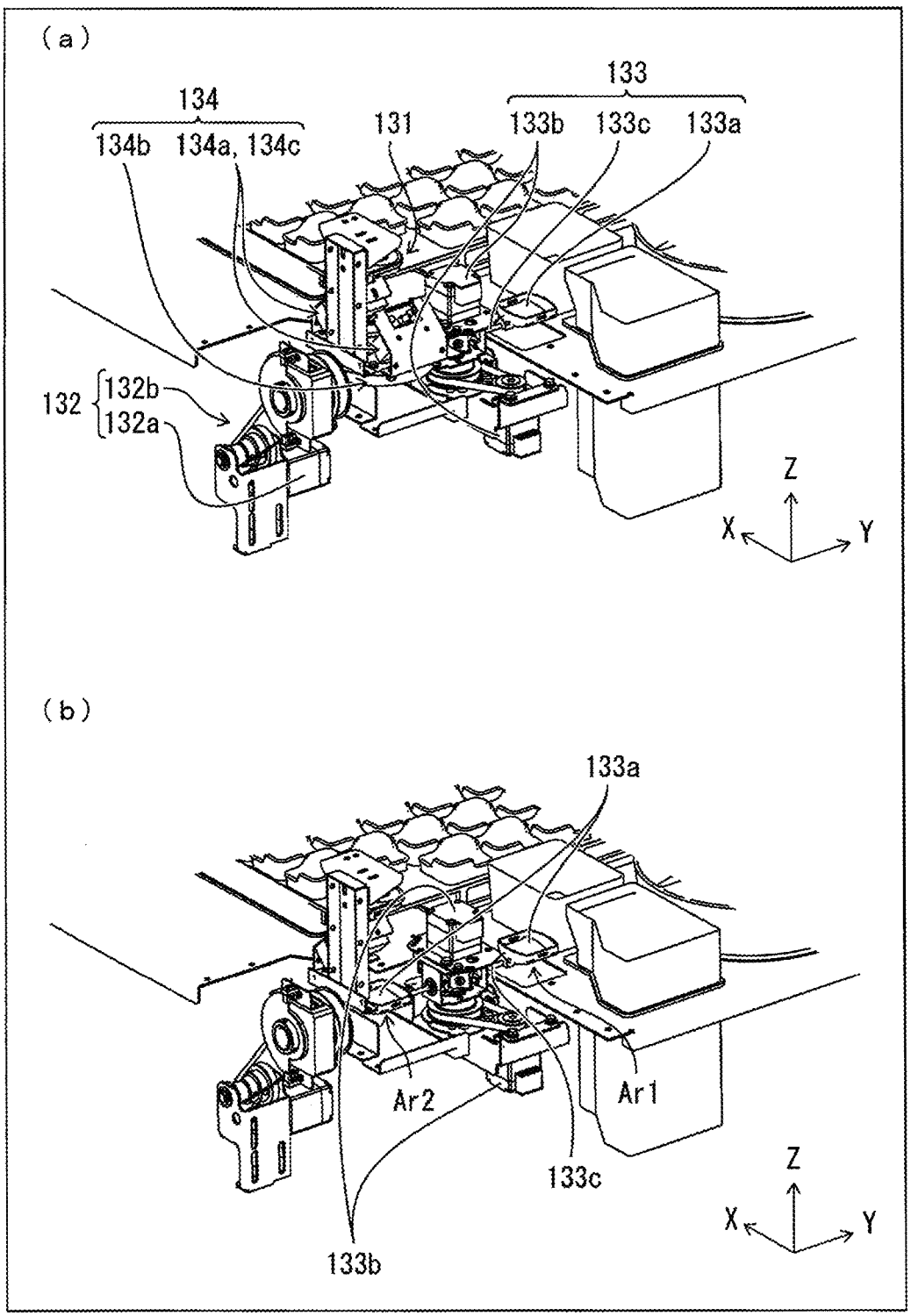
FIG. 6 ((a) and (b) of FIG. 6) is a perspective view showing the whole configuration of an imaging unit provided in the medicine sorting device.

Specifically, the conveyance/sorting unit 12 conveys the medicines accommodated in the first accommodating part 11 to a receiving area Ar1 (see (b) of FIG. 6) where the imaging unit 13 receives the medicines. The conveyance control part 61 controls the conveyance process performed by the conveyance/sorting unit 12.

The conveyance/sorting unit 12 includes a second camera 121, an adsorption/shutter mechanism 122, and a conveyance mechanism 123.

The second camera 121 sequentially images the first accommodating part 11 in order to specify medicines to be conveyed. The imaging control part 63 controls the imaging process of the second camera 121. The second camera 121 is provided at an end portion of the conveyance/sorting unit 12 which faces toward the pedestal 19 (specifically, an end portion of a housing including at least the adsorption/shutter mechanism 122). The second camera 121 may be provided at a tip portion of the adsorption mechanism to be described below. The imaging control part 63 analyzes a captured image and determines whether or not a medicine is included in the image. When it is determined that the medicine is included, the conveyance control part 61 causes, for example, the tip portion to approach to the first accommodating part 11 and specifies the medicine included in the image captured at that time as a medicine to be conveyed.

More specifically, the second camera 121 images the entirety of one of a plurality of accommodating portions included in the first accommodating part 11. The imaging control part 63 converts the image including the accommodating portion into a brightness image obtained by binarizing the image based on the difference in light and darkness, and specifies the contour and area of a mass composed of plural medicines based on the boundary in light and darkness in the brightness image (medicine area specifying method 1). The imaging control part 63 adsorbs one medicine contained in the accommodating portion by causing the tip portion to approach a position in the accommodating portion, which corresponds to the area including the brightest portion of the specified areas.

A visible light source (not shown) is provided in the vicinity of the second camera 121, and visible light is radiated from above the accommodating portion (in a direction of +Z axis) when the second camera 121 captures an image. Therefore, it may be determined that the brightest portion in the brightness image is closest to the tip portion in the accommodating portion. Therefore, it is possible to acquire images from the medicine closest to the tip portion by causing the tip portion to approach the area including the brightest portion. Further, the brightness image may be an image obtained by converting any one of hue, saturation, and brightness, which are attributes of an image, with respect to the captured image of the medicine.

Further, the imaging control part 63 may specify the positions of the medicines contained in the first accommodating part 11 by performing image analysis as shown in (b) to (d) of FIG. 4 (medicine area specifying method 2). Further, it is assumed that black dots sufficiently smaller than medicines to be detected are printed at equal intervals on the bottom portion of the first accommodating part 11.

Specifically, as shown in (b) of FIG. 4, the imaging control part 63 converts an image including a plurality of medicines accommodated in one accommodating portion of the first accommodating part 11 into a brightness image, and creates a flattened image shown in (c) of FIG. 4 by performing a flattening process. The imaging control part 63 obtains the difference between the gradation value of the brightness image and the gradation value of the flattened image, and determines that an area having the difference smaller than a predetermined value is an area of the medicine included in the image. In FIG. 4, (d) of FIG. 4 is a difference image created after the difference is obtained.

As shown in (c) and (d) of FIG. 4, the difference of the gradation values is larger in an area where no medicine exists in the difference image than in an area where a medicine exists. Therefore, the imaging control part 63 can specify the area having the small difference as the area of the medicine.

In general, regarding specifying the position of the medicine to be conveyed in a mechanism for adsorbing and conveying a medicine, there are some cases where a backlight (transmission illumination) that emits visible light from below the accommodating portion accommodating the medicine is provided and the difference in brightness between the medicine and the background is obtained. However, the backlight may not be provided depending upon the size or cost restriction of a device including such a mechanism, an operation method of the device, or the like. Further, when a medicine and the background are similar in color, the accuracy of position specification is reduced.

According to the medicine area specifying method 2 described above, it is possible to perform the position specification with high accuracy without providing the backlight (transmission illumination). When the black dots are provided on the bottom portion of the first accommodating part 11, it is also possible to achieve the same effect by the above-described medicine area specifying method 1.

The adsorption/shutter mechanism 122 includes an adsorption mechanism that adsorbs the medicine specified as a target to be conveyed, and a shutter mechanism that prevents the medicine adsorbed by the adsorption mechanism from falling. The adsorption mechanism is provided so as to be movable in the Z-axis direction. The shutter mechanism is provided in front of the end portion so as to be movable substantially parallel with an XY plane.

When acquiring a medicine, the adsorption mechanism extends from the end portion, and then adsorbs the specified medicine at the tip portion thereof, and thereafter returns to the position of the end portion. In this state, the conveyance control part 61 moves the shutter mechanism to a position located opposite the end portion, and maintains the position of the shutter mechanism during conveying a medicine (referred to as a "closed state"). If the adsorption/shutter mechanism 122 is moved to a position opposed to a medicine placement table 133*a* of a medicine holding mechanism 133 disposed in the receiving area Ar1 (see (b) of FIG. 6), then the conveyance control part 61 moves the shutter mechanism to a position where the shutter mechanism does not face toward the end portion (referred to as an "open state"). Then, by extending the adsorption mechanism from the end portion and then releasing the adsorption state, the medicine is placed on the medicine placement table 133*a*.

In other words, in the process of conveying a medicine to the imaging unit 13, the adsorption mechanism is moved to the first accommodating part 11 at a position opposed to the first accommodating part 11 (specifically, the adsorption mechanism is moved from above the first accommodating part 11 to the inside of the first accommodating part 11), and adsorbs the medicine accommodated in the first accommodating part 11.

The adsorption mechanism has, for example, a configuration shown in FIG. 5. As shown in FIG. 5, the adsorption mechanism includes, at the tip portion thereof, an adsorption pad 122*a* that comes into contact with the medicine to be conveyed. The adsorption pad 122*a* is connected to a vacuum pump 122d that generates a vacuum (sucks air) through an air pipe 122b through which air flows.

In (a) of FIG. 5, a proportional control solenoid valve 122c for controlling the flow rate of the air flowing through the air pipe 122b is provided in the middle of the air pipe 122b. Further, in (b) of FIG. 5, a solenoid valve 122p and flow control valves 122q, 122r are provided instead of the proportional control solenoid valve 122c. Specifically, in the example shown in (b) of FIG. 5, a flow control valve 122q is provided in the middle of the air pipe 122b. Further, a branched air pipe 122b' branched from the air pipe 122b is provided, in order close to the air pipe 122b, with a solenoid valve 122p that controls the flow rate control valves 122q, 122r and a flow rate control valve 122r that controls the flow rate of the air flowing into the branched air pipe 122b'. It is possible to control the flow rate of the air flowing through the air pipe 122b by the proportional control solenoid valve 122c in (a) of FIG. 5. It is possible to control the flow rate of the air flowing through the air pipe 122b by the solenoid valve 122p and the flow rate control valves 122q, 122r in (b) of FIG. 5. Thus, it is possible to adjust a suction force (adsorption pressure) for adsorbing a medicine at the adsorption pad 122a. Further, (b) of FIG. 5 shows that the solenoid valve 122p is in an off state.

Here, when adsorbing a medicine by the adsorption pad 122a, it is necessary to increase the flow rate of air to generate a relatively strong suction force. When a plurality of medicines are simultaneously adsorbed by the adsorption pad 122a, it is necessary to detect that the suction force does not rise beyond a predetermined value notwithstanding the increase in the flow rate of air, and to attempt to adsorb the medicines again. Further, during adsorbing and conveying the medicine, it is necessary to maintain a relatively strong suction force by increasing the flow rate of air so that the medicines can be held even if the medicines are not in fully close contact with the adsorption pad 122a. It is necessary to control the flow rate of air in order to change the suction force as described above, but it is unnecessary to complicatedly control the flow rate of air to that extent.

In the case of (b) of FIG. 5, the flow rate of the air flowing through the air pipe 122b is switched to one of two flow rates, "high" and "low" by controlling the flow rate control valves 122q, 122r by using the solenoid valve 122p. Specifically, the flow rate of the air is reduced by turning on the solenoid valve 122p, and the flow rate of the air is increased by turning off the solenoid valve 122p. In this case, it is possible to simplify the flow rate control of the air, when compared with the case of the proportional control solenoid valve 122c in (a) of FIG. 5. Further, the control of the adsorption mechanism is performed by the conveyance control part 61 and the sorting control part 62.

Further, the conveyance control part 61 (the sorting control part 62 during sorting the medicines) may change the time to be spent from bringing the adsorption pad 122a into close contact with the medicine to pulling the tip portion upwards (lifting up the medicine) in accordance with the type of the medicine.

In this case, the conveyance control part 61 analyzes, for example, the medicine image captured by the second camera 121 to determine whether or not the size or shape of the medicine has difficulty in close contact with the adsorption pad 122a in comparison with the size of the adsorption pad 122a. When it is determined that the medicine has the size or shape that has difficulty in close contact, the conveyance control part 61 extends the time to be spent for pulling up the medicine by the tip portion by a predetermined time in comparison with the case where it is determined that the medicine easily comes into close contact. The medicine having difficulty in close contact may be pulled up immediately after adsorption. But, even if the suction force has reached a predetermined value sufficient for the pulling-up, there is a possibility that the medicine is not sufficiently adsorbed to the adsorption pad 122a and thus falls. By extending the time to be spent for pulling up the medicine by the tip portion by the predetermined time, it is possible to bring the medicine into sufficiently close contact with the adsorption pad 122a, and thus it is possible to prevent the medicine from falling when being pulled up.

Further, during adsorption in the first accommodating part 11, the conveyance control part 61 appropriately colors a medicine in the image, and determines the size of the medicine by comparing the size value of the area of the colored portion in the image with the size value of a set area.

The conveyance mechanism 123 moves the adsorption/shutter mechanism 122 in an X-axis direction and a Y-axis direction under the control of the conveyance control part 61. The conveyance mechanism 123 allows the adsorption/shutter mechanism 122 to be moved when searching for the medicine to be conveyed above the first accommodating part 11, or allows the medicine to be conveyed from the first accommodating part 11 to the medicine placement table 133a. Further, in a medicine sorting process to be described below, the conveyance mechanism allows the medicine to be conveyed from the medicine placement table 133a to the second accommodating part 14.

Further, the conveyance/sorting unit 12 may include, at the tip portion of the adsorption mechanism, a distance measurement sensor that detects (measures) a distance from the tip portion to a medicine (distance in the Z-axis direction). Further, the conveyance/sorting unit may include a pressure sensor that detects the suction force applied by the adsorption mechanism.

By measuring the distance in the Z-axis direction by the distance measurement sensor, the conveyance control part 61 can specify the exact position of a medicine regardless of the position of the second camera 121 with respect to the first accommodating part 11 and the accumulated state of the medicines in the first accommodating part 11.

The distance measurement sensor may measure the distance to a measuring target based on the average area of the captured images. In this case, the conveyance control part 61 lowers the tip portion within a range of the distance to the measurement target (average height) based on the average of the areas acquired by the distance measurement sensor. In the case where the pressure sensor is provided, it is possible to lower the tip portion so as not to pass the medicines accommodated in the first accommodating part 11 through a process to be described below.

Further, the distance measurement sensor may measure a distance to the vicinity of an apex of a pile of medicines formed by stacking the medicines in the first accommodating part 11. In this case, the conveyance control part 61 can lower the tip portion to a position immediately before the apex at a time based on the distance.

Further, the suction force detected by the pressure sensor changes depending upon whether or not an object exists in front of the tip portion. When the pressure sensor is provided, the conveyance control part 61 determines whether the tip portion is approaching the medicine based on the change in the suction force, and controls the movement of the adsorption mechanism in the Z-axis direction based on the determination result. For example, when the suction force changes as the tip portion approaches the medicine, by reducing the moving speed of the adsorption mechanism in the Z-axis direction, it is possible to prevent the medicines stacked in the first accommodating part 11 from collapsing due to the tip portion that collides with the medicines when adsorbing the medicine.

Further, for example, a threshold value set for the pressure sensor may be set in two stages. In case of one threshold value, the conveyance control part 61 (the sorting control part 62 at the time of medicine sorting) determines that the tip portion is located at an adsorbable position when the suction force becomes equal to or greater than the threshold value. However, since the moving speed of the tip portion is high, notwithstanding reducing the moving speed and stopping the tip portion is stopped after the determination, there is a possibility that the tip portion collides with medicines and collapse the medicines stacked in the first accommodating part 11.

Therefore, as the threshold value to be set in the pressure sensor, a first threshold value for determining whether or not an adsorption target such as a medicine exists in the vicinity of the tip portion, and a second threshold value for determining that a medicine is adsorbed to the tip portion are set. The first threshold value is smaller than the second threshold value, and is smaller than the threshold value in the case where one threshold value is set as described above. These two threshold values are set in advance through experiments or the like. When the tip portion is lowered and the medicine enters a predetermined range of the tip portion (within a range where the medicine can be adsorbed), a slight change occurs in the suction force (the suction force slightly increases). The first threshold value is set such that the suction force changing at this time can be detected. Further, when the medicine is adsorbed, a suction force larger than the changed suction force is generated. The second threshold value is set such that a high suction force at the time of the adsorption can be detected.

The conveyance control part 61 lowers the tip portion and starts suction by the vacuum pump 122d. When it is determined that the suction force detected by the pressure sensor is equal to or greater than the first threshold value, the conveyance control part 61 determines that the tip portion has approached the medicine to a position where the medicine can be adsorbed, and stops the tip portion. Thereafter, the conveyance control part 61 stands by for a predetermined time until the medicine closest to the tip portion is naturally adsorbed. If the medicine is adsorbed to the tip portion, the suction force increases more, and the changed suction force becomes equal to or greater than the second threshold value. When it is determined that the changed suction force becomes equal to or greater than the second threshold value, the conveyance control part 61 determines that the tip portion has adsorbed the medicine, raises the tip portion, and conveys the medicine to the next conveyance destination.

Further, when it is impossible to determine that the suction force becomes equal to or greater than the second threshold value within a predetermined time after stopping the tip portion, for example, the conveyance control part 61 may retry the medicine adsorption process by first raising the tip portion and then lowering the tip portion again. Further, in this case, the conveyance control part 61 may determine whether or not the suction force becomes equal to or greater than the second threshold value by lowering the tip portion by a predetermined distance (a distance in which the pile of medicines does not collapse, for example, about several millimeters) from the stopped position. In other words, the tip portion may be slightly lowered such that the medicine is adsorbed to the tip portion.

By setting the two-stage threshold values (particularly, the first threshold value) as described above, it is possible to reliably prevent the medicines stacked in the first accommodating part 11 from collapsing due to the tip portion during the adsorption of the medicine.

Further, when lowering the tip portion first, the conveyance control part 61 may lower the tip portion at a predetermined speed by a predetermined distance (e.g., to a position where the tip portion does not enter the first accommodating part 11) and may then decelerate the tip portion. Then, after the deceleration, the conveyance control part 61 may lower the tip portion until the suction force becomes equal to or greater than the first threshold value or the second threshold value. The aforesaid "lowering the tip portion first" means lowering the tip portion from the end portion of the housing, which includes at least the adsorption/shutter mechanism 122, on the side opposed to the pedestal 19. Further, when the suction force becomes equal to or greater than the second threshold value at a time, the conveyance control part 61 progresses to the conveyance process as it is.

[Medicine Imaging Process]

Figure 7:
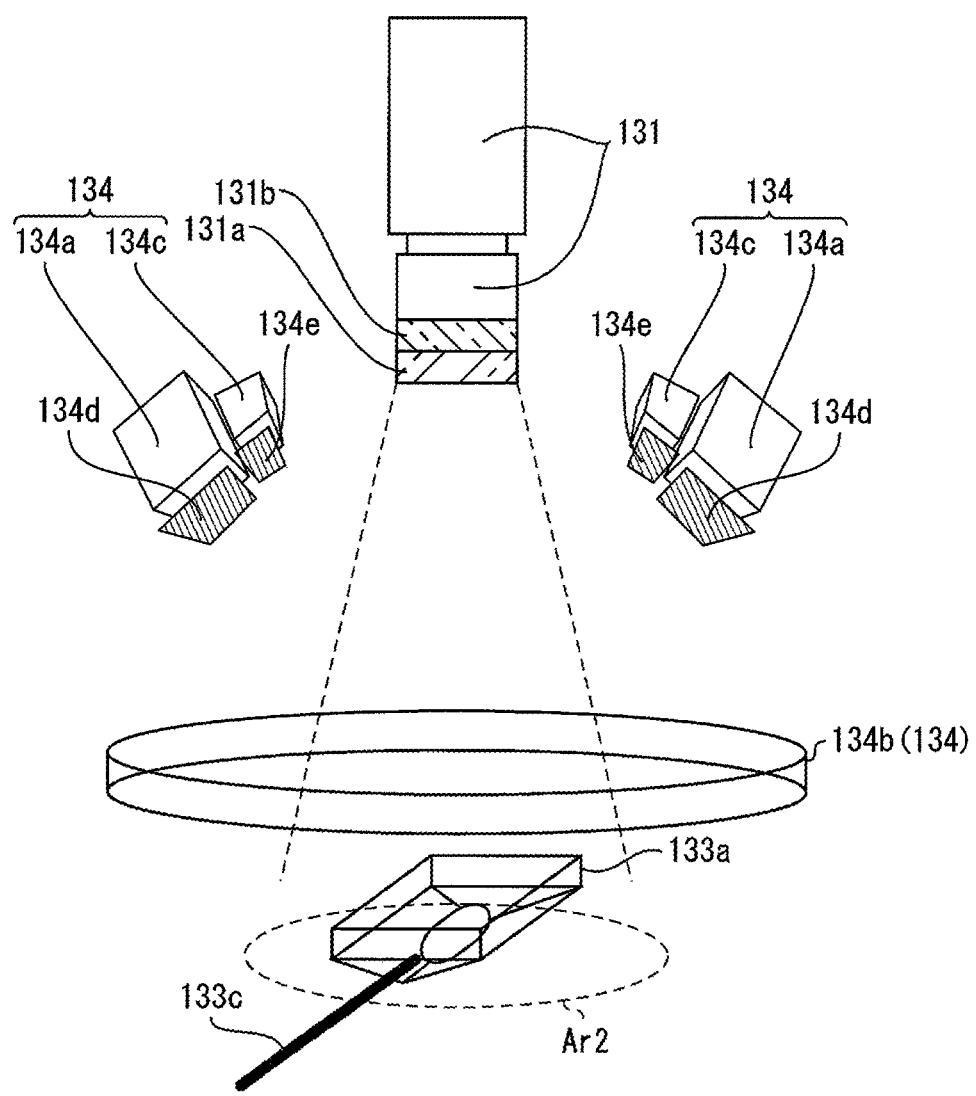
FIG. 7 is a view schematically showing the internal configuration of the imaging unit.
Figure 8:
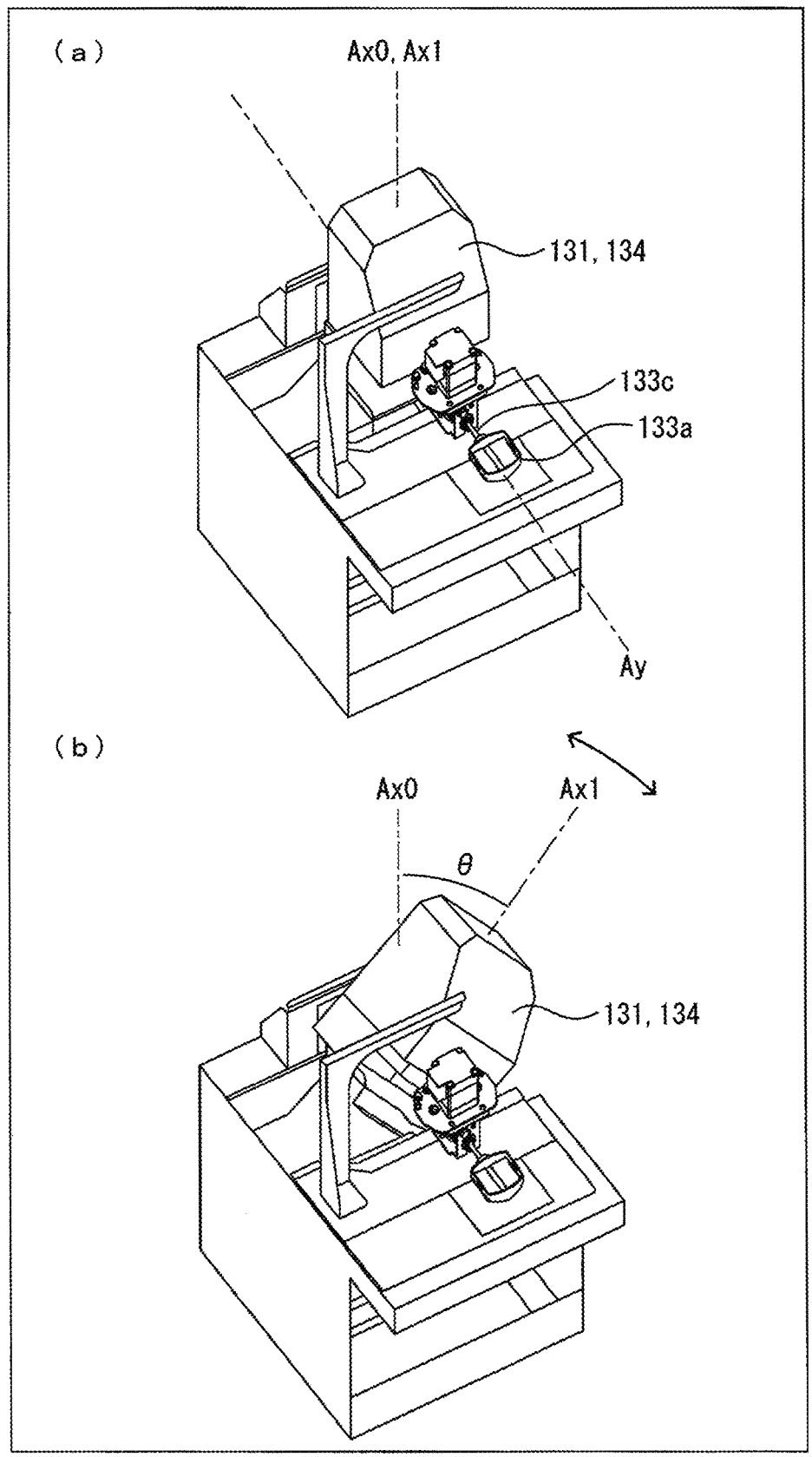
FIG. 8 ((a) and (b) of FIG. 8) is a view illustrating turning of the imaging unit.

Next, a medicine imaging process performed by the imaging unit 13 is described with reference to FIGS. 1, 3, and 6 to 8. In FIG. 6, (a) and (b) of FIG. 6 are perspective views showing the whole configuration of the imaging unit 13. FIG. 7 is a view schematically showing the internal configuration of the imaging unit 13. In FIG. 8, (a) and (b) of FIG. 8 are views illustrating the turning of the imaging unit 13. The medicine imaging process is mainly performed by the imaging unit 13 and the imaging control part 63.

Specifically, the imaging unit 13 images the medicine which is placed on the medicine placement table 133a and is disposed in a disposition area Ar2 where a medicine to be imaged is disposed. The disposition area Ar2 is shown in (b) of FIG. 6 and FIG. 7. The imaging control part 63 controls: the imaging process performed by the imaging unit 13; the turning movements of the first camera 131 and an illuminator 134; and the movement of the medicine holding mechanism 133. As shown in FIGS. 1 and 6, the imaging unit 13 includes the first camera 131 (an imaging part), a rotation mechanism 132 (a rotation part), a medicine holding mechanism 133 (a medicine placement table, a movement mechanism), and the illuminator 134 (an ultraviolet light radiation part, a visible light radiation part).

The first camera 131 images the medicine disposed in the disposition area Ar2 located opposite the first camera 131 in order to discriminate the type of the medicine in the discrimination part 64 to be described below. The medicine holding mechanism 133 is a mechanism for holding the medicine. As shown in (a) and (b) of FIG. 6, the medicine holding mechanism includes a medicine placement table 133a (a schale), a turning mechanism 133b (a movement mechanism), and a shaft portion 133c which connects the medicine placement table 133a and the turning mechanism 133b to each other. The medicine placement table 133a is used for placing a medicine to be imaged thereon. The turning mechanism 133b moves the medicine placement table 133a. Specifically, the turning mechanism 133b turns the medicine placement table 133a with respect to the XY plane, and turns the shaft portion 133c in a circumferential direction of the shaft portion 133c.

If a medicine conveyed from the first accommodating part 11 is placed on the medicine placement table 133a, then the imaging control part 63 drives the turning mechanism 133b to move the medicine placement table 133a from the receiving area Ar1 to the disposition area Ar2. Thereafter, the imaging control part controls at least the first camera 131 and the illuminator 134 to image the medicine placed in the disposition area Ar2. The captured image is stored in the storage part 80 as the image data. For example, after the imaging is completed, the imaging control part 63 drives the turning mechanism 133b to move the medicine placement table 133a, on which the imaged medicine is placed, from the disposition area Ar2 to the receiving area Ar1.

In other words, under the control of the imaging control part 63, the turning mechanism 133b moves the medicine placement table 133a from the receiving area Ar1 (a placement area), in which the medicine is placed, to the disposition area Ar2. Further, the turning mechanism 133b moves the medicine placement table 133a from the disposition area Ar2 to the receiving area Ar1 (a sorting standby area) again in order to waiting for sorting the medicine to the second accommodating part 14. In this embodiment, the receiving area Ar1 is used for both the function of the placement area in which the medicine is placed and the function of the sorting standby area for waiting for sorting, but the placement area and the sorting standby area may be at different positions of the pedestal 19, respectively.

In this embodiment, two medicine placement tables 133a are provided at a tip portion (an end portion) of the shaft portion 133c. By turning the shaft portion 133c, the turning mechanism 133b disposes one of the tablet placement tables 133a in the disposition area Ar2 and disposes the other of the medicine placement tables 133a in the receiving area Ar1 at that time. When the medicine is imaged in the disposition area Ar2, a continuous medicine imaging process is possible by conveying a medicine from the first accommodating part 11 to the medicine placement table 133a which exists in the receiving area Ar1 and placing the medicine on the medicine placement table 133a by the conveyance/sorting unit 12. Further, it is assumed that the medicine placement table 133a is in the state where no medicine is placed, such as after the medicine sorting process for the second accommodating part 14.

Further, in this embodiment, the medicine placement table 133a has transparency. Therefore, the first camera 131 can images the medicine placed on the medicine placement table 133a from various directions through the medicine placement table 133a.

Further, as shown in FIG. 7, the medicine placement table 133a may have a V-shaped cross section with a concave bottom portion. As shown in (b) of FIG. 6 and FIG. 7, when the medicine placement tables 133a are disposed in the receiving area Ar1 and the disposition area Ar2, a groove direction in the V-shaped cross section (an extension direction of the shaft portion 133c) is substantially parallel with a turning axis Ay (see (a) of FIG. 8) of an imaging mechanism (described below) by the rotation mechanism 132. Further, the V-shaped cross section of the bottom portion is not only an acute V shape, but also may be a shape enough for sufficiently recognizing information indicated by an engraving or print on the medicine (engraving information or print information) even when the medicine placement table 133a is viewed (imaged) from a back side thereof. Further, the V-shaped cross section of the bottom portion may be a shape enough for fixing the medicine thereon.

In case where the medicine is a capsule or a deformed tablet (e.g., a rugby-ball-shaped tablet), if the bottom portion of the medicine placement table 133a is flat, then the orientation of the medicine is not aligned on the XY plane and there is a possibility that it is difficult to acquire a clear medicine image (engraving information or print information). If the bottom portion has the V-shaped cross section, then a capsule or a deformed tablet is fitted to the lowermost end portion, and thus the medicine can be fixed. Therefore, a clear medicine image is easily acquired. Further, in case of a tablet, the medicine may be fixed, by, for example, turning the shaft portion 133c in the circumferential direction of shaft portion 133c and causing a planar portion of the medicine placement table 133a to be opposed to the first camera 131.

In addition, the turning mechanism 133b can vibrate (finely move or shake) the medicine placement table 133a. In this case, by applying vibration to the capsule placed on the medicine placement table 133a to roll the capsule, it is possible to allow the engraved or printed portion of the capsule to be oriented in a predetermined direction (e.g., it is possible to allow the portion to be opposed to the first camera 131 disposed at an initial position to be described below). Therefore, the imaging control part 63 can acquire a medicine image including an engraving or print by the first imaging of the medicine (before the turning of the first camera 131). Further, for example, even if a columnar tablet (having a circular bottom portion) is placed in the state of standing erect on said planar portion, the tablet can be laid sideways (can be disposed so that a bottom portion of the tablet faces the planar portion) due to the vibration.

Further, a black film may be provided along the periphery of the bottom portion of the medicine placement table 133a. In this case, it is possible to prevent the light radiated to the medicine during imaging from being reflected by the medicine placement table 133a.

Under the control of the imaging control part 63, the illuminator 134 emits light that is radiated to a medicine when the medicine is imaged. As shown in (a) of FIG. 6 and FIG. 7, the illuminator 134 includes a visible light radiation part (a first radiation part 134a and second radiation part 134b) that radiates visible light to a medicine, and an ultraviolet light radiation part 134c that radiates ultraviolet light to a medicine. The first radiation part 134a and the second radiation part 134b radiate white light to the medicine as the visible light. The first radiation part 134a is a bar-shaped visible light source (bar illumination), and the second radiation part 134b is a ring-shaped visible light source (ring illumination). The first camera 131 acquires an image based on visible light (visible light image) by receiving the visible light that is emitted from the first radiation part 134a or the second radiation part 134b and is reflected by the medicine. The imaging control part 63 outputs image data, which indicates the visible light image acquired by the first camera 131, to the discrimination part 64.

Here, the position where the first camera 131 is disposed so as to be opposed to the disposition area Ar2 is defined as an initial position. The initial position may be referred to a position that is above the disposition area Ar2 and is substantially perpendicular to the disposition area Ar2. In FIG. 6, FIG. 7 and (a) of FIG. 8, the first camera 131 exists at the initial position.

As shown in FIG. 7, at the initial position, the first radiation part 134a is provided obliquely above the medicine placement table 133a disposed in the disposition area Ar2. By disposing the first radiation part 134a as described above, it is possible to acquire a clear image of the print formed in the medicine.

Further, the second radiation part 134b is provided at a position closer than the first radiation part 134a. In the initial state, the second radiation part 134b radiates visible light to the medicine placement table 133a disposed in the disposition area Ar2 from a direction closer to the horizontal direction than the first radiation part 134a. By disposing the second radiation part 134b as described above, it is possible to acquire a clear image of the engraving (unevenness) engraved to medicine.

The ultraviolet light radiation part 134c excites components contained in the medicine by radiating ultraviolet light (e.g., light having a peak wavelength of 365 nm to 410 nm) to the medicine. By doing so, fluorescence (e.g., light having a peak wavelength of 410 nm to 800 nm) is extracted from the medicine. Therefore, the ultraviolet light radiation part 134c may be referred to as an excitation light source that emits excitation light for exciting the medicine.

The first camera 131 acquires an image based on ultraviolet light (ultraviolet light image) by receiving the fluorescence emitting from the medicine. The imaging control part 63 outputs the image data, which indicates the visible light image acquired by the first camera 131, to the discrimination part 64. Therefore, the discrimination part 64 to be described below can discriminate the type of the medicine by using both the ultraviolet light image and the visible light image.

In this embodiment, the ultraviolet light radiation part 134c is provided at a position adjacent to the first radiation part 134a. The disposition position of the ultraviolet light radiation part 134c is not limited to a particular position as long as the ultraviolet light can be radiated to the medicine and the fluorescence can be efficiently extracted.

Further, as shown in FIG. 7, a polarization filter (PL filter) 131a and an ultraviolet light removal filter 131b are provided in front of a lens of the first camera 131. The polarization filter 131a removes light unnecessary for imaging (e.g., light reflected from the medicine placement table 133a) from light directed toward the first camera 131. The ultraviolet light removal filter 131b removes ultraviolet light directed to the first camera 131, for example, ultraviolet light that emits from the ultraviolet light radiation part 134c and is reflected by the medicine without excitation. Further, a polarization filter 134d, which only transmits visible light toward the medicine and removes other unnecessary light, is provided in front of the first radiation part 134a. Furthermore, an ultraviolet light transmission filter 134e, which that transmits only ultraviolet light toward the medicine and removes other unnecessary light (e.g., visible light), is provided in front of the ultraviolet light radiation part 134c.

As shown in FIG. 6, the rotation mechanism 132 rotates the first camera 131 such that the first camera turns around the disposition area Ar2 where a medicine to be imaged is disposed (the medicine placement table 133a disposed at the position). The first camera 131 images the medicine disposed in the disposition area Ar2 from a plurality of positions where the first camera 131 is rotated by the rotation mechanism 132. Specifically, the imaging mechanism including the first camera 131 and the illuminator 134 is rotated so as to turn around the disposition area Ar2. Therefore, the first camera 131 can image the medicine from a plurality of directions while maintaining the positional relationship between the first camera 131 and the illuminator 134 with respect to the disposition area Ar2.

As shown in (a) of FIG. 6, the rotation mechanism 132 includes an imaging mechanism driving part 132a and a power transmitting mechanism 132b. The imaging mechanism driving part 132a generates power for turning the imaging mechanism around the disposition area Ar2. The power transmitting mechanism 132b transmits the power generated by the imaging mechanism driving part 132a to the imaging mechanism. The imaging mechanism driving part 132a is driven by the control of the imaging control part 63, and changes the position of the imaging mechanism around the disposition area Ar2.

The rotation mechanism 132 rotates the imaging mechanism between an initial position and a position opposed to the initial position. The position opposed to the initial position is a position that is substantially perpendicular to the disposition area Ar2 and is below the disposition area Ar2. Further, the position opposed to the initial position may be referred to as a position at which the first camera 131 is opposed to the bottom portion of the medicine placement table 133a existing in the disposition area Ar2.

As shown in FIG. 8, an axis passing through a center of the disposition area Ar2 and parallel to the Z axis is referred to as an axis Ax0, and an axis passing through the center of the disposition area Ar2 and a center of the imaging mechanism is referred to as an axis Ax1. Further, an angle formed by the axis Ax0 and the axis Ax1 is referred to as θ. In this embodiment, the rotation mechanism 132 disposes the imaging mechanism at any one of the positions θ=0° (initial position), 45°, 135°, and 180°. It is shown in (a) of FIG. 8 the case where the imaging mechanism is located at the position of θ=0°. It is shown in (b) of FIG. 8 the case where the imaging mechanism turns from the initial position and is located at the position of θ=45°.

By turning the imaging mechanism around the disposition area Ar2 as described above, it is possible to image the medicine from a plurality of directions in the state where the medicine is fixed to the disposition area Ar2. Further, even when the medicine (tablet) stands erect notwithstanding shaking medicine placement table 133a, it is possible to acquire information indicating the engraving engraved to the medicine due to imaging from an oblique direction (θ=45° or 135°).

Further, the medicine may be imaged from a plurality of directions by fixing the imaging mechanism and rotating the medicine. Further, it is possible to make the fixed imaging mechanism obtain the engraved or printed portion by vibrating the medicine placement table 133a by the turning mechanism 133b and rolling the medicine on the medicine placement table 133a as described above. Further, the configuration for imaging the medicine from a plurality of direction may include the following (A) to (C). (A) Above the disposition area Ar2 is disposed (fixed) a set including the following: the first camera 131 provided at the position opposed to the disposition area Ar2; and the first radiation part 134a and the ultraviolet light radiation part 134c provided obliquely above the medicine placement table 133a disposed in the disposition area Ar2. In other words, this set is fixed at the position shown in FIG. 7. (B) Below the disposition area Ar2 is disposed (fixed) a set including the following: the first camera 131 provided at the position opposed to the disposition area Ar2; and the first radiation part 134a and the ultraviolet light radiation part 134c provided obliquely below the medicine placement table 133a disposed in the disposition area Ar2. In other words, this set is fixed at a position opposed to the set (A) with the disposition area Ar2 interposed therebetween. (C) The second radiation part 134b is provided in the vicinity of the medicine placement table 133a disposed in the disposition area Ar2, as shown in FIG. 7.

(Imaging Position Control)

Next, an example of position control of the imaging mechanism is described. The imaging control part 63 first sets the imaging mechanism to the initial position, and causes the first camera 131 to image a medicine placed in the disposition area Ar2 at the initial position. At this time, the first camera 131 acquires visible light image (two visible light images) based on the visible light from the first radiation part 134*a* and the second radiation part 134*b*, and acquires an ultralight light image based on the ultraviolet light from the ultraviolet light radiation part 134*c*.

Next, the imaging control part 63 sets the imaging mechanism to the position opposed to the initial position, and causes the first camera 131 to image the medicine disposed in the disposition area Ar2 at the position so as to acquire two visible light images and an ultraviolet light image. The discrimination part 64 discriminates the type of the medicine by analyzing these six images. When it is impossible to specify the type of the medicine as one type, the imaging control part 63 causes the first radiation part 134*a* and the second radiation part 134*b* to emit visible light at the positions of θ=45° and 135°, and causes the first camera 131 to image the medicine. The discrimination part 64 discriminates the type of the medicine by analyzing the visible light image at this time.

There may be various methods for controlling the position of the imaging mechanism without being limited to the foregoing. For example, imaging may be performed from the position opposed to the initial position and thereafter imaging may be performed from the initial position. Further, a medicine discrimination process may be performed based on the visible light image captured from the position of θ=45°, and, only when it is impossible to specify the type of the medicine as one type, the visible light image captured from the position of θ=135° may be acquired. Further, only the ultraviolet light images may be acquired at the initial position and the position opposed to the initial position, and, after performing the medicine discrimination process based on such ultraviolet light images, visible light images may be acquired at the position. Further, visible light images and ultraviolet light images may be acquired at all the positions.

[Image Process/Discrimination Process]

Next, an image process for the image captured by the imaging unit 13 and a medicine discrimination process based on the result of the image process are described with reference to FIG. 1. The image process is mainly performed by the imaging control part 63, and the discrimination process is mainly performed by the discrimination part 64.

The discrimination part 64 discriminates the type of a medicine based on the image of the medicine imaged by the first camera 131. Specifically, the discrimination part 64 discriminates the type of the medicine based on an imaging result (visible light image) of the medicine imaged in the state where visible light is radiated from the first radiation part 134*a* or the second radiation part 134*b*. Further, the discrimination part 64 discriminates the type of the medicine based on an imaging result (ultraviolet light image) of the medicine imaged in the state where ultraviolet light is radiated.

The discrimination part 64 performs image analysis on each of the visible light image and/or the ultraviolet light image, thereby extracting the features of the medicine included in the image. In other words, the discrimination part 64 has a function of a feature extraction part that extracts the features of the medicine. Examples of the features of a medicine include a size, a shape, an engraving, a print, a dividing line, and a representative color (the color of the engraved or printed area). When optical character recognition (OCR) or the like is performed, as the features of a medicine, identification information indicating the medicine name or manufacturer represented by an engraving or a print, and other information such as a use period are extracted. Further, in the case of an ultraviolet light image, the feature of a medicine may be, for example, a representative color of the medicine in the image. The discrimination part 64 stores the extracted features of each medicine in the storage part 80 in association with the image data of the medicine. The feature extraction of a medicine may be performed by a known technique.

The discrimination part 64 discriminates the type of a medicine by collating the features of each medicine with the medicine database. In other words, the discrimination part 64 has a function of a medicine data extraction part that narrows down medicine data candidates related to the imaged medicine from the medicine database by using pattern matching or the like based on the extracted features of the medicine. In this case, for example, the medicine data candidates are narrowed down by using at least one of the above-described size, shape, engraving, print, dividing line, and representative color. Thereafter, the discrimination part 64 performs OCR or the like, reads the identification information indicated by the engraving or print, and further narrows down the type of the medicine from the candidates by using pattern matching or the like.

Further, the discrimination part 64 compares the feature of each medicine with one another and discriminates the type of the medicine based on whether or not the features of medicines are regarded as the same. In other words, the discrimination part 64 has a function of a collation part that collates the extracted medicine features (target feature) with the medicine features having been extracted by that time (collation feature) by using pattern matching or the like and discriminates the type of the medicine based on the collation result. Further, at least one of the above-described features may be collated as a target feature and a collation feature.

Specifically, when the image of a medicine sorted into the sorting cup 141 by a medicine sorting process to be described below is used as a reference image, the medicine features included in an image acquired thereafter (target feature) are compared with the medicine features included in a reference images (collation feature). When the medicine is sorted into the sorting cup 141 based on the collation result, the image of such a medicine also becomes a reference image. In this manner, the discrimination part 64 uses the image of the sorted medicine as the reference image, and compares the features of the image of the medicine imaged thereafter with the features of the medicine in the reference image. Therefore, since the above-described collation can be performed by using the reference image instead of the medicine database, it is possible to perform a medicine sorting process for the sorting cup 141 even if a medicine is not pre-registered in the medicine database.

Further, the first medicine (sorting target) or a medicine (sorting target) that does not match the features of the reference image is sorted into the sorting cup 141, for example, when the feature of the sorting target is determined to be the feature of a medicine (in case of an estimated medicine to be described below). Further, the sorting target may be sorted into the sorting cup 141 based on the result of comparing the feature thereof with the feature of a medicine included database related to a predetermined number of medicines.

In the narrowing-down described above, the discrimination part 64 also uses the analysis result of an ultraviolet light image. Here, when the analysis result of an ultraviolet light image is not used and when it is impossible to acquire a clear image of an engraving or print formed in a medicine, the type is discriminated based on the color, size, shape, or the like of the medicine. In this case, medicines having the same color (e.g., white color) and having almost the same size or shape may be determined to be the same type. The discrimination made in this manner increases the burden of a task for checking whether the medicines are the same type in subsequent visual inspection.

The discrimination part 64 discriminates the type of a medicine by using the fact that the fluorescence emitted from a medicine due to the radiation of ultraviolet light varies depending upon the components of the medicine. Therefore, it is possible to accurately discriminate medicines as different medicines when the components of the medicines are different from each other even if the medicines have the same color, size, and shape. Since the components of medicines are unique to each medicine, it is possible to narrow down and discriminate candidates more accurately by using the analysis result of an ultraviolet light image than the narrowing-down using only a visible light image.

Therefore, as a first step in narrowing down the candidates, it is preferable that the discrimination part 64 performs narrowing-down of the candidates by comparing an analysis result of the ultraviolet light image (a representative color of a medicine) with the representative color of each medicine included in the medicine data base, which is obtained when ultraviolet light is radiated to the medicine). First, based on the fact that the medicine emits fluorescence due to the radiation of ultraviolet light, the discrimination part 64 specifies the medicine included in the ultraviolet light image by extracting the contour of a medicine in the an ultraviolet light image (the contour of an area whose brightness differs from that of the surroundings due to the fluorescence) Thereafter, the candidates are narrowed down by comparing the representative color of the medicine specified in the ultraviolet light image with the representative colors of the medicine database.

In this case, since the number of the candidates after narrowing-down is expected to be smaller than that in the case of not using the ultraviolet light image, it is possible to perform collation by using other features for a small number of the candidates. Therefore, it is possible to enhance the accuracy of collation. Further, if the number of the candidates is reduced, it may be possible to discriminate the type of a medicine without specifying identification information or the like through OCR or the like. In this case, it is possible to reduce the load of the image process. In particular, in case of a transparent medicine, in the visible light image, it is difficult to distinguish between the medicine included in the visible light image and the medicine placement table 133*a* (background). Therefore, it is impossible to extract the contour (area) of the medicine, and it becomes difficult to extract the features of the transparent medicine. Further, in case of using the ultraviolet light image as described above, it is possible to extract the contour of a medicine due to the emission of fluorescence even for a transparent medicine. Therefore, even if a medicine is a transparent medicine, it is possible to extract the features thereof.

The types of returned medicines are various unlike medicines used for dispensing, and the number thereof is huge. Therefore, accurate discrimination of the type of a medicine is a very important factor in view of the task burden in later visual inspection. And, by improving the performance of the discrimination process on the type of a medicine as described above, it is possible to rapidly sort a huge amount of medicines.

Further, in collation between the features, the discrimination part 64 may determine whether or not the features are regarded as the same in the same processing order as when the medicine database is used, and may narrow down the medicine data corresponding to the target features.

Further, the discrimination part 64 may perform collation between features and collation using the medicine database in parallel, or may perform the collation as follows. For example, the discrimination part 64 collates the extracted features of a medicine with the medicine database, and determines whether or not a candidate of the medicine data related to the imaged medicine exists in the medicine database based on the features. When it is determined that the candidate does not exist in the medicine database, the discrimination part 64 may discriminate the type of the medicine by collating the target features with the collation features.

Further, the discrimination part 64 may extract a plurality of pieces of color data of a medicine, as the features of the medicine, from each visible light image and each ultraviolet light image of the medicine imaged from a plurality of directions, and may narrow down the candidates. In this case, the discrimination part 64 compares a plurality of pieces of color data with, for example, the representative color included in the medicine database (in other words, performs color matching). In the case of the visible light image, it is compared with the representative color obtained by the radiation of visible light in the medicine database. In the case of the ultraviolet light image, it is compared with the representative color obtained by the radiation of ultraviolet light is radiated in the medicine database. Further, it may be compared with color data extracted as the collation features.

Further, when a logo indicating a manufacturer of ae medicine is attached to the medicine, the logo becomes the feature of the medicine as identification information. Therefore, in this case, the discrimination part 64 discriminates the type of the medicine by using the logo. Since the logo is attached to the medicine as an engraving or print, the discrimination part 64 acquires the logo by analyzing a visible light image. Further, regarding the logo, the discrimination part 64 may narrow down the candidates by collating the target features with the medicine database or the collation features by using artificial intelligence (machine learning, particularly deep learning).

In this case, after the candidates are narrowed down based on an ultraviolet light image, the discrimination part 64 may narrow down the candidates through the collation using artificial intelligence in respect to the logo, in addition to the narrowing-down of the candidates through the collation of the target features other than the logo with the medicine database or the collation features using pattern matching. Specifically, in case of deep learning, a neural network for deep learning is made to learn a multi-class classification problem by using images of medicines in which an engraving or print indicating logos of major manufacturers (a plurality of types of logos with different sizes, shapes, colors, and the like) are formed. For example, when the number of the manufacturers is twenty, the multi-class classification problem becomes a 20-class classification problem.

In general, a logo is frequently changed in terms of the size (in case of a character, font), shape, color, etc., emphasizing the legibility thereof. For this reason, there is a possibility that logos having different sizes may be attached the same type of medicines depending upon the timing for sale of the medicines. Further, the sizes of logos attached to capsules and tablets may differ from one another even if the manufacturers thereof are the same. Therefore, the same type of the logos of the same manufacturer may not be discriminated as the same even if the target features for a logo are collated with the medicine database or the collation features by using pattern matching or the like. This is because the logo may be different from a logo registered in the medicine database or a logo of the collation features in terms of size or the like.

Unlike the case of pattern matching, the discrimination part 64 can learn a logo feature extraction method by using artificial intelligence in logo collation as described above. Therefore, it is possible to perform a robust matching process in spite of variation in size, shape, color, illumination condition, or the like. Thus, the logos, which cannot be discriminated as the same through pattern matching, can be discriminated to be the same. Thus, the accuracy of the logo collation can be improved, and the candidate narrowing-down performance can be improved thereby. Further, by accumulating the extracted logo features (image data) and using them for the aforesaid learning, it is possible to further improve the accuracy of collation using artificial intelligence.

Further, even if the target features do not exist in the medicine database and are not regarded as the same as the collation features, the discrimination part 64 discriminates the type of a medicine as an estimated medicine when the target features are estimated as a medicine (tablet or capsule) based on at least some of the target features. In this case, the estimated medicine may be used as a target to be sorted into the second accommodating part 14 or the standby tray 15.

The discrimination part 64 outputs the discrimination result of the type of a medicine to the sorting control part 62. For example, when it is possible to specify a medicine as one type, or when the number of candidates is narrowed down to a predetermined number or less, medicine data related to the medicine is output as a discrimination result. In this case, the discrimination part 64 stores the medicine data related to the medicine in the storage part 80 in association with the image data of the medicine.

Further, the discrimination part 64 acquires a discrimination result by performing control such that the number of candidates does not exceed a predetermined number. For example, the discrimination part 64 sets the predetermined number (e.g., five) as a threshold value, and determines whether or not the number of the narrowed-down candidates exceeds the threshold value. When it is determined that the number of candidates exceeds the threshold value, the discrimination part 64 ranks a plurality of the candidates in the order similar to that of the features of the medicine to be discriminated. Then, the discrimination part extracts the candidates corresponding to the number set as the threshold value from a high rank (e.g., high-ranked five candidates), and outputs the medicine data related to the medicines of the candidates as a discrimination result. The similarity order is determined depending upon, for example, how many the number of matching features is. Alternatively, allocating a weighting may be given to each feature, and the similarity order may be determined from the degree of matching of each feature under consideration of the weighting.

When the type of a medicine is discriminated as an estimated medicine, the discrimination part 64 outputs the features of the medicine (the features of an object estimated as the estimated medicine) as a discrimination result. Further, when an object accommodated in the first accommodating part 11 is discriminated as a foreign matter other than a medicine, the discrimination part 64 outputs a discrimination result indicating that it is impossible to determine the type of the medicine.

Further, after the discrimination part 64 discriminates and determines the type of a medicine, the imaging control part 63 acquires a visible light image of the medicine placement table 133a including the medicine by the first camera 131, and stores image data thereof in the storage part 80. Visible light images are, for example, an image including an engraved or printed surface of a medicine, and an image including a surface of the opposite side. These visible light images are included in the data related to a medicine and written in the sorting cup 141, and become a display target to be displayed by the display control part 67 (see (b) of FIG. 11).

[Image Classification Process]

Next, an image classification process based on the results of the discrimination process is described with reference to FIG. 1. The image classification process is mainly performed by the image classification part 65.

The image classification part 65 classifies the images captured by the first camera 131 for each type of medicines discriminated by the discrimination part 64. Upon receiving the discrimination result from the discrimination part 64, the image classification part 65 performs the classification by determining whether or not the same discrimination result as the discrimination result made by the discrimination part 64 is stored in the storage part 80. For example, if the same determination result is not stored, the image classification part newly creates a storage area for the determination result, and stores, in the storage area, the image data in which the type of a medicine is discriminated. For example, if the same determination result is stored, the image classification part stores, in the storage are of the discrimination result, the image data in which the type of a medicine is discriminated.

The image classification part 65 assigns a name (assumed name) to the storage area whenever the storage area is created. As this name, for example, a medicine name, which is specified based on the discrimination result of the discrimination part 64 (the medicine name ranked first in the similarity order when there are a plurality of candidates), is assigned. In the case of an estimated medicine, the indication that it is an estimated medicine is assigned. The name of each storage area is changed to a medicine name uniquely specified at the time of visual inspection.

Further, where there are a plurality of medicine data candidates for the medicine to be discriminated as a result of the discrimination by the discrimination part 64, if the plurality of pieces of image data match all the plurality of pieces of stored medicine data of each medicine, the image classification part 65 may determine that the two determination results are the same. Further, when a medicine is discriminated as an estimated medicine, if the features of the estimated medicine match all the plurality of stored features corresponding one medicine, the two determination results may be determined to be the same.

As described above, by providing the image classification part 65, it is possible to classify the image data of the medicines so as to match the sorting result in the medicine sorting process to be described below. Therefore, the user can identify whether or not a plurality of medicines sorted into any sorting cup 141 are the same type by looking at each image data included in the classified image data group.

[Medicine Sorting Process]

Figure 9:
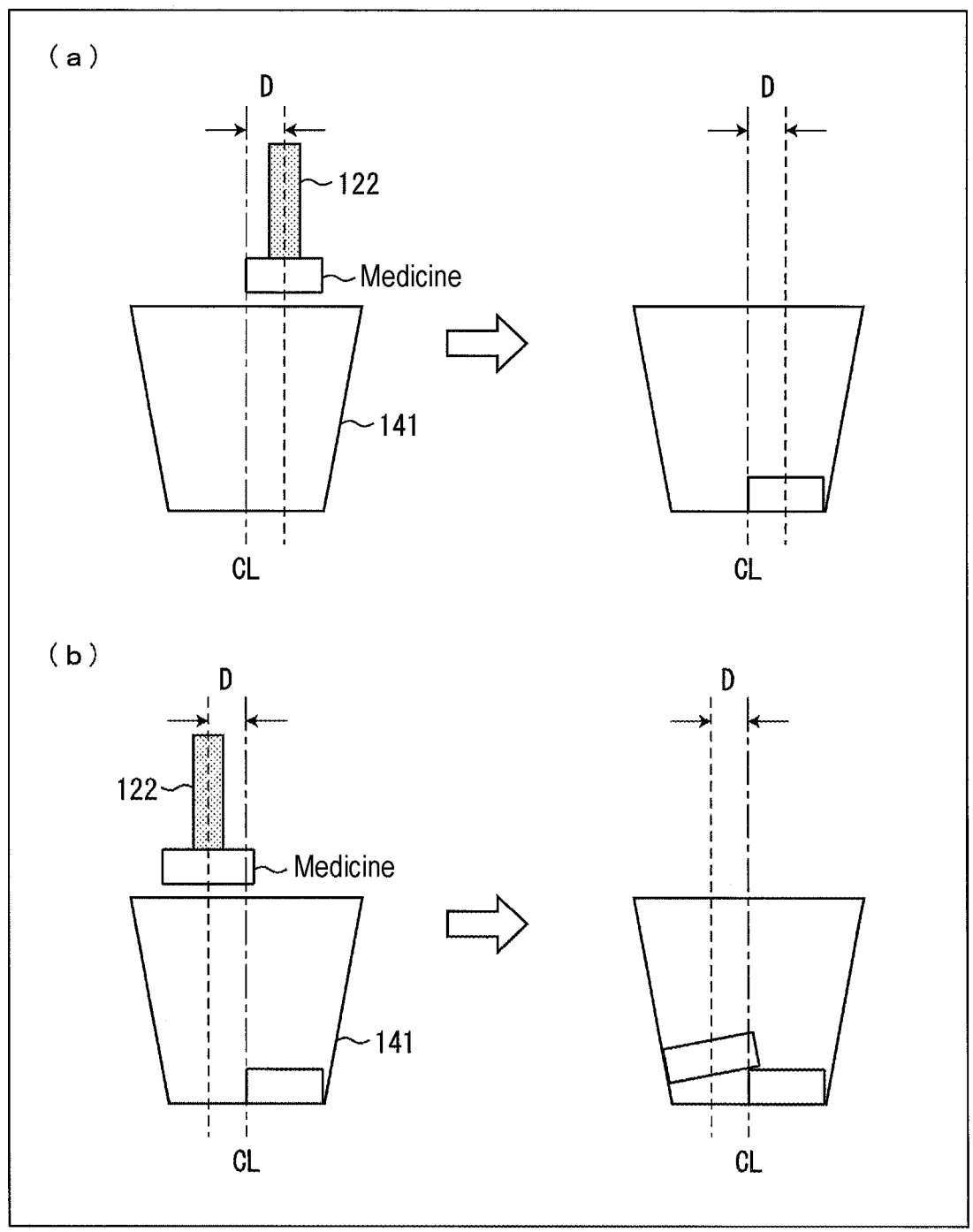
FIG. 9 ((a) and (b) of FIG. 9) is a view illustrating a sorting process for a sorting cup provided in the medicine sorting unit.
Figure 10:
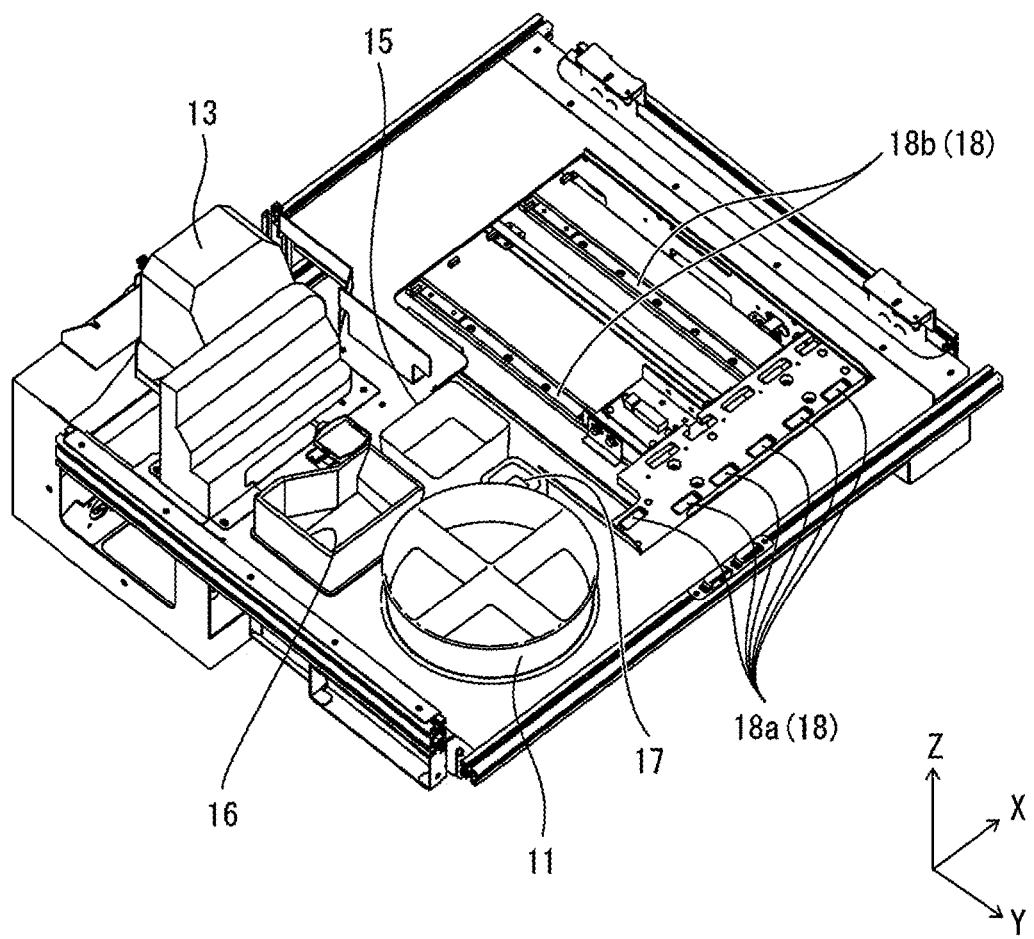
FIG. 10 is a perspective view showing a disposition of a second RFID reader/writer unit provided in the medicine sorting device.

Next, a medicine sorting process based on the results of the discrimination process is described with reference to FIGS. 1, 9, and 10. In FIG. 9, (a) and (b) of FIG. 9 are views illustrating a sorting process to a sorting cup 141. FIG. 10 is a perspective view showing a disposition of a second RFID reader/writer unit 18. The medicine sorting process is mainly performed by the conveyance/sorting unit 12 and the sorting control part 62.

The conveyance/sorting unit 12 sorts medicines by each type based on the discrimination result by the discrimination part 64, and stores them in the second accommodating part 14 or the standby tray 15. The sorting control part 62 controls the conveyance/sorting unit 12 such that the medicines disposed in the receiving area Ar1 after the imaging and discrimination processes are conveyed to a predetermined sorting cup 141 or a standby tray 15 of the second accommodating part 14 based on the discrimination result.

Upon receiving the discrimination result of a medicine, the sorting control part 62 determines the sorting position for storing the medicine, and stores the discrimination result and the determined sorting position in the storage part 80 in association with each other. Specifically, the sorting control part 62 determines whether or not the same discrimination result as the above discrimination result is stored in the storage part 80. Since the method of determining whether or not these two discrimination results are the same has been described in the above [Image classification process] section, a description thereof is omitted.

When the same discrimination result as the above discrimination result is stored, a sorting cup 141 associated with the stored discrimination result is determined as a sorting position. When the sorting position associated with the stored discrimination result is the standby tray 15, the standby tray 15 is determined as a sorting position. Further, when the same discrimination result as the above discrimination result is not stored, a sorting cup 141 in which no medicine is stored (a sorting cup 141 that is not determined as a sorting position) is determined as a sorting position. When the medicines are stored in all the sorting cups 141, the standby tray 15 is determined as a sorting position If the sorting position is determined, like the conveyance control part 61, the sorting control part 62 controls the conveyance mechanism 123 to move the conveyance/sorting unit 12 above the receiving area Ar1. Like the conveyance control part 61, the sorting control part 62 controls the second camera 121 and the adsorption/shutter mechanism 122 to adsorb a medicine disposed in the receiving area Ar1. Thereafter, the medicine is conveyed to the determined sorting cup 141 or the determined standby tray 15 by the conveyance mechanism 123. Since the shutter mechanism is in the closed state during conveying the medicine as described above, it is possible to prevent the medicine from falling into an area other than the determined sorting position (e.g., a sorting cup 141 other than the determined sorting cup 141). After conveyance, the medicine is stored in the sorting cup 141 or the standby tray 15 by releasing the adsorption. Further, the sorting control part 62 counts the number of medicines stored in the sorting cup 141 and stores it in the storage part 80 in association with the sorting position.

After the sorting control part 62 conveys a medicine on the medicine placement table 133a disposed in the receiving area Ar1 (a medicine after completion of discrimination) to the sorting position, the conveyance control part 61 controls the conveyance/sorting unit 12 to convey the medicine accommodated in the first accommodating part 11 to the empty medicine placement table 133a and to place the medicine on the empty medicine placement table 133a. Thus, the medicine sorting device 1 can continuously discriminate the types of medicines.

Further, when target features and collation features are collated by the discrimination part 64, the sorting control part 62 may determine the sorting position based on the collation result of the discrimination part 64. Specifically, when the discrimination part 64 determines that target features match collation features, the sorting control part 62 conveys the medicine having the target features to the same position as the position where the medicine having the collation features is sorted. Further, when it is determined that the target features and the collation features do not match, the sorting control part 62 conveys the medicine having the target features to a new position different from the position where a medicine having the collation features have already been sorted before sorting the medicine.

Further, upon receiving the discrimination result indicating that it is impossible to discriminate the type of a medicine, since an object placed in the receiving area Ar1 after the discrimination is a foreign matter, the sorting control part 62 conveys the foreign matter to the recovery tray 16.

In this manner, the sorting control part 62 does not follow the discrimination result of the type of a medicine, and stores all the objects accommodated in the first accommodating part 11 in one of the second accommodating part 14, the standby tray 15, or the recovery tray 16. Therefore, when it is impossible to specify a medicine as one type, or even when a foreign matter is mixed into the first accommodating part 11, it is possible to allow the sorting process to continue without stopping for that reason.

Further, to take out a medicine for which the discrimination process has been completed from the medicine placement table 133a disposed in the receiving area Ar1, the sorting control part 62 causes the second camera 121 to image the medicine placement table 133a and narrows down the positions of the medicine. Further, to take out a medicine from a sorting cup 141 when conveying the medicine stored in the sorting cup 141 to the packaging mechanism 6, the sorting control part 62 causes the second camera 121 to image the sorting cup 141 and narrows down medicines to be conveyed.

Further, when medicines are stored up to the upper limit of the number of medicines stored in a sorting cup 141, the sorting control part 62 stores medicines to be stored in an empty sorting cup 141 different from the above sorting cup 141 even if the type of medicines to be sorted is the same as the type of the medicines sorted into the above sorting cup 141.

Further, the sorting control part 62 performs, for example, a process as shown in FIG. 9, so that more medicines can be placed in a sorting cup 141. As shown in (a) of FIG. 9, the sorting control part 62 determines a position where a medicine is to be stored in the sorting cup 141 as a position deviated in a horizontal direction from a reference position of a sorting cup 141 (here, a center line CL) by a predetermined distance D, and places a medicine at that position. Further, when a next medicine is stored in the sorting cup 141, as shown in (b) of FIG. 9, the sorting control part 62 determines a position where the next medicine is to be stored as a position deviated in a direction opposite to the case of (a) of FIG. 9 from the reference position by a predetermined distance D, and places the medicine at that position.

The predetermined distance D (the amount of movement from the reference position) is calculated such that medicines are stored in the sorting cup 141 based on the maximum length of a medicine which can be acquired by imaging, and based on a width of the sorting cup 141 in the deviated direction. For example, when the maximum length of a medicine is large, the amount of movement is calculated to be smaller than that of a small medicine.

By controlling the storage position of the medicines in the sorting cup 141 in this manner, for example, when medicines are stacked along the center line CL, it is possible to prevent the stacked medicines from collapsing and rolling out of the sorting cup 141. Moreover, it is possible to prevent the tip portion of the adsorption mechanism of the adsorption/shutter mechanism 122 from colliding with the stacked medicines.

Further, the medicine data related to the medicines stored in a sorting cup 141 by the sorting control part 62 is stored in an RFID tag provided in the sorting cup 141 by the second RFID reader/writer unit 18.

Like the first RFID reader/writer unit 5, the second RFID reader/writer unit 18 writes medicine data to the RFID tag or reads medicine data stored in the RFID tag. Whenever a medicine is stored in a sorting cup 141, the sorting control part 62 writes data related to the medicine to the RFID control part 68.

The second RFID reader/writer unit 18 is provided below the second accommodating part 14. Specifically, as shown in FIG. 10, the second RFID reader/writer unit is provided so as to face toward the bottom portion of each sorting cup 141 when reading or writing the data related to medicines stored in the RFID tag of each sorting cup 141. In this embodiment, the second RFID reader/writer unit 18 includes a plurality of RFID reader/writers 18a juxtaposed in the X-axis direction, and is configured to be movable in the Y-axis direction by a guide member 18b extending in the Y-axis direction. This enables the second RFID reader/writer unit 18 to communication with the RFID tag of each sorting cup 141, and enables, for example, the medicine-related data written during the medicine sorting process to be used in a subsequent process.

[Display Process]

Figure 11:
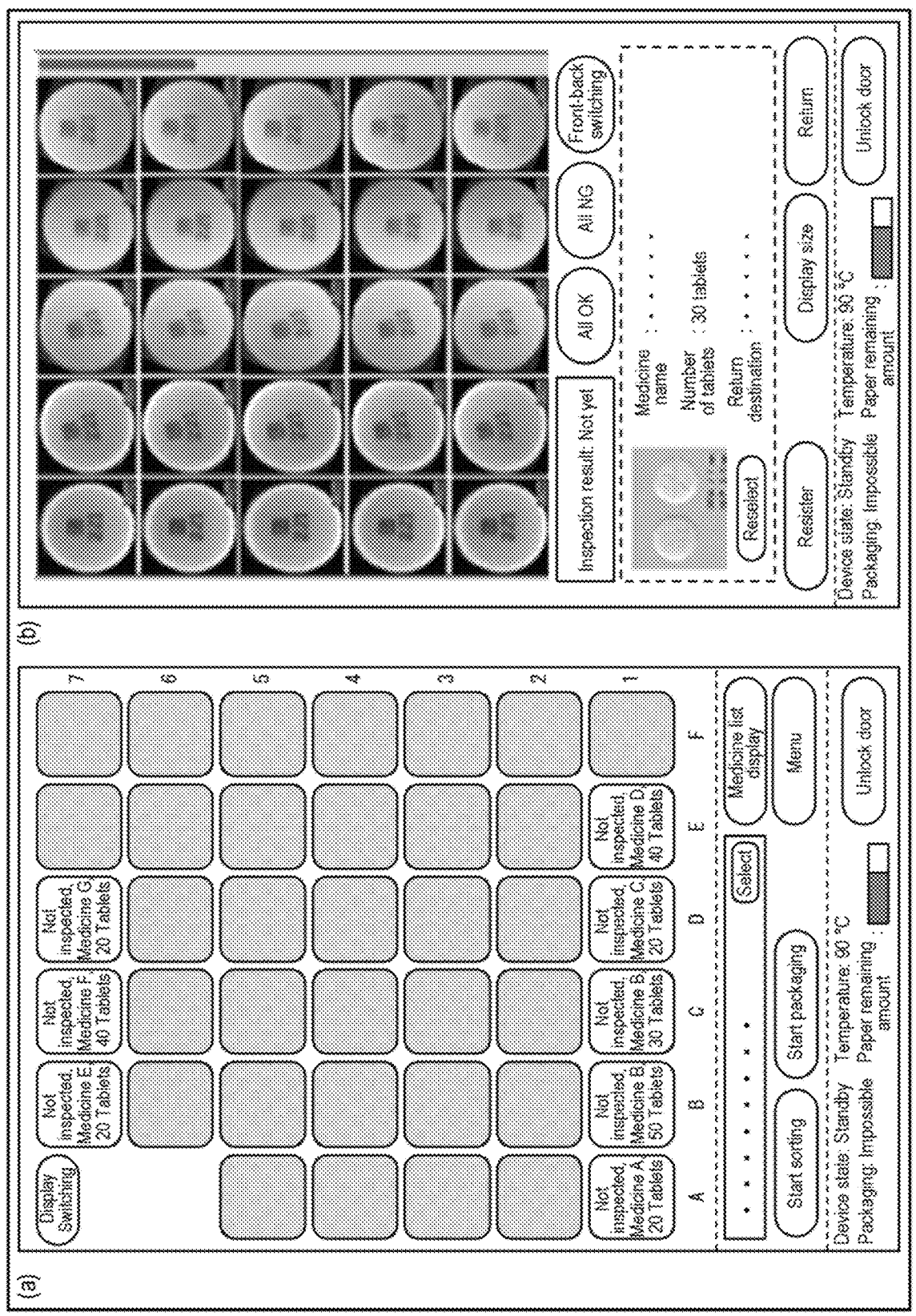
FIG. 11 is a view showing an example of image display, wherein (a) of FIG. 11 is a display example during a medicine sorting process and (b) of FIG. 11 is a display example of image data corresponding to a designated sorting cup.
Figure 12:
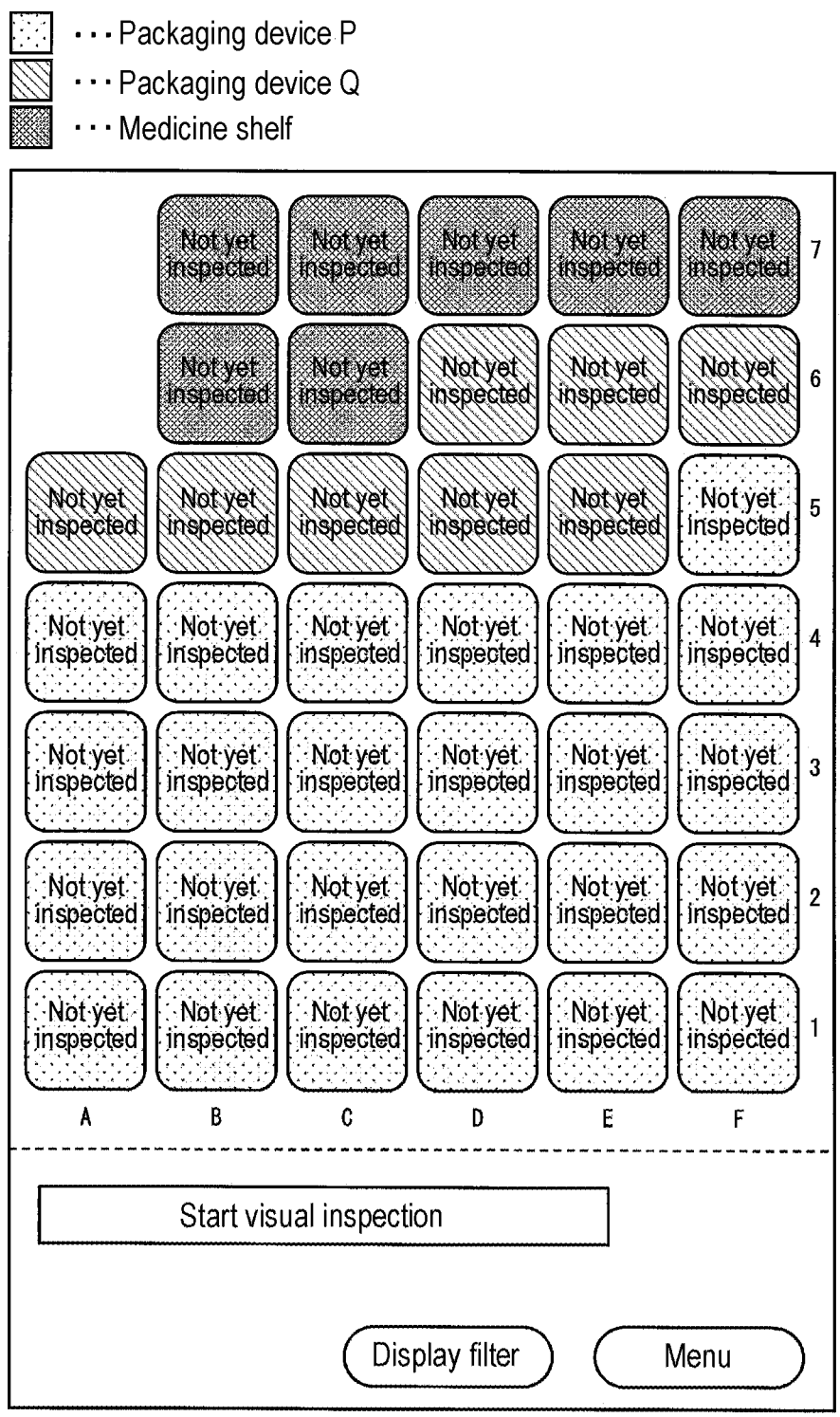
FIG. 12 is a view showing another example of image display.

Next, a display process is described with reference to FIGS. 1, 11, and 12. FIG. 11 is a view showing an example of image display, wherein (a) of FIG. 11 is a display example during a medicine sorting process (an image example showing transition of medicine sorting) and (b) of FIG. 11 is a display example (an image example for visual inspection) of image data corresponding to designated sorting cups 141. FIG. 12 is a view showing another example of image display.

As shown in (a) of FIG. 11, the display control part 67 creates a display image during the medicine sorting process based on sorting positions determined by the sorting control part 62 and the data related to the medicines associated with the sorting positions, and displays the display image on the display part 32. Rectangular portions corresponding to respective sorting cups 141, and each icon such as display switching can receive a user input through the operation part 31.

In the display image of (a) of FIG. 11, a medicine name, the number of medicines, and whether or not visual inspection is completed are displayed in a rectangular portion corresponding to each sorting cup 141 in which medicines are stored. Whenever the sorting of one medicine is completed, the display control part 67 causes the RFID control part 68 to read data related to the medicine from the RFID tag of the sorting cup 141 that stores the medicine at least in the immediate vicinity. Thus, a sorting state can be displayed in real time.

In this display image example, the first row corresponds to the sorting cups 141 provided on the front side (+Y-axis direction side) of the medicine sorting device 1 and the seventh row corresponds the sorting cups 141 provided on the back side (−Y-axis direction side). Further, in this display image example, since fifty tablets (an upper limit of the number that can be stored in one sorting cup 141 in this example) are stored in the B-1st sorting cup 141, it can be seen that the tablets next the 51st tablet are stored in the C-1st sorting cup 141. Further, as shown in this display image example, the sorting control part 62 may store medicines from the sorting cups 141 on the first row of the front side and the sorting cups 141 on the seventh row of the back side. In this case, the front area in the second accommodation part 14 may be set as an area for sorting medicines that are accommodated in the tablet packaging device, and the back area may be set as an area for sorting medicines that are returned to a medicine shelf or the like and are not accommodated in the tablet packaging device. By setting in this manner, it is possible to sort the medicines accommodated in the tablet packaging device into a position where the medicines can be easily taken out.

If a user input is received in a rectangular portion corresponding to a sorting cup 141 in which medicines are stored, the display control part 67 displays all image data of the medicines stored in the sorting cup 141 as shown in (b) of FIG. 11. Specifically, the display control part 67 displays visible light images for all the medicines stored in the sorting cup 141 selected by the user (a visible light image of the medicine placement table 133a acquired after the type of the medicine is determined) among the sorting cups 141 sorted by each type based on the discrimination result.

Thus, the user can visually inspect images of all the medicines in the sorting cup 141 individually on the assumption that the same or the same type of medicines are sorted into the same sorting cup 141. Thus, if there are different medicines or foreign matters, the user can find them.

Further, when a user input for "All OK" or "All NG" is received in connection with task efficiency, the display control part 67 switches the rectangular portion corresponding to the relevant sorting cup 141 in (a) of FIG. 11 into a display indicating that visual inspection has been completed. Further, the RFID control part 68 stores (registers) the completion of visual inspection in the RFID tag of the sorting cup 141. At this time, the completion of visual inspection may be stored in the storage part 80.

Further, regarding a medicine that is associated with a plurality of candidates of medicine data or a medicine that is discriminated as an estimated medicine, medicine data related to the medicine is uniquely specified in the visual inspection. Therefore, the uniquely specified medicine data is registered in the RFID tag or the storage part 80.

Further, as shown in FIG. 12, in the display image during or after the medicine sorting process, the rectangular portions corresponding to respective sorting cups 141 may be color-coded in accordance with a medicine return destination (e.g., a tablet packaging device or a medicine shelf). In the example of FIG. 12, the rectangular portions are color-coded such that the medicines to be returned to a packaging device P, the medicines to be returned to a packaging device Q, and the medicines to be returned to a medicine shelf are distinguished from one another. The return destinations and the display colors set in association with the return destinations are stored in the storage part 80.

For example, when color-coding is performed before visual inspection, the control part collates the medicine data based on the discrimination result of the discrimination part 64 with the medicine data installed in each tablet packaging device, and determines the tablet packaging device to which the medicines of each sorting cup 141 are to be returned based on the collation result. When a medicine is determined as a medicine that is not to be accommodated in the tablet packaging devices, the return destination is determined as the medicine shelf. The display control part 67 performs color-coded display of the rectangular portion based on the determination result. When the medicine data is changed based on visual inspection, the control part changes the display color in accordance with the change result. In case of an estimated medicine, the control part may hold off, for example, the color-coding, and determines the final display color after the medicine data is determined through on visual inspection.

Further, after the visual inspection, the control part may collate the medicine data written in the RFID tag of each sorting cup 141 with the medicine data installed in each tablet packaging device.

By performing the color-coded display in this manner, the user can check at a glance which sorting cup 141 should be taken out in accordance with the purpose of use of a medicine. This color-coded display is particularly useful for a user who owns a plurality of tablet packaging devices. This is because it is possible to reduce the time and effort in checking the return destination at the time of returning a medicine (a sorting cup 141).

[Other Processes]

An example of other processes is described.

(Creation/Update of Medicine Database)

The medicine database manages medicine data related to a plurality of types of medicines. As described above, the medicine database is used for specifying the types of medicines to be handled in the medicine sorting device 1.

It is preferable that the medicine database include all medicine data for a wide variety of medicines. But, it is practically difficult to cover all of them, for example, when the medicine sorting device 1 is shipped. Further, a new medicine may be developed after the medicine sorting device 1 is shipped. Therefore, the medicine database is configured to add (update) medicine data related to a new medicine.

For example, regarding a medicine discriminated as an estimated medicine, when medicine data related to the medicine is uniquely specified through visual inspection as described above, the control part registers the medicine data related to the medicine in the medicine database at the time of registration. This enables a new medicine to be registered in the medicine database, and thus it is possible to update the medicine database at any time. Further, it is not necessary to include all medicines in the stage of creating the medicine database.

Further, the medicine data related to each medicine specified based on the discrimination result of the discrimination part 64 may be predicted by the medicine sorting device 1 in order to support visual inspection. Therefore, the medicine name displayed by the display control part 67 is a predicted medicine name. Based on the displayed image data of each medicine and the displayed predicted medicine name, the user performs a visual inspection and the medicine data related to the medicine is uniquely specified.

Further, as described above, in case where the type of a medicine is discriminated using a reference image (in other words, using a collation result between a target feature and a collation feature), the medicine may not be pre-registered in the medicine database. In this case, the medicine data of the medicine uniquely specified based on the visual inspection as described above is registered in the medicine database as formal medicine data together with the reference image.

(Detection of Position of Adsorption/Shutter Mechanism)

The control part may detect the position of the housing including the second camera 121 and the adsorption/shutter mechanism 122. In this case, the position is detected by, for example, installing distance measurement sensors on the surface the housing facing the +X-axis direction and the surface of the housing facing the +Y-axis direction, respectively, and measuring the distance to the housing of the medicine sorting device 1. Therefore, since the control part can specify the position of the adsorption/shutter mechanism 122, the control part can determine, for example, whether or not the adsorption/shutter mechanism 122 is moving to an accurate sorting position.

(Obstacle Detection Mechanism)

Further, the medicine sorting device 1 may be provided with an obstacle detection mechanism for detecting that any obstacle is placed in the medicine sorting area 2. For example, when a sorting cup 141 is not placed correctly but is placed obliquely with respect to the pedestal 19, the obstacle detection mechanism detects a portion of the sorting cup 141, which protrudes from the uppermost surface of a sorting cup 141 correctly placed on the pedestal 19, as an obstacle. Further, for example, when medicines are stacked overlappingly and protrude from the uppermost surface of a sorting cup 141, the obstacle detection mechanism detects the medicine, which protrudes from the uppermost surface, as the obstacle. For example, when an obstacle is placed in a space between the bottom portion of the housing (the lowermost surface opposed to the pedestal 19) including the second camera 121 and the adsorption/shutter mechanism 122, and the uppermost surface of a sorting cup 141 correctly placed on the pedestal 19, the obstacle detection mechanism detects such an obstacle.

The obstacle detection mechanism includes a laser light source that emits laser light into the aforesaid space, and a sensor that receives the laser light emitted from the laser light source. When an obstacle is placed, the sensor cannot receive the laser light and therefore it is detected that the obstacle is placed. For example, the obstacle detection mechanism is provided at one end portion of the pedestal 19 and a reflection mirror is provided at the opposite end portion. In this case, the sensor receives the laser light that is emitted from the laser light source and is reflected by a reflection mirror. Further, the obstacle detection mechanism may be configured to be movable along the one end portion of the pedestal 19.

(Exclusion of Sorting-Unneeded Medicine)

When a medicine accommodated in the first accommodating part 11 is relevant to a sorting-unneeded medicine that does not need sorting, the medicine sorting device 1 may not sort the medicine. Specifically, when a medicine whose type has been discriminated corresponds to a sorting-unneeded medicine, the discrimination part 64 excludes the medicine from sorting targets.

The sorting-unneeded medicine is, for example, a medicine for which the user has determined that sorting is unnecessary in light of the operation of a medicine sorting task. The sorting-unneeded medicine is set in the medicine sorting device 1 in advance. For example, the user sets conditions for a sorting-unneeded medicine through a sorting condition setting screen. Examples of the conditions may include four conditions described below, and when a medicine meets any of the conditions, the discrimination part 64 excludes a medicine to be discriminated from the sorting targets as a sorting-unneeded medicine. The four conditions are as follows: (1) a medicine whose medicine price is below a predetermined price; (2) a medicine whose final packaging date is prior to a sorting process date by predetermined dates; (3) a medicine with a flag given thereto (e.g., a flag indicative of a psychotropic medicine or a flag indicative of an anticancer medicine); and (4) a medicine whose medicine name includes a specific character string. Further, the medicine price information in above item (1) and the flags in above item (3) may be acquired from a general pharmaceutical database managed by an external device. The final packaging date in above item (2) and the medicine name in above item (4) may be acquired by downloading master data from a tablet packaging device.

When the discrimination part 64 discriminates a medicine as a sorting-unneeded medicine, the conveyance control part 61 controls the adsorption/shutter mechanism 122 to take out the medicine from the medicine placement table 133*a* on which the medicine is placed, and to convey the medicine to the recovery tray 16, and to keep the medicine in one place. In this manner, by excluding a medicine, which the user does not want to sort, from the sorting target, it is possible to exclude unnecessary processes such as the sorting process or the visual inspection for the medicine.

(Image Data Log)

When taking out a medicine from a sorting cup 141 and packaging the medicine, an image obtained when taking out the medicine from the sorting cup 141 may be left in order to reliably specify which medicine has been taken out and packaged (for the purpose of traceability of flow of the processes). When a medicine in a sorting cup 141 is conveyed to the packaging mechanism 6 through the medicine inlet 17 by using the adsorption/shutter mechanism 122, the medicine is imaged by, for example, the second camera 121, and the image data thereof is stored in the storage part 80. In this case, the image data is recorded as a log whenever the medicine is taken out. Therefore, by confirming the image data, it is possible to confirm the validity of a packaging process after the packaging process.

(Designation of Return Source)

A return source before starting the sorting of medicines may be designated, and the return source of the sorted medicines may be left as a history.

For example, the control part of the medicine sorting device 1 acquires return source information by downloading the master data from a tablet packaging device in a hospital. The return source information may be acquired by a user input, or may be acquired by reading a barcode (identification information) affixed to a returned medicine. Therefore, the control part specifies the return source of a medicine accommodated in the first accommodating part 11 before starting the sorting of a medicine. Further, the control part associates the return source information with the data related to the sorted medicine. Therefore, it is possible to manage the history of the return sources of the sorted medicines in the medicine sorting device 1 or an external device connected to the medicine sorting device 1.

Further, in totalization process (totalization task) for the returned medicines, the medicine sorting device 1 or the external device may count the number of returned medicines for each ward, clinic or facility, and may output the result.

(Designation of Prescription-Issuing Physician)

A prescription-issuing physician may be selected before starting the sorting of medicines sorting, and the physician who prescribes the sorted medicines may be left as a history.

For example, the control part of the medicine sorting device 1 may acquire information on a prescription-issuing physician by a user input, or by reading the identification information issued to the physician (e.g., a barcode included in an ID card). Further, the information may be acquired by downloading master data from a tablet packaging device in the hospital. Therefore, the control part specifies the physician who prescribed medicines accommodated in the first accommodating part 11 before starting the sorting of the medicines. Further, the control part associates the information of the physician who prescribed the medicine with the data related to the sorted medicine. Therefore, it is possible to manage the history of the physician who prescribed the sorted medicine in the medicine sorting device 1 or an external device connected to the medicine sorting device 1.

Further, in totalization process (totalization task) for the returned medicines, the medicine sorting device 1 or the external device may count the number of returned medicines for each physician, and may output the result

[Main Configuration of Medicine Sorting Device 1]

The medicine sorting device 1 has various configurations as described above. The following items (1) to (4) are examples of particularly main configurations among the various configurations. The following items (1) to (4) are merely examples, and other configurations of the medicine sorting device 1 are not intended to be excluded from the main configurations.

(1) The medicine sorting device 1 includes: a first accommodating part that accommodates a plurality of types of medicines in a mixed state (the first accommodating part 11); a second accommodating part that accommodates the medicines in the state of being sorted by each type (the second accommodating part 14); an imaging part that images the medicines (the first camera 131); a discrimination part that discriminates the types of the medicines based on an image captured by the imaging part (the discrimination part 64); and a sorting part that sorts the medicines by each type based on the discrimination result performed by the discrimination part and stores the sorted medicines in the second accommodating part (the conveyance/sorting unit 12).

(2) The medicine sorting device 1 includes: an imaging part that images medicines; a discrimination part that discriminates the types of the medicines based on an image captured by the imaging part; a sorting part that sorts the medicines by each type based on a discrimination result performed by the discrimination part; and an image classification part that classifies the image captured by the imaging part for each type of the medicines discriminated by the discrimination part (the image classification part 65).

(3) The medicine sorting device 1 includes: an imaging part that images medicines; an ultraviolet light radiation part that radiates ultraviolet light to the medicines (the ultraviolet light radiation part 134*c*); and a medicine data extraction part that narrows down candidates of medicine data related to the imaged medicines from a medicine database that manages medicine data related to a plurality of types of medicines (the discrimination part 64).

(4) The medicine sorting device 1 includes: an imaging part that images medicines; a discrimination part that extracts features of the medicines in each of the images imaged by the imaging part and compares the features to discriminate the types of the medicines based on whether or not the features are the same; and a sorting part that, when the features is determined to be the same by the discrimination part, sorts medicines, whose type is discriminated by the discrimination part, into the same position as a position into which the medicines whose types are discriminated by that time by the discrimination part are sorted.

[Execution Example by Software]

The control block of the medicine sorting device 1 (particularly, the conveyance control part 61, the sorting control part 62, the imaging control part 63, the discrimination part 64, the image classification part 65, the operation input part 66, the display control part 67, the RFID control part 68, the printing output control part 69) may be realized by a logic circuit (hardware) formed in an integrated circuit (IC chip) or the like, or may be realized by software by using a central processing unit (CPU).

In the latter case, the medicine sorting device 1 includes: a CPU that executes instructions of a program that is software executing each function; a read only memory (ROM) or a storage device (which is referred to as a recording medium) in which the program and various data are recorded to be readable by a computer (or a CPU); a random access memory (RAM) that develops the program, and the like. And, the object of the present invention is achieved by reading the program from the recording medium and executing the program by the computer (or the CPU). As the recording medium, a "non-temporary tangible medium" such as a tape, a disk, a card, a semiconductor memory, a programmable logic circuit, or the like may be used. Further, the program may be supplied to the computer via any transmission medium that is capable of transmitting the program (such as a communication network or a broadcast wave). Further, one aspect of the present invention may be realized even if the program is in the form of a data signal which is realized by electronic transmission and is embedded in a carrier wave.

Hereinafter, additional configurations, processes or the like of the medicine sorting device 1 is described. However, it should be noted that the descriptions made below may include portions that overlap the above-described contents or portions that are specifically described.

<Various Process and Operation Examples>

(Character Recognition)

Figure 13:
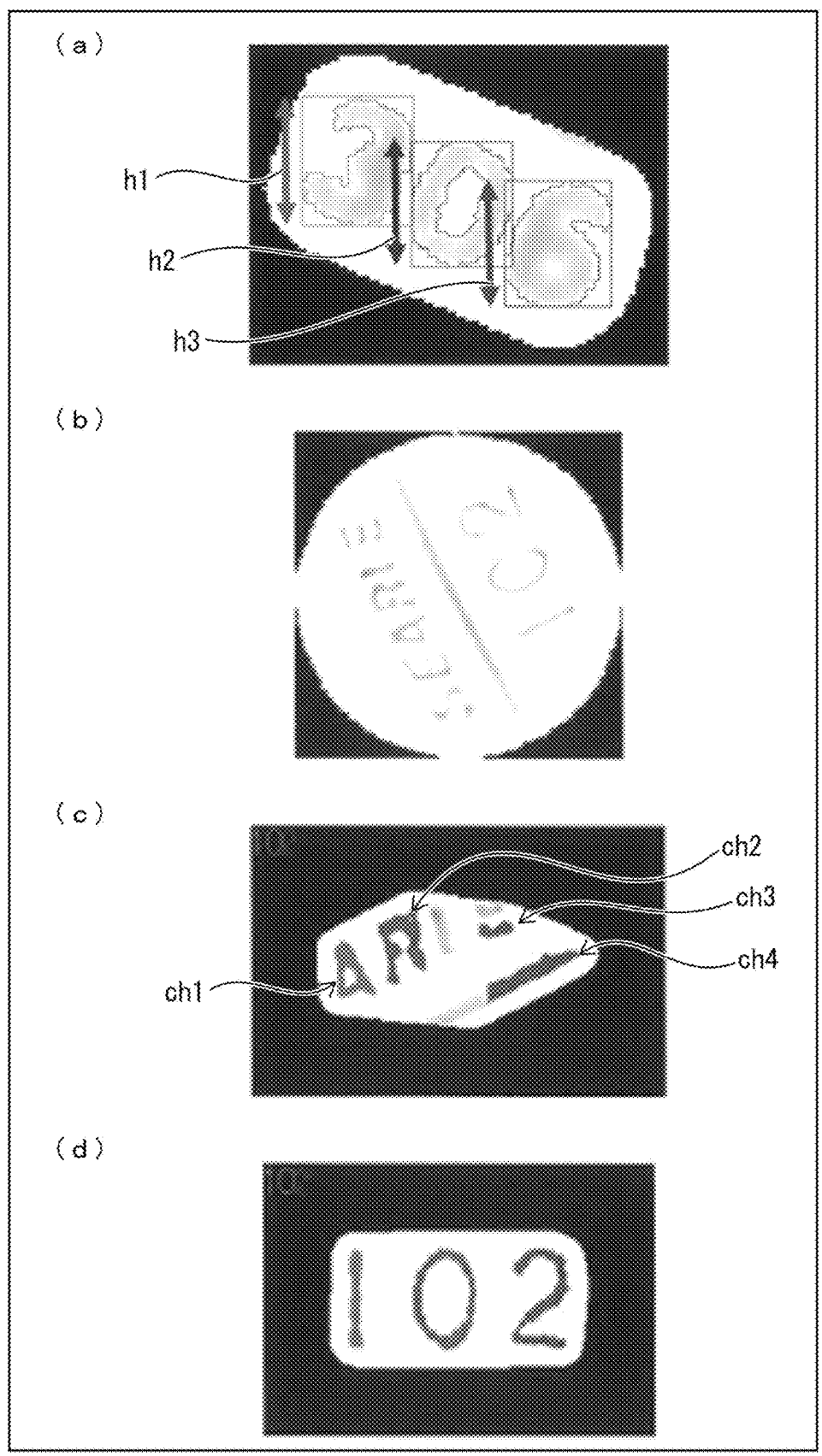
FIG. 13 is a view illustrating an example of a character recognition process.

First, an example of a character recognition process by the discrimination part 64 is described. In FIG. 13, (a) to (d) of FIG. 13 are views illustrating an example of a character recognition process.

In this example, the discrimination part 64 performs a recognition process on a plurality of characters (for example, numeral characters) formed in a medicine included in an image captured by the first camera 131. This recognition process is a process for extracting the features of a medicine by performing the above-described OCR or the like.

The medicine to be subjected to the recognition process is placed on the medicine placement table 133a by the conveyance/sorting unit 12. At this time, the medicine is not placed such that the position of the medicine with the engraving or print formed thereon is oriented in a predetermined direction. Therefore, the discrimination part 64 performs the recognition process while rotating the image of the imaged medicine. In this case, there is a possibility that a shape such as a dividing line or logo formed in the medicine are forcibly recognized as a character.

Therefore, in this example, among the plurality of characters recognized in the recognition process, the discrimination part 64 discriminates characters, which are discriminated as having a size in a predetermined range and forming a string, as characters actually formed in the medicine.

As shown in (a) of FIG. 13, when there are a plurality of portions recognized as characters (rectangular portions in the figure), the discrimination part 64 determines whether or not the lengths h1, h2, and h3 of the long sides in each of the portions are within a preset length range (predetermined range). If the lengths h1, h2, and h3 of the long sides are within the predetermined range, the discrimination part 64 discriminates that each portion has a size within the predetermined range.

For example, a plurality of lengths (heights) of the long sides of portions recognized as characters may be acquired in advance, and the predetermined range may be set using the average value of the heights as a reference. The predetermined range may be appropriately adjusted. For example, the predetermined range is set to a range of 0.8 times or more of the average value and 1.2 times or less of the average value. The predetermined range may be set to a size enough that the characters formed in a medicine are recognizable by the discrimination part 64.

Further, in this example, the length of the long sides is used to determine whether the size of each portion is within the predetermined range, but the determination is not limited thereto. The determination may be made using the length of short sides or the size (area) of each portion.

When it is determined that each portion has a size within the predetermined range, the discrimination part 64 determines whether or not there is a linearity in the arrangement of each portion. For example, the discrimination part 64 connects an end portion of any one side of a portion of interest to an end portion of any one side of a portion located within a predetermined range from the portion of interest. This process is performed for all the portions. When a plurality of line segments connected in this manner are straight lines or can be regarded as straight lines, the discrimination part 64 determines that there is a linearity in the arrangement of each portion forming the line segments.

For example, it is considered a case where an image of a medicine is acquired as shown in (b) of FIG. 13. In this example, descriptions is made as to an example where the discrimination part 64 accurately reads an arrangement of numeral characters.

As shown in (c) of FIG. 13, in the above-described recognition process, the discrimination part 64 recognizes, for example, an actual character "A" as a character "4" (symbol ch1 in the figure) and the actual character "R" as a character "0" (symbol ch2 in the figure). Further, in the above-described recognition process, the discrimination part 64 recognizes, for example, a portion of an actual character "E" as a character "1" (symbol ch3 in the figure) and a portion of an actual dividing line as a character "1" (symbol ch4 in the figure). Further, as shown in (d) of FIG. 13, the discrimination part 64 reads the actual characters "102" as characters "102" in the above-described recognition process.

When the recognition process is performed in this manner, a numeral string different from the actually formed characters "102" may be read.

The discrimination part 64 determines whether or not the size of the character (the above portion) is within the predetermined range and whether or not there is a linearity in the arrangement of the character. The portion denoted by symbol ch3 is excluded from the recognized characters since it does not have a size within the predetermined range. Further, the portions denoted by symbols ch1, ch2, and ch4 are excluded due to no linearity in the arrangement thereof. Further, as for the actual characters "102", it is determined that each of the portions of "1", "0", and "2" in the image has a size within the predetermined range and there is linearity in the arrangement thereof.

As a result, the discrimination part 64 extracts only "102" formed in the actual medicine as a numeral string from the image. As described above, with the discrimination part 64 of this example, it is possible to accurately read the numeral string. With regard to (b) to (d) of FIG. 13, the example of reading a numeral string has been described as an example. But, it is possible to make a similar determination with respect to a character string other than a numeral characters. That is, with the discrimination part 64 of this example, it is possible to improve the accuracy in reading a plurality of characters formed in a medicine.

(Specification of Imaging Position)

Next, an example of an imaging position specifying process by the imaging control part 63 is described. In FIG.

Figure 14:
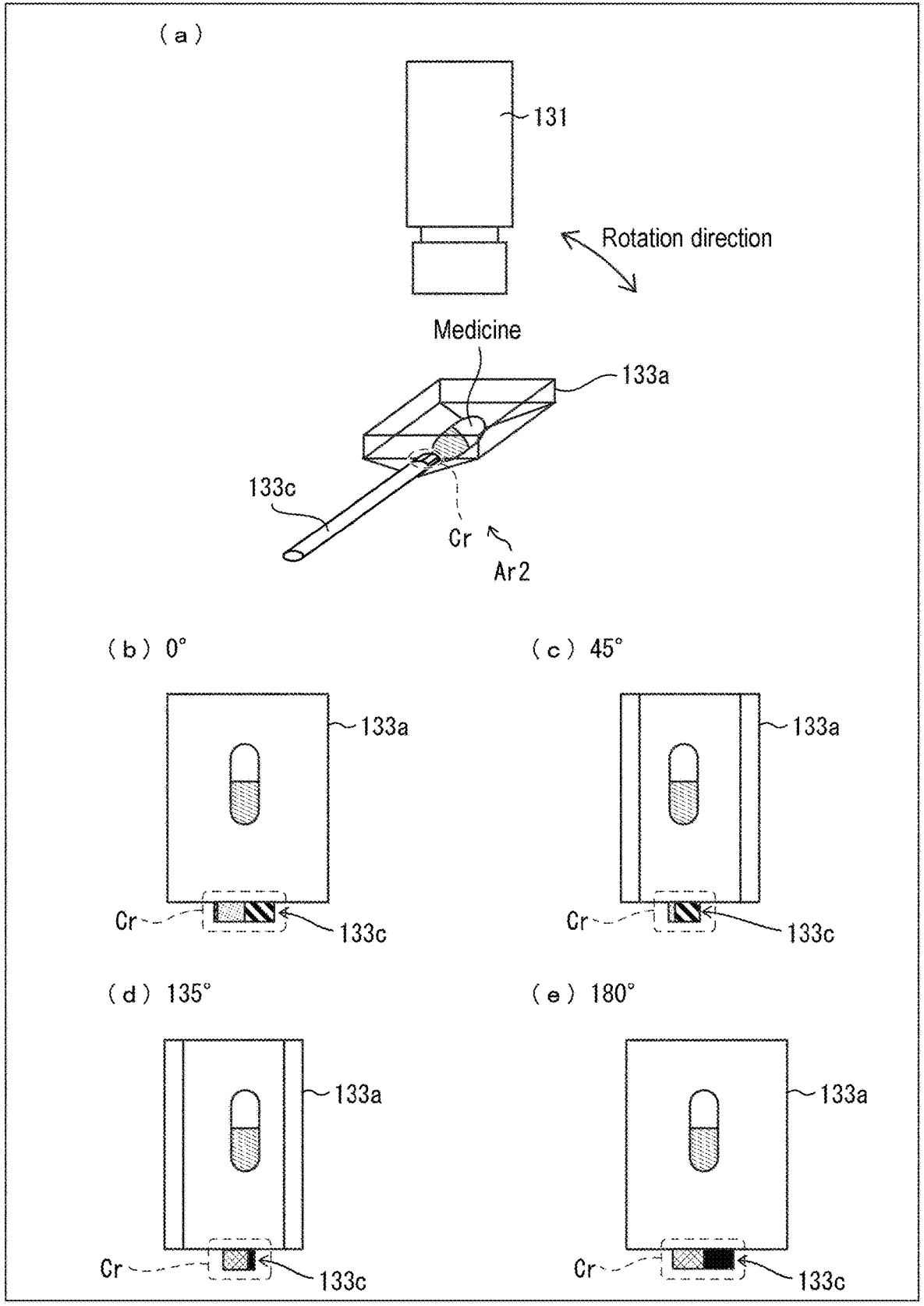
FIG. 14 is a view illustrating an example of an imaging position specifying process.

14, (a) to (e) of FIG. 14 are views illustrating an example of an imaging position specifying process.

As shown in (a) of FIG. 14, the medicine placement table 133a, which is disposed in the disposition area Ar2 and on which a medicine to be imaged is placed, is provided with the shaft portion 133c that supports the medicine placement table 133a. Further, the shaft portion 133c is substantially parallel with the axial direction around which the first camera 131 is rotated when the medicine placement table 133a is disposed in the disposition area Ar2.

The shaft portion 133c of this example is provided with a confirmation area Cr, and the confirmation area is provided with a pattern for determining whether or not an imaging position is appropriate using an image captured by the imaging control part 63. To make this determination possible, in this example, the confirmation area Cr is provided with different patterns in the circumferential direction of the shaft portion 133c. Further, in this example, as the patterns, a plurality of types of colors are given in the circumferential direction of the shaft portion 133c.

For example, a red color, a green color, a blue color, an orange color, and a purple color are evenly given in this order to at least a circumferential portion of the shaft portion 133c as the confirmation area Cr. In this case, as shown in (b) to (e) of FIG. 14, the ratio of each color existing in the confirmation area Cr included in the image captured by the first camera 131 differs depending upon the imaging position of the first camera 131. Thus, it is possible to determine whether or not the first camera 131 is imaging a medicine from a predefined position by, at respective imaging positions, capturing in advance the images as shown in (b) to (e) of FIG. 14.

Specifically, when the images captured for determining the type of a medicine are acquired, the imaging control part 63 determines whether or not the first camera 131 is disposed at an appropriate position by comparing the patterns included in the images with the patterns included in the previously captured images (predetermined patterns).

In this example, the imaging control part 63 obtains in advance the ratio of each color existing in the confirmation area Cr included in the image at each imaging position, and stores the ratio in the storage part 80. The imaging control part 63 obtains the ratio of each color existing in the confirmation area Cr included in the captured image for discrimination of the type of a medicine, and compares the ratio of each color (referred to as a target ratio) with the previously obtained ratio of each color (referred to as a reference ratio). As a result, the imaging control part 63 determines that the imaging position is an appropriate position when the target ratio substantially matches the reference ratio (the difference between the target ratio and the reference ratio is within a predetermined range).

For example, when imaging a medicine from the imaging position of 0° (immediately above the disposition area Ar2), the imaging control part 63 dispose the first camera 131 at the imaging position of 0°, and then images the medicine placed on the medicine placement table 133a from the imaging position. The imaging control part 63 obtains the target ratio from the captured image, reads the reference ratio at the imaging position of 0°, and then compares the target ratio with the reference ratio. Thus, the imaging control part 63 can determine whether or not the captured image is an image captured from the defined imaging position of 0°. That is, it is possible to determine whether or not the first camera 131 images the medicine from the defined imaging position of 0°.

Further, when it is determined that the imaging position is deviated from the defined imaging position, the imaging control part 63 adjusts the imaging position, and then re-determines whether or not the adjusted imaging position is an appropriate position.

Further, in this example, a plurality of types of colors are given in the circumferential direction of the shaft portion 133c that is within the imaging range of the first camera 131, but the present invention is not limited thereto. The patterns may be given in the medicine sorting device 1 so that the imaging control part 63 can specify the imaging position. For example, the patterns may be provided in a portion of the medicine sorting device 1 other than the shaft portion 133c of the medicine sorting device 1 (e.g., a portion of the medicine placement table 133a), which is reflected in an image captured from each imaging position. Further, the patterns may be an uneven shape instead of colors. However, the methods in which the patterns are reflected need to be different from each other at respective imaging positions. Further, in case where a plurality of types of colors are provided in the circumferential direction of the shaft portion 133c, the colors are not limited to the above five colors and a plurality of types of colors do not need to be evenly disposed, as long as a unique ratio is obtained for each imaging position.

As described above, the imaging control part 63 compares the pattern of a predetermined portion other than the medicine, which is included in the image captured by the first camera 131, with a predetermined pattern included in the image in advance captured by the first camera 131. This enables the imaging control part 63 to determine whether or not the imaging position of the first camera 131 is a predefined position. Further, by using the simple method of providing patterns in the imaging range of the first camera 131, the imaging control part 63 can recognize whether or not the first camera 131 is imaging a medicine from an appropriate position.

(Specification of Adsorption Position)

Figure 15:
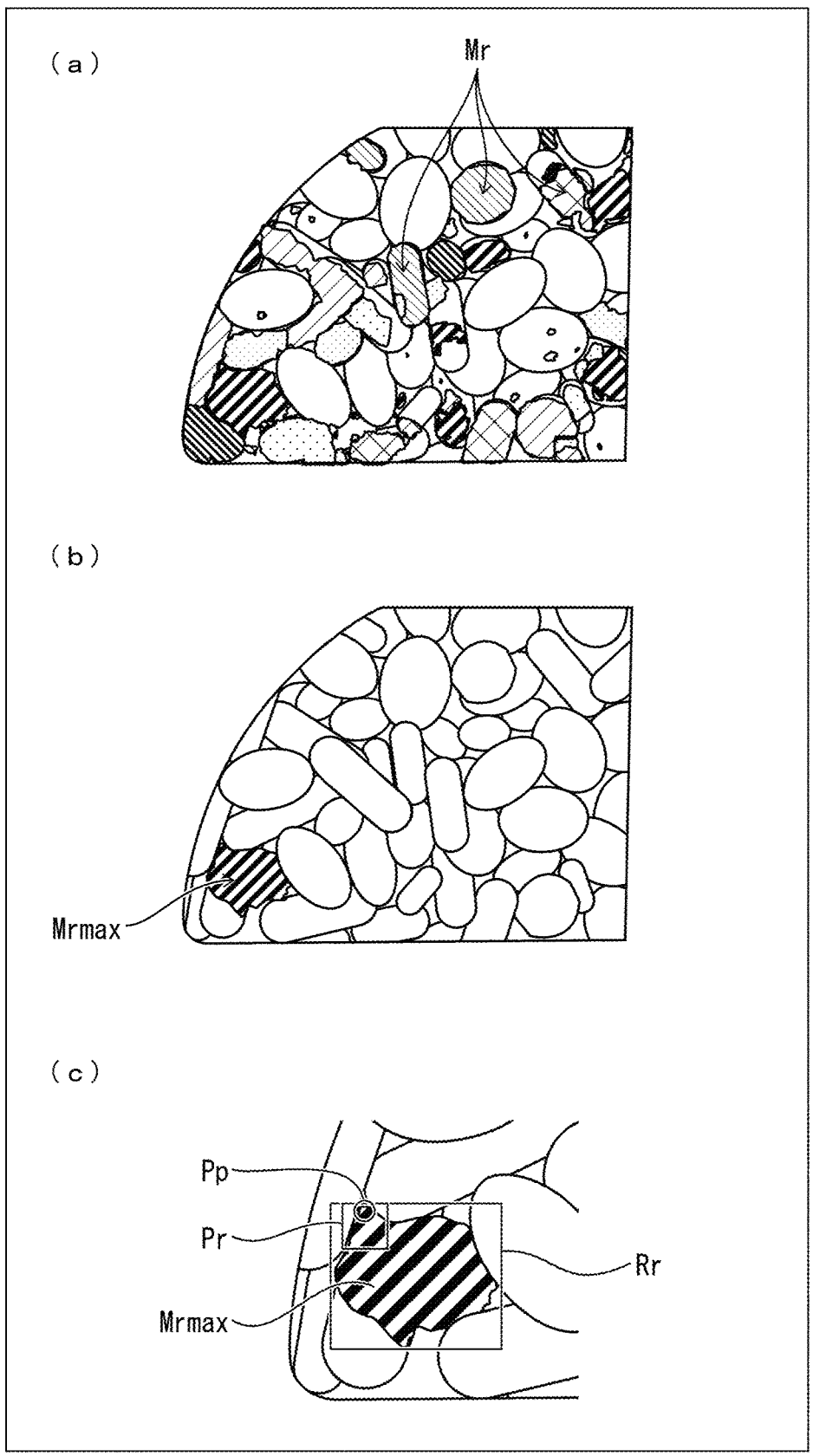
FIG. 15 ((a) to (c) of FIG. 15) is a view illustrating an example of an adsorption position specifying process.

Next, an example of an adsorption position specifying process by the conveyance control part 61 is described. In FIG. 15, (a) to (c) of FIG. 15 are views illustrating an example of an adsorption position specifying process.

As described above, the conveyance control part 61 controls the conveyance/sorting unit 12 that conveys a medicine from the first accommodating part 11 toward the first camera 131 (specifically, the receiving area Ar1). The conveyance control part 61 of this example specifies a position in a protruding area, which includes a protruding portion of an estimated medicine area that is estimated to include a medicine in an image captured by the second camera 121, as an adsorption position at which the adsorption mechanism adsorbs the medicine.

Specifically, as shown in (a) of FIG. 15, the conveyance control part 61 narrows down medicine adsorption areas (picking areas) in an image captured by the second camera 121, and then extracts a plurality of estimated medicine areas Mr based on a luminance distribution in the captured image. For example, a known Watershed algorithm is used to extract the estimated medicine areas Mr based on the luminance distribution.

As shown in (b) of FIG. 15, the conveyance control part 61 specifies a maximum estimated medicine area Mrmax that is the largest among the plurality of extracted estimated medicine areas Mr. The conveyance control part 61 determines whether or not the maximum estimated medicine area Mrmax has a predetermined shape or a shape similar to a predetermined shape. The predetermined shape is a shape unique to a medicine, for example, a shape of a tablet or a capsule. That is, the predetermined shape is a shape having a relatively high roundness or rectangularity.

When it is determined that the maximum estimated medicine area Mrmax has a shape different from the predetermined shape, the conveyance control part 61 determines that a plurality of medicines are adjacent to or overlap each other in the maximum estimated medicine area Mrmax. For example, when it is determined that the degree of coincidence between the maximum estimated medicine area Mrmax and the predetermined shape is equal to or less than a predetermined value, the conveyance control part 61 determines that the maximum estimated medicine area Mrmax has a shape different from the predetermined shape (i.e., an unnatural shape as a medicine).

When it is determined that the maximum estimated medicine area Mrmax is a shape different from the predetermined shape, the conveyance control part 61 sets a circumscribed rectangular area Rr that circumscribes the specified maximum estimated medicine area Mrmax as shown in (b) of FIG. 15. The conveyance control part 61 specifies a protruding portion Pp that protrudes most in a predetermined area inscribed in an outer periphery of the set circumscribed rectangular area Rr, and then specifies a protruding area Pr including the protruding portion Pp.

Thereafter, the conveyance control part 61 specifies any position (e.g., a center of the protruding area Pr) in the specified protruding area Pr as an adsorption position.

When a plurality of medicines are adjacent to or overlap each other in the first accommodating part 11, even if the vicinity of the center of the estimated medicine area Mr is specified as an adsorption position, there is a possibility that the medicine is not adsorbed. According to this example, even if a plurality of medicines are adjacent to or overlap each other, it is possible to specify a position where a medicine is highly likely to be present as an adsorption position. Therefore, it is possible to adsorb a medicine more reliably.

Further, in this example, the adsorption position is specified by using the maximum estimated medicine area Mrmax, but the present invention is not limited thereto. The adsorption position may be specified by using the estimated medicine area Mr other than the maximum estimated medicine area Mrmax. Further, in this example, it is determined whether or not the shape of the maximum estimated medicine area Mrmax has a predetermined shape, but the present invention is not limited thereto. Without performing such determination, the adsorption position may be specified by using one estimated medicine area Mr among a plurality of extracted estimated medicine areas Mr.

(Specification of Medicine Adsorption Range)

Figure 16:
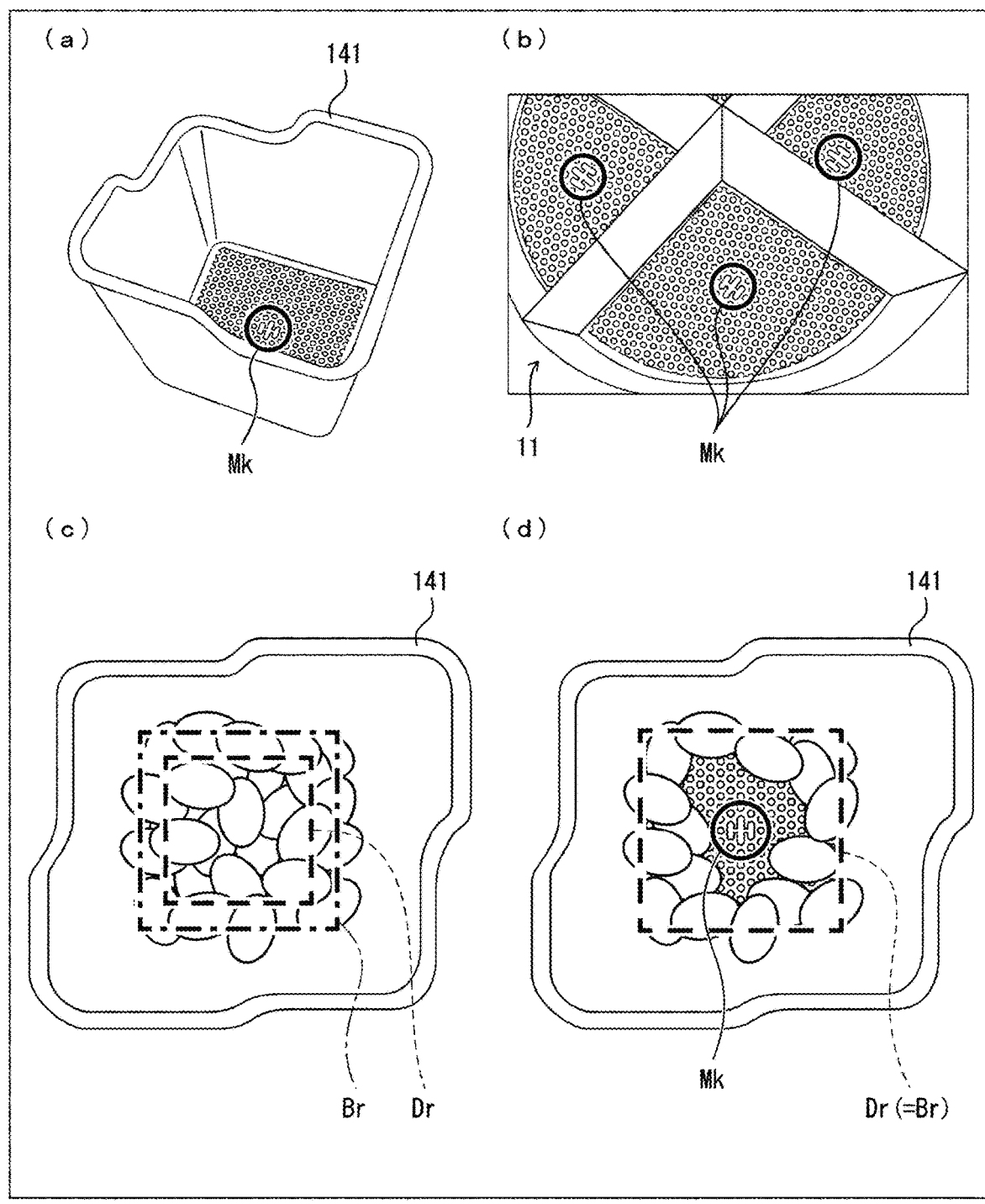
FIG. 16 ((a) to (d) of FIG. 16) is a view illustrating an example of a medicine adsorption range specifying process.

Next, an example of a medicine adsorption range specifying process performed by the conveyance control part 61 or the sorting control part 62 is described. In FIG. 16, (a) to (d) of FIG. 16 are views illustrating an example of a medicine adsorption range specifying process.

Based on whether or not at least a portion of the bottom portion of the sorting cup 141 is included in the image of the sorting cup 141 captured by the second camera 121, the sorting control part 62 (detection area changing part) in this example changes a detection area for detecting a medicine accommodated in the sorting cup 141. Similarly, based on whether or not at least a portion of the bottom portion of the first accommodating part 11 is included in the image of the first accommodating part 11 captured by the second camera 121, the conveyance control part 61 (detection area changing part) in this example changes a detection area for detecting a medicine accommodated in the first accommodating part 11. This process may be performed by at least one of the sorting control part 62 and the conveyance control part 61.

To implement this detection area specifying process, in this example, marks Mk are provided on the bottom portion of the sorting cup 141 as shown in (a) of FIG. 16. Further, as shown in (b) of FIG. 16, marks Mk are formed in the bottom portion of the first accommodating part 11. In this example, a sheet provided with the marks Mk is inserted to the bottom portion, but the marks Mk may be formed directly on the bottom portion. Since the detection area specifying process is the same in the sorting control part 62 and the conveyance control part 61, the process performed by the sorting control part 62 is described below as an example.

When the bottom portion of the sorting cup 141 is not included in the image captured by the second camera 121, the sorting control part 62 specifies an area smaller than a bottom portion size Br of the sorting cup 141 as a detection area Dr as shown in (c) of FIG. 16. In this example, when no mark Mk is recognizable in the image, the sorting control part 62 determines that the bottom portion is not included in the image.

When the bottom portion is not included in the image, it may be determined that the number of medicines contained in the sorting cup 141 is large. Therefore, considering that the sorting cup 141 may be disposed to be deviated from a predetermined disposition position, the sorting control part 62 specifies a range smaller than the bottom portion size Br as the detection area Dr.

Further, when at least a portion of the bottom portion of the sorting cup 141 is included in the captured image, the sorting control part 62 specifies a range substantially the same as the bottom size Br of the sorting cup 141 as the detection area Dr, as shown in (d) of FIG. 16. This detection area Dr is a detection area Dr that should be originally set. In this example, when a mark Mk can be recognized in the image, the sorting control part 62 determines that the bottom portion is included in the image.

When the bottom portion is included in the image, it may be determined that the number of medicines contained in the sorting cup 141 is small. Further, it may be determined that the medicine is present in the vicinity of the end portion of the sorting cup 141. Therefore, the sorting control part 62 specifies a range substantially the same as the bottom portion size Br as the detection area Dr. The size of the detection area Dr may be obtained by using the mark Mk as a reference.

By changing the detection area Dr (specifically, its size) based on whether or not the bottom portion is included in the image in this manner, the detection area Dr can be specified in accordance with the number of medicines contained in the sorting cup 141 or the first accommodating part 11. Moreover, possibility that a medicine cannot be taken out due to the positional deviation of the sorting cup 141 or the first accommodating part 11 can be reduced. That is, according to the above-described process, it is possible to more reliably take out a medicine.

The above-described medicine taking-out method (first taking-out method) is useful when the sorting cup 141 or the first accommodating part 11 is substantially transparent. In case of being substantially transparent, for example, the bottom portion surface of the sorting cup 141 or the first accommodating part 11 has a fine uneven shapes, and the side surface thereof is substantially transparent. In this case, when the sorting control port 62 or the conveyance control part 61 analyzes the image captured by the second camera 121, there is a possibility that a boundary portion between the bottom portion surface and the side surface is erroneously detected as a portion of a medicine. When the sorting control part 62 or the conveyance control part 61 analyzes the image, there is a possibility that a relatively small medicine placed on the boundary portion may not be detected. According to the first extraction method, such a possibility can be reduced.

Further, when the sorting cup 141 or the first accommodating part 11 has a hue black color), particularly when it is unified with one color, the sorting control part 62 or the conveyance control part 61 can reduce the possibility of being affected by the boundary portion in the above-described image analysis. Therefore, the sorting control part 62 or the conveyance control part 61 can stably detect a medicine based on luminance, color or the like. That is, it is possible to stably detect a medicine from the sorting cup 141 or the first accommodating part even if the first taking-out method is not employed.

Further, when the sorting cup 141 or the first accommodating part 11 has a hue, for example, a medicine may be taken out from the sorting cup 141 by, for example, a second taking-out method different from the first taking-out method. In this case, for example, the sorting control part 62 moves the adsorption mechanism with respect to the bottom portion surface such that medicines are sequentially adsorbed from the medicine existing in the vicinity of the center of the bottom portion surface of the sorting cup 141. Specifically, the sorting control part 62 first specifies an area, which is narrowed down to the vicinity of the center including the center of the bottom portion surface, as the medicine adsorption area, and controls the position of the adsorption mechanism so as to adsorb a medicine in that area. Thereafter, the sorting control part 62 gradually (e.g., in two steps) expands the adsorption area toward the side surface. Therefore, even if the medicines are stacked in the sorting cup 141, the medicines can be adsorbed while collapsing the medicines from the vicinity of the center. Further, the conveyance control part 61 may take out the medicines from the first accommodating part 11 by the same process.

Further, when the sorting cup 141 or the first accommodating part 11 has a hue, the sorting control part 62 or the conveyance control part 61 can stably detect a substantially transparent capsule, which is difficult to be detect on the bottom portion surface having a fine uneven shape, or a relatively small medicine that stands erect on the bottom portion surface.

[Designation of Medicine and Sorting Cup]

Figure 17:
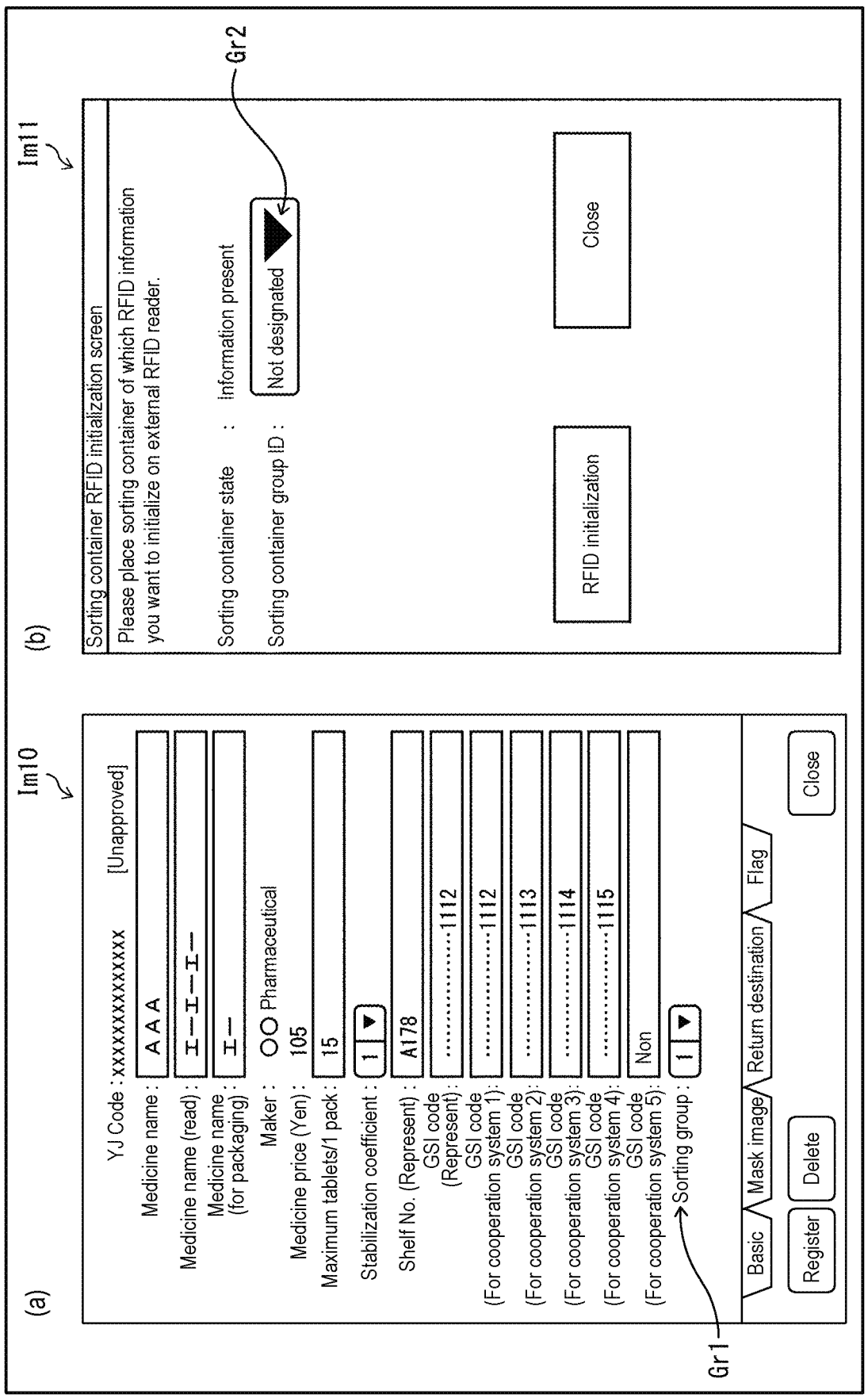
FIG. 17 ((a) and (b) FIG. 17) is a view illustrating an example of a medicine and sorting cup designation process.

Next, an example of a medicine and a sorting cup 141 designation process performed by the sorting control part 62 is described. In FIG. 17, (a) and (b) of FIG. 17 are views illustrating an example of the medicine and sorting cup 141 designation process. Specifically, (a) of FIG. 17 is a maintenance image Im10 when changing (e.g., maintaining) a medicine database, and (b) of FIG. 17 is an initialization image Im11 when the storage content of the RFID tag (information recording medium) of the sorting cup 141 is initialized.

Further, an image to be displayed on the display part 32 may be referred to as a screen. For example, the maintenance image and the initialization image may be referred to as a maintenance screen and an initialization screen, respectively. Further, a sorting image, an inspection image, a sorting medicine list image, a display color switching image, a return source selection image, an enlarged display image, and a totalization image, which are described below, may be referred to as a sorting screen, an inspection screen, a sorting medicine list screen, a display color switching screen, a return source selection screen, an enlarged display screen, and a totalization screen, respectively.

A sorting group selection area Gr1 of the maintenance image Im10 and a sorting container group setting area Gr2 of the initialization image Im11 are areas for receiving a user manipulation for setting sorting identification information. The sorting identification information is information for sorting a medicine into a predetermined sorting cup 141 and is given to a medicine which the user desires to sort into the predetermined sorting cup 141.

Specifically, when a user wants to sort a specific medicine into a specific sorting cup 141, the user causes the maintenance image Im10 of the medicine to be displayed on the display part 32, and inputs a sorting group number for specifying a sorting group to the sorting group selection area Gr1 of the maintenance image Im10 as sorting identification information.

Further, the user causes the initialization image Im11 to be displayed on the display part 32. Then, the user inputs the same sorting group number as the sorting group number, which is input in the sorting group selection area Gr1 of the maintenance image Im10, to the sorting container group setting area Gr2 of the initialization image Im11, as sorting identification information.

The sorting group number inputted to the sorting group selection area Gr1 and the sorting group number inputted to the sorting container group setting area Gr2 are stored in the storage part 80. Therefore, the sorting control part 62 can specify a medicine, to which the sorting group number inputted in the sorting group selection area Gr1 is assigned, and a sorting cup 141 to which the same sorting group number as the sorting group number input to the sorting container group setting area Gr2 is assigned. That is, the conveyance/sorting unit 12 can sort the specific medicine into the specific sorting cup 141.

Further, the sorting identification information may be information for specifying a sorting cup 141. In this case, this sorting identification information is inputted to the sorting group selection area Gr1 and the sorting container group setting area Gr2.

The sorting cup 141 is reused. Thus, it is necessary to clean the used sorting cup 141 when sorting a medicine that is desirable not to contact with other medicines, such as colored medicines or OD tablets (intraoral disintegration tablets). In a ward or the like where there are many returned medicines such as colored medicines or OD tablets, it may take time to clean sorting cups. Such medicines may be sorted into specific sorting cups 141 by using sorting identification information. Therefore, it is possible to reduce or eliminate the cleaning task for sorting such medicines.

(Determination of Sorting Position)

Next, an example of a sorting position determination process performed by the sorting control part 62 is described. By controlling the conveyance/sorting unit 12, the sorting control part 62 may sort a medicine specified as a target to be taken out from the medicine sorting device 1 into a medicine taking-out side in the medicine sorting device 1 (a sorting cup 141 disposed in the front area in the second accommodating part 14).

Specifically, based on return destination information related to the return destination of the sorted medicines, the sorting control part 62 may determine whether or not a journal is necessary. The medicine data related to medicines reflecting a visual inspection result by the user is printed in the journal. When it is determined that a medicine requires the journal, the sorting control part 62 specifies the medicine as a target to be taken out from the medicine sorting device 1.

The return destination information is stored in the storage part 80 in association with medicine data related to the medicine, respectively. The return destination information includes, for example, reader information indicating whether or not the return destination or a return assisting device is provided with a reader (e.g., an RFID reader) for reading medicine data. Further, for example, the return destination information includes packaging device information, which indicates whether the packaging mechanism 6 belongs to to the medicine sorting device 1, as information indicating the return destination.

The return destination includes, for example, a tablet packaging device, a powder medicine packaging device, a medicine shelf, or the packaging mechanism 6 provided in the medicine sorting device 1. The return assisting device is a device for returning to the return destination (e.g., a medicine shelf). Further, at least the reader information is acquired from other facility or other device (e.g., the aforementioned return destination or return assisting device) different from the medicine sorting device 1.

Here, for example, the return assisting device includes a reading part that can read medicine data (e.g., medicine identification information) and return destination information related to a medicine from a journal, and a display part that displays medicine data and return destination information read by the reading part. When the medicine data and the return destination information are represented by at least a barcode, a two-dimensional code, or the like, the reading part is realized as a barcode reader. Further, the display part displays detailed information such as a medicine shelf (e.g., a shelf number) included in the return destination information read by the reading part. Since the return destination information is displayed on the display part, it is possible to reduce the possibility that the user erroneously determines the return destination. Further, shelf identification information may be given to each medicine shelf as a return destination. In this case, for example, the return assisting device reads the shelf identification information given to a medicine shelf in addition to the return destination information given to a journal. The return assisting device collates the read information and informs the collation result. Therefore, it is possible to more reduce the possibility that the user using the return assisting device erroneously determines the medicine shelf of the medicine return destination.

When sorting a medicine, the sorting control part 62 determines whether or not the return destination is the packaging mechanism 6 by referring to the return destination information of the medicine. Further, when the return destination is other facility or other device, the sorting control part 62 determines whether or not the return destination is provided with an RFID reader. When it is determined that the return destination is other facility or other device and the return destination is not provided with an RFID reader, the sorting control part 62 determines that the medicine requires the journal. Further, when it is determined that the return destination is the packaging mechanism 6 or when it is determined that the return destination is provided with an RFID reader, the sorting control part 62 determines that the medicine does not require the journal.

The sorting control part 62 controls the conveyance/sorting unit 12 such that medicines requiring a journal are sorted into the sorting cups 141 disposed in the front area. Whenever it is determined that a journal is necessary, the conveyance/sorting unit 12 sequentially accommodates the medicines from, for example, the sorting cup 141 disposed on the front right side. Further, the sorting control part 62 controls the conveyance/sorting unit 12 such that medicines that do not require a journal are sorted into the sorting cups 141 disposed in the back area. Whenever it is determined that a journal is not necessary, the conveyance/sorting unit 12 sequentially accommodates the medicines from, for example, the sorting cup 141 disposed on the back left side.

The journal is inserted into a sorting cup 141 in which the sorted medicines are accommodated. When the journal is inserted into the sorting cup 141, the user needs to take out the journal from the medicine sorting device 1. By the above-described process, the medicine that need to be taken out (that is, the medicines that require the journal) may be accommodated in a front sorting cup 141 that is easy for the medicine to taken out.

Further, a sorting cup 141 for sorting medicines to be taken out (that is, a predetermined area on the front side where medicines to be taken out are sorted) may be set in advance.

Further, the return destination information may not include the reader information. In this case, the sorting control part 62 may determine whether or not the journal is necessary, for example, by using only the return destination of medicines.

For example, when the return destination is a packaging device, the sorting control part 62 determines the necessity of the journal for the medicines to be sorted by specifying which packaging device that packaging device is. Since it is possible to know in advance whether or not an RFID reader is provided for each packaging device, it is possible to store the necessity of the journal in association with each packaging device. Also in this case, since the journal is unnecessary for the medicine whose return destination is a packaging device provided with an RFID reader, the sorting control part 62 sorts the medicines into a sorting cup 141 disposed in the rear area. Further, when the return destination is a medicine shelf, the journal is required. Therefore, the sorting control part 62 sorts the medicine whose return destination is a medicine shelf into a sorting cup 141 disposed in the front area.

Here, the journal may actually be issued as follows. When the user places a sorting cup 141 on the first RFID reader/writer unit 5, the display control part 67 reads information stored in the RFID tag of the sorting cup 141. This causes the display control part 67 to display an inspection image (to be described below) of a medicine accommodated in the sorting cup 141. The user performs a visual inspection of the medicine by checking the inspection image. After the visual inspection, the user determines the necessity of the journal in accordance with the return destination of the medicine accommodated in the sorting cup 141, and when the journal is necessary, a user input for issuing the journal is performed on a journal necessity check image. Upon receiving the user input, the printing output control part 69 controls the printing output part 4 to issue the journal. The user inserts the issued journal into the sorting cup 141 that has been visually inspected. Therefore, it is possible to prevent the user from mistaking the journal and erroneously inserting the journal into other sorting cup by causing the journal to be printed whenever a sorting cup 141 is placed on the first RFID reader/writer unit 5.

Further, as described above, the sorting control part 62 may sort a medicine accommodated in the tablet packaging device into the front area, and may sort a medicine not accommodated in the tablet packaging device into the back area. In this case, information indicating whether or not a sorted medicine is accommodated in the tablet packaging device is stored in the storage part 80 in association with, for example, medicine data related to the medicine. Further, the sorting control part 62 may determine whether or not the medicine is accommodated in the tablet packaging device based on the return destination information.

Further, when sorting medicines into the front area of the second accommodating part 14, the sorting control part 62 sequentially stores the medicines into the second accommodating part 14 from the frontmost row toward a center. When sorting medicines into the back area of the second accommodating part 14, the sorting control part 62 sequentially stores the medicines into the second accommodating part 14 from the backmost row toward the center.

(Specification of Medicine Shape)

Next, an example of a medicine shape specifying process performed by the discrimination part 64 is described. In this embodiment, as described above, the first camera 131 images a medicine from the positions of θ=0° and 180°, and then, when the type of a medicine cannot be specified as one type, the first camera 131 images the medicine from the positions of θ=45° and 135°.

Here, the tablet generally has a substantially circular shape when viewed in a plan view and a substantially rectangular shape when viewed from a side. Further, the capsule generally has a substantially cylindrical shape (however, its end portion has a substantially hemispherical shape). Therefore, when the capsule is viewed in a plan view and when viewed from a side, the shape of the capsule is substantially rectangular.

Accordingly, when a medicine is imaged from the positions of θ=0° and 180° (that is, when the medicine is imaged from a positions for a plan view), it is possible to determine whether the medicine is a tablet or a capsule. Further, the shape of a tablet included in the images captured from the positions of θ=0° and 180° is substantially circular, but the shape of the tablet included in the images captured from the positions of θ=45° and 135° is substantially rectangular. That is, when captured from the positions of θ=0° and 180° and when captured from the positions of θ=45° and 135°, the shapes of the tablet in the images are different from each other. Further, in case of a capsule, even if the capsule is imaged from any position, the shapes of the capsule in the images are substantially the same.

Therefore, in this example, first, the discrimination part 64 determines whether or not a medicine is a tablet based on the shape of the medicine included in the image captured by the first camera 131 from the position of θ=0° (first direction) or 180° (second direction opposite to the first direction). The position of θ=0° is a position (direction) opposed to the placement surface of the medicine placement table 133a on which the medicine is placed.

For example, by extracting the shape of the medicine from images captured from these positions and obtaining the degree of coincidence with a general tablet shape stored in the storage part 80, the discrimination part 64 determines whether the medicine is a tablet or a capsule. First, the first camera 131 images the medicine from the position of θ=0° or 180°. Therefore, it is possible to speed up the medicine discrimination process by performing narrowing-down as to whether the medicine is a tablet or a capsule in the initial stage of the medicine discrimination process.

Further, when the discrimination part 64 cannot determine whether the medicine is a tablet based on the image captured from the position of θ=0° or 180°, the first camera 131 images the medicine from the position of θ=45° or 135° (i.e., in an oblique direction with respect to the placement surface). Then, the discrimination part 64 determines whether or not the medicine is a tablet based on the shapes of the medicine included in the image captured from the position θ=0° or 180° and the image captured from the position θ=45° or 135°. For example, the discrimination part 64 determines whether or not the medicine is a tablet by comparing a first shape of the medicine included in the image captured from the position θ=0° or 180° and a second shape of the medicine included in the image captured from the position θ=45° or 135°.

As described above, in case of a tablet, the first shape and the second shape are different, but, in case of a capsule, the first shape and the second shape are substantially the same. Therefore, when the first shape and the second shape substantially are the same (the difference between the first shape and the second shape is within a predetermined range), the discrimination part 64 determines that the medicine is a capsule, and, when the difference is beyond the predetermined range, the discrimination part 64 determines that the medicine is a tablet.

Further, in this embodiment, since the position opposed to the placement surface is the position of θ=0°, the imaging direction from the position of θ=0° is described as the first direction, but the present invention is not limited thereto. That is, the imaging direction in the case of capturing an image from a position opposed to the placement surface may be the first direction.

Further, in this embodiment, a camera having a manual focusing function is employed as the first camera 131, but a camera having an auto-focusing function may be employed as the first camera 131. When the first camera 131 has an auto-focusing function, it is possible to focus the medicine depending upon the height of the medicine.

For example, the imaging control part 63 adjusts the focus by using information indicating a diameter of a medicine registered in advance. In case of a capsule, since the diameter of the medicine is the height of the medicine when placed on the medicine placement table 133a, the focus is adjusted by using the information on the diameter. Further, in case of a tablet, for example, the height of a medicine to be applied when the diameter is equal to or larger than a predetermined diameter and the height of a medicine to be applied when the diameter is smaller than the predetermined diameter are stored in the storage part 80. The imaging control part 63 specifies the height of a medicine applied from the diameter of a medicine registered in advance, and adjusts the focus depending upon the height of the medicine.

(Example of Using Medicine Fixation Information)

Next, an example of using medicine-specific information for specifying a medicine (the type of a medicine) is described. In general, medicine-specific information is individually assigned to each device that handles medicines. Therefore, in some cases, medicine-specific information for the same medicine may be differently assigned to, for example, the medicine sorting device 1 and other facility or device different from the medicine sorting device 1 (e.g., a tablet packaging device or a powder medicine packaging device as a return destination, or a return assisting device).

For example, it is assumed that "001", "002", and "003" are stored as medicine-specific information for any medicine in the medicine sorting device 1, and it is assumed that "002" and "003" are stored as the medicine-specific information for such a medicine in other device or other facility. When a plurality of pieces of medicine-specific information are stored for one medicine and the initially-registered medicine-specific information is used for printing a journal, the medicine sorting device 1 adopts "001" as the medicine-specific information. That is, the medicine sorting device 1 issues a journal printed with "001" as the medicine-specific information. Further, when the medicine-specific information is GS1, for example, the information is printed as a GS1 barcode in the journal.

In this case, even if the medicine-specific information printed in the journal is read by other device or other facility, "001" is not stored as the medicine-specific information in said other device or other facility. Therefore, collation cannot be performed and the medicine cannot be returned to said other device or other facility.

Therefore, in this example, the printing output control part 69 prints, in the journal, at least one of a plurality of pieces of medicine-specific information related to sorted medicines acquired from a return destination or a return assisting device (other device or other facility different from the medicine sorting device 1).

Specifically, from all of the return destinations and return assisting devices, the control part acquires in advance all the medicine-specific information managed by these devices in association with the return destinations. When the medicine-specific information is managed with the medicine database, the control part may acquire the medicine database.

If the return destination for a sorted medicine is specified, the printing output control part 69 extracts at least one of a plurality of pieces of medicine-specific information that are managed by the specified return destination (a return assisting device if the return destination is a medicine shelf). When the medicine database is acquired, the printing output control part 69 extracts the medicine-specific information of a medicine to be returned from the medicine database managed by the specified return destination or return assisting device. For example, data, which is obtained by text-converting a medicine-specific information file extracted from the medicine database, may be used as medicine-specific information used for printing on a journal.

The printing output control part 69 issues a journal in which the extracted medicine-specific information is printed as, for example, a GS1 barcode. Therefore, since the medicine-specific information of the return destination is necessarily used to issue the journal, it is possible to reliably perform collation in the return destination, and, as a result, it is possible to reliably return the medicine to the return destination.

In particular, when the medicine-specific information is printed in a journal as the GS1 barcode, one piece of medicine-specific information is printed in general. Therefore, it may be a useful process, when the medicine-specific information is printed in a journal in particular.

Further, the printing output control part 69 may compare at least one piece of device-specific information originally stored in the medicine sorting device 1 with at least one piece of device-specific information acquired from the return destination, and may specify the matching device-specific information as a print target for a journal.

Further, at least one piece of medicine-specific information acquired from the return destination may be stored in the RFID tag provided in the sorting cup 141 that accommodates a sorted medicine. Even when the medicine-specific information stored in the RFID tag is read by the RFID reader of the return destination, it is possible to reliably perform collation in the return destination.

(Cleaning Operation of Medicine Placement Table)

Figure 18:
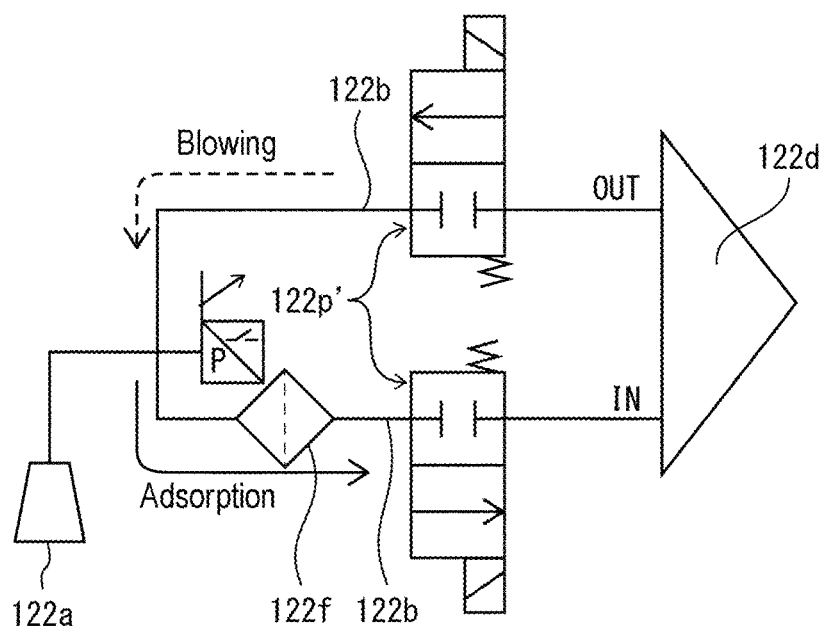
FIG. 18 is a schematic view showing an example of an adsorption mechanism provided in a conveyance/sorting unit.

Next, an example of a cleaning operation of a medicine placement table 133*a* is described. FIG. 18 is a schematic view showing an example of an adsorption mechanism provided in the conveyance/sorting unit 12. The adsorption mechanism shown in FIG. 18 has a configuration suitable for the cleaning operation of the medicine placement table 133*a*.

In the example of FIG. 18, the adsorption mechanism is provided with an electromagnetic valve 122*p*' in the middle of the air pipe 122*b* connecting the adsorption pad 122*a* to the vacuum pump 122*d*, and the electromagnetic valve controls the flow rate of the air flowing through the air pipe 122*b*. Further, as shown in FIG. 18, the adsorption mechanism includes, as the air pipe 122*b*, a first path for discharging air from the adsorption pad 122*a* and a second path for sucking air from the adsorption pad 122*a*. A filter 122*f* for collecting dusts sucked up from the adsorption pad 122*a* is provided between the adsorption pad 122*a* and the electromagnetic valve 122*p*' on the second path. The filter 122*f* is provided to be replaceable.

There is a possibility that a medicine is broken when the medicine is put into the first accommodating part 11, and that fragments or powder dust of the medicine are accommodated in the first accommodating part 11. In this case, there is a possibility that the fragments or powder dust are adhered to the medicine conveyed from the first accommodating part 11 and placed on the medicine placement table 133*a*. Further, dust or the like may be adhered to the medicine. The medicine placement table 133*a* disposed in the disposition area Ar2 becomes an imaging target of the first camera 131 in order to discriminate the type of the medicine placed on the medicine placement table 133*a*. Therefore, if a medicine with foreign matters such as powder dust adhered thereto is placed on the medicine placement table 133*a* or such foreign matters are accumulated on the medicine placement table 133*a*, there is a possibility that the contour, engraving, or the like of the medicine is not accurately read from a captured image. In this case, the foreign matters affect the discrimination of the type of the medicine performed by the discrimination part 64. Moreover, it is better to remove the foreign matters in consideration of hygiene.

Thus, in this example, the medicine placement table 133*a* is cleaned by using the conveyance/sorting unit 12. Specifically, when cleaning the medicine placement table 133*a*, the conveyance control part 61 causes the adsorption pad 122*a* to approach an inner surface of the bottom portion (inner bottom portion surface) of the medicine placement table 133*a* up to a position spaced apart from the inner bottom portion surface by a predetermined distance. In this state, the conveyance control part 61 causes the vacuum pump 122*d* to draw air. Therefore, the foreign matters in the medicine placement table 133*a* are collected by the filter 122*f* through the adsorption pad 122*a*. By this operation, the medicine placement table 133*a* is cleaned.

Here, the adsorption mechanism performs the operations of adsorbing a medicine and releasing the medicine. In case where there is a single path of the air pipe 122*b*, when performing the operation of releasing the medicine, the foreign matters collected by the filter 122*f* may flow backward and may be discharged to the outside of the adsorption mechanism. If so, the collected foreign matters are returned to the inside of the medicine sorting device 1 (including sorting cups 141).

As described above, the adsorption mechanism of this example includes, as the air pipes 122*b*, the first path for discharging air from the adsorption pad 122*a* and the second path for sucking up air from the adsorption pad 122*a*. When adsorbing foreign matters, the air drawn in by the vacuum pump 122*d* flows through the second path. When releasing the medicine, the air discharged by the vacuum pump 122*d* flows through the first path. Therefore, it is possible to avoid the situation where the foreign matters adsorbed to the filter 122*f* as described above are returned to the inside of the medicine sorting device 1.

The conveyance control part 61 moves the adsorption mechanism with respect to the entire inner bottom portion surface of the medicine placement table 133*a* by controlling the operation of the adsorption mechanism. This enables the entire internal bottom portion surface to be cleaned. Further, the conveyance control part 61 may allow only at least a portion of the inner bottom portion surface to be cleaned by analyzing an image captured by the second camera 121.

In the above description, the inner bottom portion surface of the medicine placement table 133*a* becomes the cleaning target. However, the present invention is not limited thereto, and the inner bottom portion surface of the first accommodation part 11 or the sorting cup 141 may become the cleaning target. When the sorting cup 141 becomes the cleaning target, the sorting control part 62 may perform such a process of the conveyance control part 61.

(Clogging Avoidance Operation)

The adsorption mechanism shown in FIG. 18 includes the filter 122*f*, thereby preventing foreign matters such as powder dust from entering the air pipes 122*b*, the electromagnetic valves 122*p'*, or the vacuum pump 122*d* in the subsequent stage. However, when the filter is clogged with foreign matters, it is necessary to replace the filter 122*f* with a new filter. Further, even in the adsorption mechanism shown in FIG. 5, the entering of the foreign matters may be prevented by providing a filter in the vicinity of the adsorption pad 122*a* of the air pipe 122*b*.

When a flow rate sensor (described below) is provided in the adsorption mechanism, the conveyance control part 61 (or the sorting control part 62) determines whether or not the flow rate of air in the air pipe 122*b* when a medicine is not adsorbed is equal to or lower than a predetermined flow rate. The predetermined flow rate may be set to a flow rate at which a medicine can be adsorbed (a flow rate that does not affect the adsorption of a medicine). When it is determined that the flow rate is equal to or lower than the predetermined flow rate, the conveyance control part 61 determines that the filter has been clogged. When the determination is made in this manner, the conveyance control part 61 causes the air to be discharged from the adsorption pad 122*a* by, for example, moving the adsorption mechanism onto the recovery tray 16 and controlling the adsorption mechanism. Thus, the foreign matters adhered to the filter to can be removed, and the use period of the filter (period until filter replacement) can increase.

(Contamination Detection of Medicine Placement Table)

It may be determined whether or not contamination (e.g., foreign matters) exists on the medicine placement table 133*a* by imaging the medicine placement table 133*a* by the first camera 131 in the state where no medicine is placed on the medicine placement table.

As described above with reference to FIG. 7, the medicine sorting device 1 includes the visible light radiation part (the first radiation part 134*a* and the second radiation part 134*b*) that emits visible light, and the ultraviolet light radiation part 134*c* that emits ultraviolet light. Therefore, the first camera 131 can acquire a visible light image and an ultraviolet light image. The control part determines whether or not contamination exists on the medicine placement table 133*a* by using the visible light image and the ultraviolet light image.

Here, the medicine placement table 133*a* in a new product state (that is, the medicine placement table 133*a* in a clean state) is imaged in advance, and the visible light image and the ultraviolet light image (referred to as a "reference visible light image" and a "reference ultraviolet light image", respectively) are stored in advance in the storage part 80.

For example, when staring sorting, the imaging control part 63 uses the first camera 131 to image the medicine placement table 133*a* on which no medicine is placed. The control part compares a visible light image and a ultraviolet light image (referred to as a "target visible light image" and a "target ultraviolet light image", respectively) with the reference visible light image and the reference ultraviolet light image, respectively, thereby specifying a component of the medicine sorting device 1 (a background portion) that is present in the background of the medicine placement table 133*a* in the target visible light image and the target ultraviolet light image.

Since the medicine placement table 133*a* is transparent, the background portion of the medicine placement table 133*a* is also reflected in the visible light image. Further, depending upon a material of the background portion, light may emit in the ultraviolet light image. Therefore, by comparing the reference visible light image and the target visible light image, or by comparing the reference ultraviolet light image and the target ultraviolet light image, the background portion may be removed from a contamination determination target.

The control part determines whether or not an image different from the background portion exists in the target visible light image. When it is determined that an image different from the background portion exists, the control part determines whether the size of the image is equal to or larger than a predetermined size. When it is determined that the size is equal to or larger than the predetermined size, the control part determines that the image is contamination.

Further, the control part determines whether or not light emission different from the background portion exists in the target ultraviolet light image. When it is determined that light emission different from the background portion exits, the control part determines whether or not the intensity of the light emission is equal to or greater than a predetermined magnitude. When it is determined that the intensity is equal to or greater than the predetermined intensity, the control part determines that the light emission is caused by contamination.

When it is determined that contamination exists on the medicine placement table 133*a*, the control part performs notification of prompting the cleaning of the medicine placement table 133*a* through, for example, the display part 32. Thus, by cleaning the medicine placement table 133*a*, it is possible to reduce the possibility that the contamination affects the determination of the type of a medicine by the discrimination part 64.

Further, in case of the visible light image, there is a possibility that dust cannot be recognized. Further, in case of the ultraviolet light image, dust can be easily recognized (dust tends to emit light upon being irradiated with ultraviolet light), but there is a possibility that a dark object cannot be recognized. By analyzing the visible light image and the ultraviolet light image and using the result thereof to determine the existence of contamination on the medicine placement table 133*a*, it is possible to specify various types of contamination.

Further, the predetermined size, which is the comparison target of an image size, and the predetermined intensity, which is the comparison target of light emission intensity, may be set to be large enough to allow the control part to recognize contamination that may affect the determination. Further, when the influence of the background portion is small in the determination of contamination, it is not always necessary to compare a captured image with the reference visible light image or the reference ultraviolet light image.

(Determination on Whether or not Medicine can be Adsorbed)

Next, determination on whether or not medicine can be adsorbed made by the conveyance control part 61 or the sorting control part 62 is described.

The conveyance/sorting unit 12 may include a flow rate sensor (not shown) that detects the flow rate of air flowing through the air pipe 122b of the adsorption mechanism. In this case, the conveyance control part 61 (or the sorting control part 62) can determine that the medicine is adsorbed by the adsorption pad 122a based on the change in the flow rate detected by the flow rate sensor. That is, the conveyance control part 61 can make the determination of the adsorption based on the change in the flow rate instead of the change in the suction force detected by the pressure sensor.

Even when there is a change in the medicine adsorption state (e.g., when the medicine is adsorbed or when the medicine is released from the adsorbed state), it takes time for the pressure in the air pipe 122b to change to such an extent that the change is detectable by the pressure sensor. Further, the flow rate changes in real time while following the change in the adsorption state of the medicine. Therefore, the conveyance control part 61 determines whether or not the medicine can be adsorbed, by using the flow rate sensor instead of the pressure sensor. Thus, when compared to the case of using the pressure sensor, it is possible to shorten the time spent for determining whether or not the medicine can be adsorbed.

Further, similar to the pressure sensor, the conveyance control part 61 may detect that the medicine is near up to a predetermined range from the tip portion of the adsorption mechanism based on the change in the flow rate detected by the flow rate sensor. Further, by appropriately setting a threshold value, the conveyance control part 61 may determine whether or not the adsorption mechanism is adsorbing the adsorption pad 122a itself based on the change in the flow rate. Therefore, the time can be shortened more in the determination using the flow rate sensor than the determination using the pressure sensor.

(Determination on Number of Medicines Placed on Medicine Placement Table)

Next, a process for determining the number of medicines placed on the medicine placement table 133a performed by the imaging control part 63 is described. One medicine to be discriminated by the discrimination part 64 is placed on the medicine placement table 133a. But, there is a possibility that another medicine may be placed on the medicine placement table 133a in the state where the medicine remains on the medicine placement table 133a. If two or more medicines are placed on the medicine placement table 133a, there is a possibility that the type of the medicine may not be properly discriminated by the discrimination part 64.

Thus, in this example, the imaging control part 63 determines that an error occurs when two or more medicines are placed on the medicine placement table 133a. For example, it is assumed that the imaging control part 63 determines that there are two or more medicines in an area extraction process for the surface of the medicine (the image of a medicine in the image captured from the position of θ=0°). In this case, the imaging control part 63 determines that an error occurs without performing the area extraction process for the back surface of the medicine (the image of a medicine in the image captured from the position θ=180°). In case of error occurrence, the control part may notify the fact through, for example, the display part 32, and may temporarily interrupt the medicine sorting process.

The imaging control part 63 performs determination on whether or not two or more medicines are placed on the medicine placement table 133a, for example, as follows.

First, since the brightness of a medicine in an image varies due to the color given to the medicine, the imaging control part 63 extracts a plurality of areas in an image captured by the first camera 131 based on a luminance distribution. For example, when the areas are classified based on three types of luminance distributions, a first luminance threshold value and a second luminance threshold value are set in advance. In this case, the imaging control part 63 classifies the areas into an area R (A) having a luminance equal to or higher than the first luminance threshold value, an area R (B) having a luminance lower than the first luminance threshold value and equal to or higher than the second luminance threshold value, and an area R (C) having a luminance lower than the second luminance threshold value.

Next, the imaging control part 63 performs a narrowing-down process on the image based on a shape feature amount. The shape feature amount is a feature amount set in advance to remove an image of an object that is not a medicine. An example of the shape feature amount may include an area assumed as a medicine and the degree of indentations (a jagged degree or a convexity degree) of the edge portion. The imaging control part 63 extracts only an area estimated as a medicine by removing an area not estimated as a medicine from the image by referring to the shape feature amount and removing an area not estimated as a medicine from the image.

Next, the imaging control part 63 extracts only one of the area R (A), the area R (B), and the area R (C) in the areas estimated as medicines. Here, the area R (A) is estimated to be an area corresponding to a medicine with a relatively bright color, the area R (C) is estimated to be an area corresponding to a medicine with a relatively dark color, and the area R (B) is estimated to be an area corresponding to a medicine with an intermediate color.

When the area R (A) and the area R (B) are extracted from the image, the imaging control part 63 determines that the area is an area corresponding to a medicine with a relatively bright color, and extracts the area R (A). When the area R (B) and the area R (C) are extracted from the image, the imaging control part 63 determines that the area is an area corresponding to a medicine with a relatively dark color, and extracts the area R (C). When the area R (A), the area R (B), and the area R (C) are extracted from the image, the imaging control part 63 determines that the area is an area corresponding to the medicine with the intermediate color, and extracts the area R (B).

The imaging control part 63 extracts one of the area R (A), the area R (B), and the area R (C), and then performs a dividing process based on the luminance distribution (e.g., a process using a known Watershed algorithm) on the extracted areas. Therefore, if there is an area that can be divided based on luminance distributions in the extracted area, the area is divided into two or more areas.

Then, the imaging control part 63 determines that the finally obtained areas are areas corresponding to the medicine, and counts the number of the areas. When the number is two or more, the imaging control part 63 determines that an error occurs.

Figure 19:
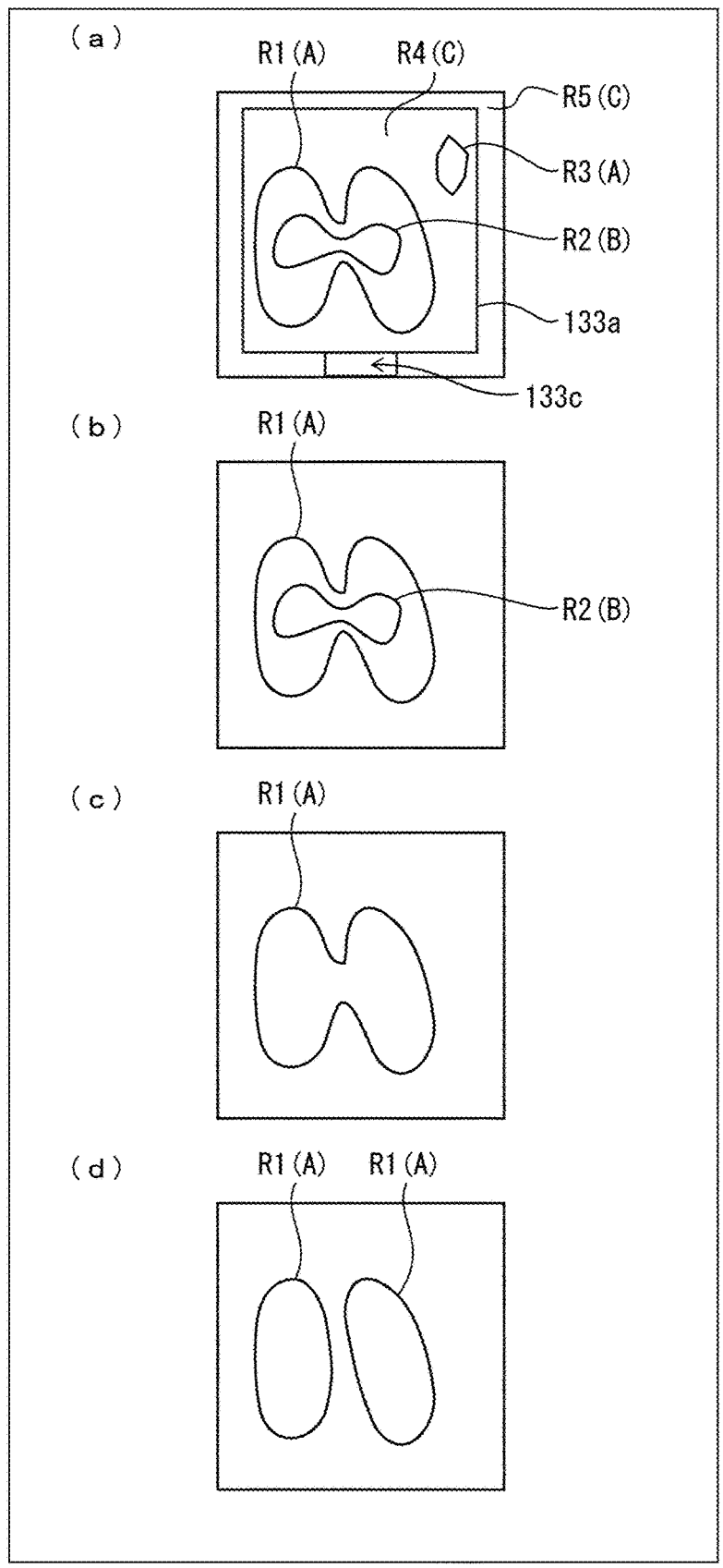
FIG. 19 ((a) to (d) of FIG. 19) is a view illustrating an example of determination of the number of medicines placed on a medicine placement table, and is an image captured by a first camera.

In FIG. 19, (a) to (d) of FIG. 19 are views illustrating an example of the above-described number determination process, and is an image captured by the first camera 131.

In the example of (a) of FIG. 19, the imaging control part 63 extracts an area R1 (A) and an area R3 (A) as the area R (A), extracts an area R2 (B) as the area R (B), and extracts an area R4 (C) and an area R5 (C) as the area R (C).

Next, as shown in (b) of FIG. 19, by referring to the shape feature amount, the imaging control part 63 excludes the R3 (A), the area R4 (C), and the area R5 (C) that clearly differ from the shape of the medicine, and extracts the R1 (A) and the R2 (B) from which the shape of the medicine can be extracted.

Next, since the extracted areas are the area R1 (A) and the area R2 (B), the imaging control part 63 extracts the area R1 (A), as shown in (c) of FIG. 19. The imaging control part 63 performs the dividing process based on a luminance distribution on the extracted area R1 (A). In the example of FIG. 19, as shown in (d) of FIG. 19, the imaging control part 63 extracts two areas R1 (A). That is, in this case, the imaging control part 63 determines that two medicines are placed on the medicine placement table 133*a*, and determines that an error occurs.

Therefore, only when one medicine is placed on the medicine placement table 133*a*, the discrimination part 64 is allowed to perform the discrimination process. That is, it is possible to safely perform the medicine sorting process.

(Reservation Setting)

Further, the display control part 67 may display, on the display part 32, a setting image for receiving a user input for reserving a medicine sorting start time. In this case, the control part starts the sorting process of the medicines accommodated in the first accommodating part 11 when the set sorting start time is due. Therefore, since it is possible to set the medicine sorting device 1 to a sleep mode (an eco mode) until the sorting operation starts, it is possible to reduce the power consumption of the medicine sorting device 1. Further, in general, the electric charges are cheaper at night than in daytime. Therefore, when the sorting start time is set such that the medicine sorting process is performed at night, it is possible to further reduce the electric charges.

(Brought Medicine Discrimination and Repackaging Process)

Next, a brought medicine discrimination and repackaging process performed by the medicine sorting device 1 is described. For example, when receiving a patient who has attended to or has been hospitalized to other hospital, the hospital or pharmacy, which received the patient, discriminates medicines prescribed at the other hospital or pharmacy (i.e., brought medicines) In this case, it is necessary to unwrap a packaging paper brought by the patient, perform visual inspection of the brought medicines, and then perform re-packaging based on the examination result from a physician. The medicine sorting device 1 may be used for the visual inspection and repackaging for the brought medicines.

For example, the user unwraps a packaging paper brought by any one patient, and stores the brought medicines, which are contained in the packaging paper, into the first accommodating part 11. The medicine sorting device 1 sorts the medicines stored in the first accommodating part 11 into the second accommodating part 14. Thereafter, visual inspection is performed by the user. Further, the physician's examination result for the patient is received, and prescription information related to the patient is input. The packaging mechanism 6 of the medicine sorting device 1 repackages the brought medicines accommodated in the second accommodating part 14 based on the input prescription information.

Since the prescription information has been input, new medicines that are not included in the brought medicines may be added and packaged. Further, medicines, which have been included in the brought medicines but not input in the prescription information, may not be packaged.

(Determination on Whether or not Master Image is Distributable)

Next, a process for determining whether or not a master image is distributable, which is performed by a management device, is described. After a returned medicine is imaged by the first camera 131, the medicine sorting device 1 may register an image subjected to the visual inspection as a master image in association with a medicine name. Further, when medicine sorting devices 1 are installed in a plurality of places (e.g., hospitals), a master image registered in a medicine sorting device 1 installed in any place may be distributed to a medicine sorting device 1 installed in other places. However, if the master image is distributed to other medicine sorting device 1 without confirming the reliability thereof, there is a possibility that such a medicine sorting device 1 erroneously determines the type of the medicine.

Thus, in this example, master images are collected from a plurality of medicine sorting devices 1, and a management device (not shown), which can distribute the master images to a plurality of medicine sorting devices 1, determines whether or not the master images are distributable. The management device determines whether or not a master Image is distributable from, for example, the following four viewpoints:

(A1) Registration date of the master image;

(A2) Number of returns to a medicine sorting device 1;

(A3) The first day of return for the first return to a tablet packaging device or powder medicine packaging device; and (A4) The last date of return of the last return to the tablet packaging device or powder medicine packaging device. The information of above items (1) to (4) are managed by the medicine sorting device 1, and are transmitted to the management device in association with the registered master image.

Upon receiving the master image from the medicine sorting device 1, the management device determines, for example, the following:

(B1) Whether a predetermined number of days has elapsed from the registration date;

(B2) Whether the number of returns has reached a predetermined number;

(B3) Whether a predetermined number of days has elapsed from the first day of return; and (B4) Whether a predetermined number of days has elapsed from the last day of return.

Regarding item (B1), when the predetermined number of days has not elapsed from the registration date, there is a high possibility that the number of times of using the master image in the medicine sorting device 1 (that is, the number of times for visual inspection, in other words, a use record) is small. Thus, it may be determined that the master image has low reliability. For this reason, when the predetermined number of days has not elapsed from the registration date, the management device excludes the master image from distribution target master images.

Regarding item (B2), when the number of returns has not reached the predetermined number, the use record of the master image is low, and thus it may be determined that the master image has low reliability. For this reason, when the number of returns does not reach the predetermined number, the management device excludes the master image from distribution target master images.

Regarding item (B3), when the predetermined number of days has not elapsed from the first day of return, even if the use record of the master image is high (even if the number of returns has reached the predetermined number), it may be determined that the master image has been erroneously registered in the subsequent visual inspection. Therefore, in order to prove the reliability of the master image, the management device excludes the master image from the distribution target master images when the predetermined number of days have not elapsed from the first date of return.

Regarding item (B4), when the predetermined number of days have elapsed from the last date of return, the master image has not been used for a while after it was last returned to the tablet packaging device or powder medicine packaging device. Thus, it may be determined that the master image is short of reliability. For this reason, when the predetermined number of days has elapsed from the last date of return, the management device excludes the master image from distribution target master images.

Thus, by determining whether or not the master image is distributable as described above, it is possible to distribute a highly reliable master image to the medicine sorting devices 1.

Further, the predetermined numbers of days in items (B1), (B3), and (B4) may be set based on experience or the like from the viewpoint of a use record, and the predetermined numbers of days in items (B1), (B3), and (B4) are set to be different from each other. Further, the predetermined number of days in item (B2) is set in the same manner.

<Process Example from Medicine Sorting to Medicine Return>

Hereinafter, a process example from medicine sorting to medicine return (an example of a medicine return method) is described. FIG. 20 is a view showing an example of a processing flow from medicine sorting to medicine return. In this example, it is assumed that a plurality of types of medicines are sorted by each type in the medicine sorting device 1.

As shown in FIG. 20, when a plurality of types of medicines are input into the first accommodating part 11, the medicine sorting device 1 sorts and stores each type of medicines in each sorting cup 141 of the second accommodating part 14 (medicine sorting step).

Thereafter, the medicine sorting device 1 displays, on the touch panel 3, an inspection image Im2 for performing visual inspection on the medicines sorted by the medicine sorting device 1 (display step). That is, the user performs visually inspection on the medicines sorted by the medicine sorting device 1 by using the inspection image Im2 displayed on the touch panel 3 (inspection step).

Thereafter, the medicine sorting device 1 performs a process for enabling the medicines after the visual inspection to be returned to a packaging device 200 or a medicine shelf 300, which is the return destination, based on the visual inspection result using the inspection image Im2 (return preparation step). That is, the user returns the medicines after the visual inspection to the packaging device 200 or the medicine shelf 300 based on the visual inspection result (inspection result) (return step). Further, the packaging device 200 may be, for example, a tablet packaging device or a powder medicine packaging device.

Through the above steps, it is possible to return the medicines sorted by the medicine sorting device 1 to the packaging device 200 or the medicine shelf 300, which is the return destination, through the visual inspection made by the user.

Figure 22:
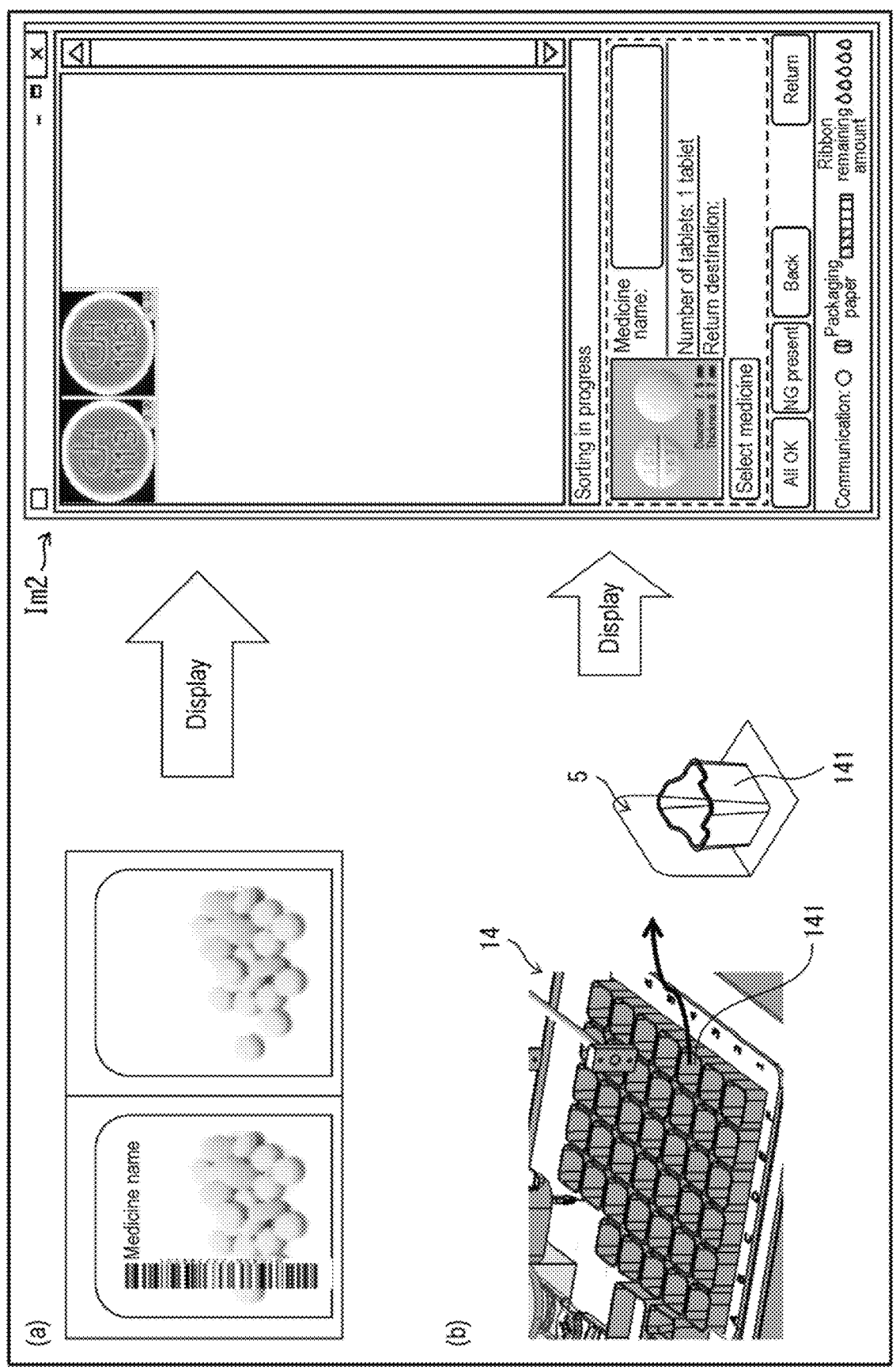
FIG. 22 ((a) and (b) of FIG. 22) is a view showing an example of an inspection image display method.

Next, a method of displaying the inspection image Im2 is described with reference to FIGS. 21 and 22. FIG. 21 and (a) and (b) of FIG. 22 are views showing an example of a method of displaying the inspection image Im2.

The medicine sorting device 1 may stop the medicine sorting operation at any timing. For example, when a user input for stopping the sorting operation is received, or when the sorting of the medicines stored in the first accommodating part 11 into the second accommodating part 14 is completed, the medicine sorting device 1 stops the sorting operation. When the medicine sorting device 1 stops the sorting operation (e.g., when it is determined that the medicine sorting operation has been completed), the medicine sorting device 1 displays a sorting image Im1 indicating the medicine sorting state as shown in FIG. 21. Further, the medicine sorting device 1 may display the sorting image Im1 during the sorting operation.

Each of a plurality of sorting positions where the medicines are sorted, the sorting cups 141 disposed at the sorting positions, and the medicine data related to the medicines stored in the sorting cups 141 are stored in the storage part 80 and the RFID tags provided in the sorting cups in association with one another. Therefore, the medicine sorting device 1 can display the sorting image Im1 that reflects the plurality of sorting positions in the second accommodating part 14 and the sorting state at each sorting position (e.g., the number of stored medicines).

As shown in FIG. 21, the medicine sorting device 1 displays, on the touch panel 3, a medicine inspection image Im2 associated with the sorting position, by receiving a user input on a sorting position shown in the sorting image Im1. Therefore, the inspection image Im2 of the medicines on which the user desires to perform visual inspection can be displayed.

Further, the medicine sorting device 1 performs sorting until the medicines stored in the first accommodating part 11 are exhausted. When the number of sorting cups 141, which are can be disposed in the second accommodating part 14, is, for example, forty, the medicine sorting device 1 can store 40 types of medicines in the second accommodating part 14. When 41 or more types of medicines are stored in the first accommodating part 11, the medicine sorting device 1 cannot sort all the medicines into the second accommodating part 14. Therefore, when the medicines are sorted into all the sorting cups 141 disposed in the second accommodating part 14, the medicine sorting device 1 sorts the 41st and subsequent types of medicines into the standby tray 15.

In this case, in order to make a sorting cup 141 accommodate the medicines stored in the standby tray, the medicine sorting device 1 may take out the medicines accommodated in any sorting cup 141, and may package the medicines by the packaging mechanism 6. For example, a sorting cup 141, in which sorting-completed medicine is accommodated, becomes a target for automatic packaging performed by the packaging mechanism 6.

Further, in the medicine sorting device 1, the user can perform visual inspection on the medicines stored in the sorting cup 141 at any timing. The medicine sorting device 1 may determine that sorting has been completed for the medicines on which the visual inspection has been performed, and may take the medicines after the completion of visual inspection as a target to be taken out or packaged. Therefore, when visual inspection has been performed on the medicines stored in the sorting cup 141 even during the sorting of medicines, the medicine sorting device 1 determines that the sorting of the medicine has been completed, and may take such medicines as a target for automatic packaging performed by the packaging mechanism 6, as described above. However, the medicine sorting device 1 temporarily stops the medicine sorting process when performing the medicine packaging process.

As shown in (a) of FIG. 22, the packaging mechanism 6 packages the medicines that become the target for automatic packaging, and then provides a barcode for reading the inspection image Im2 to the packaging paper. The barcode includes, for example, medicine data related to the medicines.

When the sorted medicines are packaged, the user causes a barcode reader (not shown) to read the medicine data related to the medicines included in the barcode provided to the packaging paper. The medicine sorting device 1 uses the medicine data related to the medicines read by the bar code reader to read image data stored in the storage part 80 in association with the medicine data, thereby displaying the inspection image Im2 of the medicines on the touch panel 3.

Further, as shown in (b) of FIG. 22, the medicine sorting device 1 may display the inspection image Im2 by using data stored in the RFID tag provided in the sorting cup 141. In this case, the user takes out the sorting cup 141, which accommodates the medicines to be returned to a return destination, and places the sorting cup 141 on the first RFID reader/writer unit 5. The medicine sorting device 1 uses the medicine data related to the medicines read by the first RFID reader/writer unit 5 to read image data stored in the storage part 80 in association with the medicine data, thereby displaying the inspection image Im2 of the medicines on the touch panel 3. When the image data is included in the RFID tag, the inspection image Im2 may be displayed on the touch panel 3 by using the image data.

Thus, the inspection image Im2 of the medicines on which the user desires to perform visual inspection may be displayed by the method shown in FIG. 22.

Figure 23:
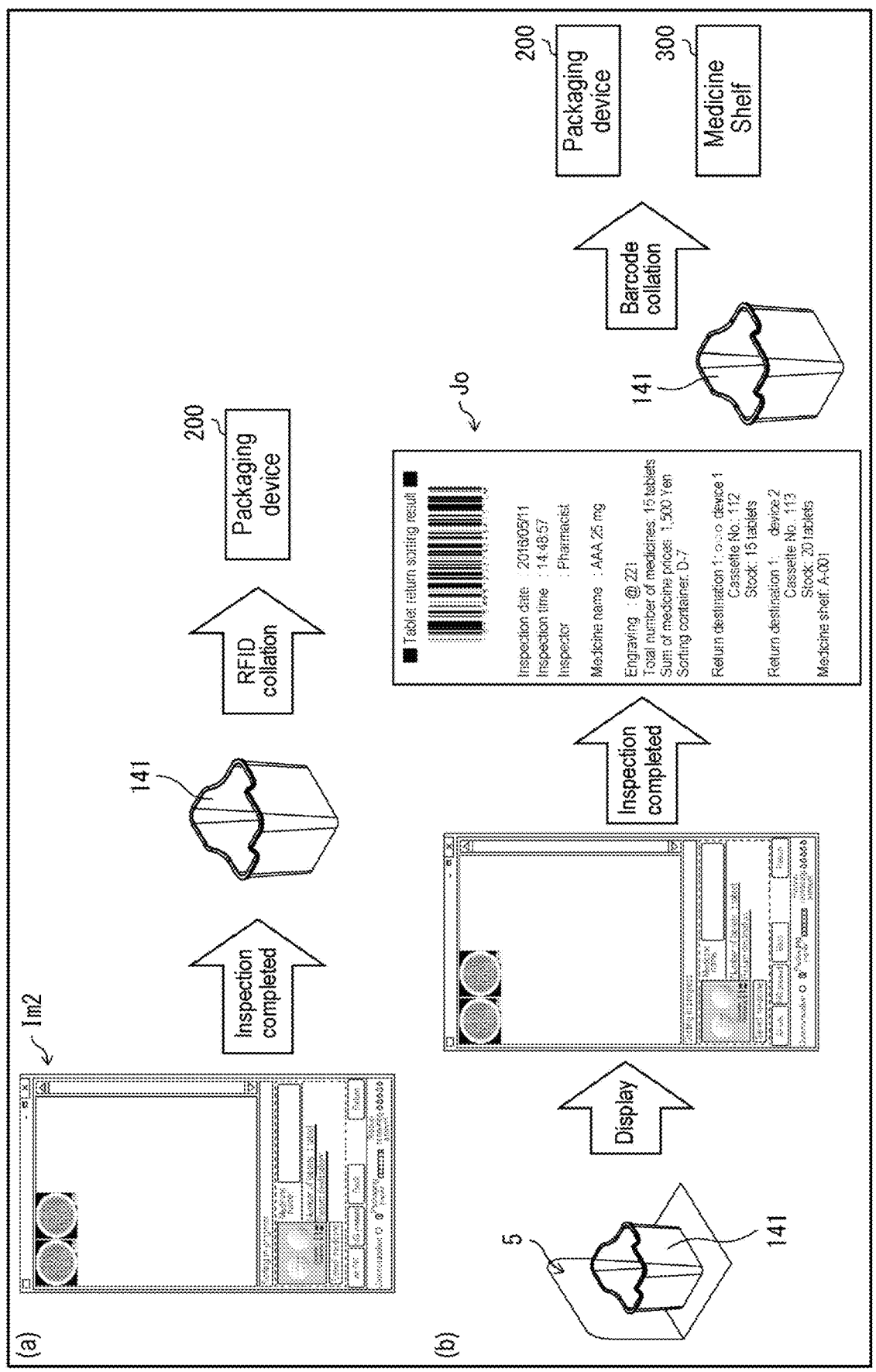
FIG. 23 ((a) and (b) of FIG. 23) is a view showing an example of a return method after completion of visual inspection.
Figure 24:
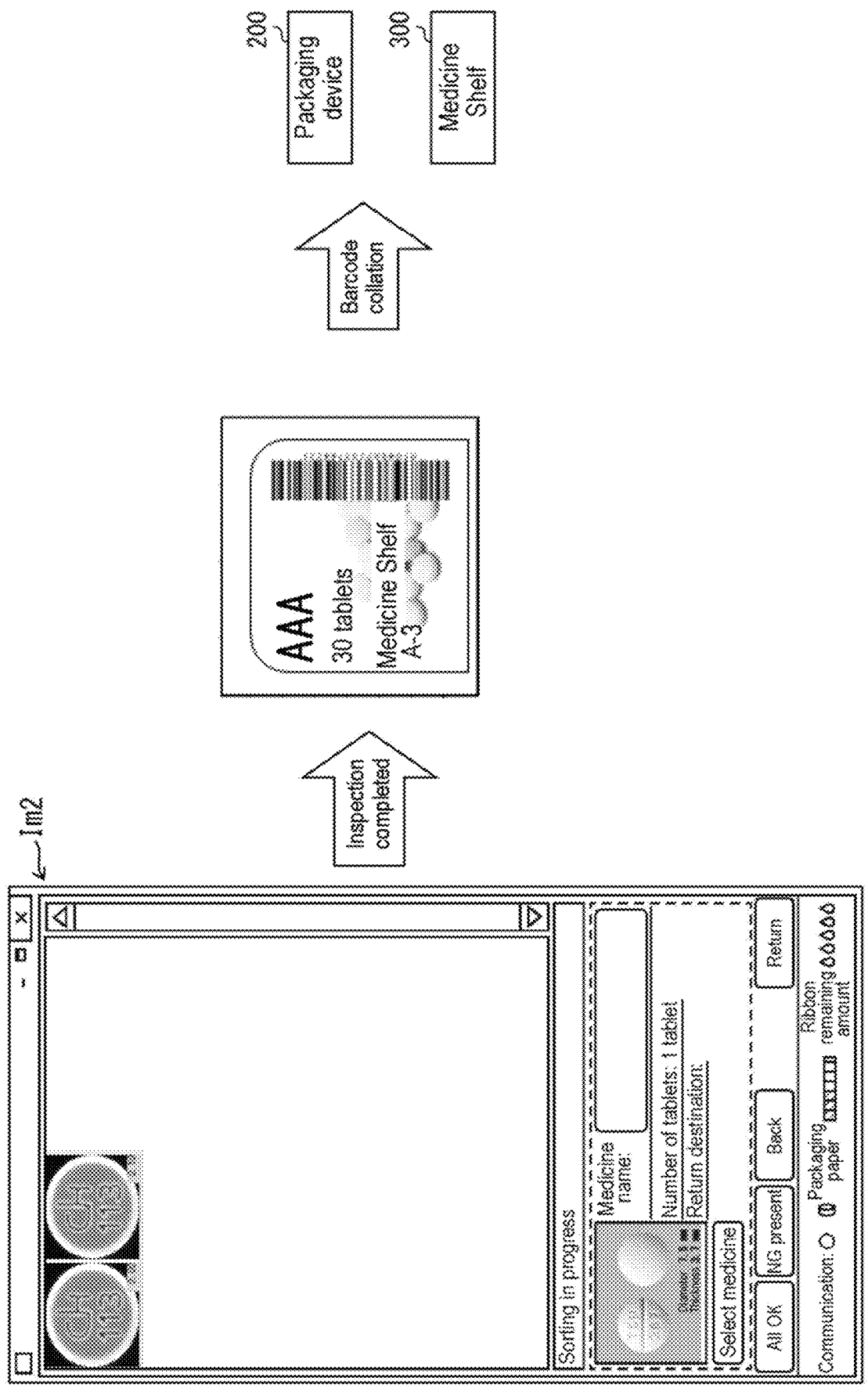
FIG. 24 is a view showing an example of a return method after completion of visual inspection.

Next, a return method after completion of visual inspection is described with reference to FIGS. 23 and 24. FIG. 23 ((a) and (b) of FIG. 23) and FIG. 24 are views showing an example of a return method after completion of visual inspection.

When the packaging device 200, which is a return destination, is provided with a function of reading data stored in the RFID tag provided in a sorting cup 141, for example, the return method is performed as shown in (a) of FIG. 23.

Specifically, the medicine sorting device 1 displays the inspection image Im2 based on a user input or a user manipulation. The user performs the visual inspection on the medicines accommodated in any sorting cup 141 by confirming the inspection image Im2. After the visual inspection is completed, the user performs a user input indicating the completion of visual inspection on the medicine sorting device 1. The medicine sorting device 1 receives the user input, and stores data related to the medicines, for which the visual inspection result has been determined, in the RFID tag of the sorting cup 141.

Thereafter, the user carries the sorting cup 141 to the packaging device 200, and causes an RFID reader (not shown) provided in the packaging device 200 to read the data related to the medicines and stored in the RFID tag of the sorting cup 141. Therefore, the user can allow the medicines accommodated in the sorting cup 141 to be accommodated (returned) into a cassette (not shown) which is provided in the packaging device 200 and accommodates the medicines. At this time, when the cassette of the packaging device 200 is provided with a lid with a lock, the cassette lock of the packaging device 200 may be made to be unlocked on the condition of confirming that the inspection result (indicating that all the visual inspection of the sorting cup 141 are OK) is stored as the result of visual inspection stored in the RFID tag of the sorting cup 141, that is, as the result of the user's visual inspection on the inspection image Im2 sorted based on the information that is indicated by an engraving or print of the medicines and is definitely recognized by the device (engraving information or print information).

Further, when the packaging device 200 (a return destination) is not provided with a function of reading data stored in the RFID tag provided in a sorting cup 141, or when the return destination is a medicine shelf 300, the return method is performed, for example, as shown in (b) of FIG. 23.

Specifically, the user places a sorting cup 141 to be visually inspected on the first RFID reader/writer unit 5. Therefore, the medicine sorting device 1 displays the inspection image Im2 based on data related to the medicines stored in the RFID tag of the sorting cup 141. Thereafter, the user performs a visual inspection on the medicines accommodated in the sorting cup 141 by confirming the inspection image Im2. After the visual inspection is completed, the user performs a user input indicating the completion of visual inspection on the medicine sorting device 1. The medicine sorting device 1 receives the user input, and issues a journal Jo in which medicine data, return destination information, and the like related to the medicines are printed reflecting the visual inspection result.

Thereafter, when the return destination is a packaging device 200, the user carries the sorting cup 141 and the journal Jo to the packaging device 200. Then, the user causes a barcode reader (not shown) provided in the packaging device 200 to read medicine data related to the medicines included in the barcode printed in the journal Jo. Therefore, the user can allow the medicines accommodated in the sorting cup 141 to be accommodated (returned) into the cassette (not shown) which is provided in the packaging device 200 and accommodates the medicines. At this time, when the cassette of the packaging device 200 is provided with a lid with a lock, the cassette lock of the packaging device 200 may be made to be unlocked on the condition of confirming that the inspection result (indicating that all the visual inspection of the sorting cup 141 are OK) is included as the result of the visual inspection included in the barcode printed in the journal Jo, that is, as the result of the user's visual inspection on the inspection image Im2 sorted based on the information that is indicated by an engraving or print of the medicines and is definitely recognized by the device (engraving information or print information).

Further, when the return destination is a medicine shelf 300, the user causes a reading part (e.g., a barcode reader) provided in the above-described return assisting device to read the medicine data and return destination information related to the medicines and included in the barcode printed in the journal Jo. Therefore, the user may carry the sorting cup 141 and the journal Jo to the medicine shelf 300 (the return destination), and can allow the medicines accommodated in the sorting cup 141 to be accommodated (returned) at a predetermined position in the medicine shelf 300. At this time, when the medicine shelf 300 is provided with a door with a lock, the door lock of the medicine shelf 300 may be made to be unlocked on the condition of confirming that the inspection result (indicating that all the visual inspection of the sorting cup 141 are OK) is included as the result of the visual inspection included in the barcode printed in the journal Jo, that is, as the result of the user's visual inspection on the inspection image Im2 sorted based on the information that is indicated by an engraving or print of the medicines and is definitely recognized by the device (engraving information or print information).

Further, when the medicines packaged by the packaging mechanism 6 are returned to the packaging device 200 or the medicine shelf 300, for example, the return method is performed as shown in FIG. 24. For example, as described above, when the medicines are accommodated in all the sorting cups 141 disposed in the second accommodating part 14 and the medicines are accommodated in the standby tray 15, the medicines in the sorting cups 141 are taken out, and the medicines in the standby tray 15 are accommodated in the sorting cups 141. In this case, the medicines taken out from the sorting cups 141 are packaged by the packaging mechanism 6.

As in (a) of FIG. 23, after the visual inspection is completed, the user performs a user input indicating the completion of visual inspection on the medicine sorting device 1. The medicine sorting device 1 receives the user input, and stores data, which is related to the medicines and reflects the visual inspection result, in the RFID tag of the sorting cup 141 and the storage part 80.

Thereafter, the medicine sorting device 1 performs the packaging of the medicines by the packaging mechanism 6 by using the data that is related to the medicine and stored in the RFID tag or the storage part 80. At this time, the medicine sorting device 1 provides medicine data and/or return destination information related to the medicines to the packaging paper that packages the medicines, for example, in a barcode format. As in (b) of FIG. 23, the user causes the barcode reader provided in the packaging device 200 or the reading part provided in the return assisting device to read the medicine data and/or return destination information related to the medicines and included in the barcode printed on the packaging paper. Therefore, the user can allow the medicines accommodated in the sorting cup 141 to be accommodated (returned) into the cassette of the packaging device 200 or at a predetermined position of the medicine shelf 300. At this time, when the cassette lid of the packaging device 200 or the medicine shelf 300 has a door with a lock mechanism therein, the cassette lock of the packaging device 200 or the door lock of the medicine shelf 300 may be made to be unlocked on the condition of confirming that the inspection result (indicating that all the visual inspection of the sorting cup 141 are OK) is included as the result of the visual inspection included in the barcode printed in the packaging paper, that is, as the result of the user's visual inspection on the inspection image Im2 sorted based on the information that is indicated by an engraving or print of the medicines and is definitely recognized by the device (engraving information or print information).

(Example of Journal)

Next, an example of a journal issued by the medicine sorting device 1 is described with reference to FIG. 25. In FIG. 25, (a) and (b) of FIG. 25 are views showing an example of a journal. An example of a journal Jo1, which is issued by receiving a visual inspection result that all the medicines accommodated in any sorting cup 141 are the same type, is shown in (a) of FIG. 25. The visual inspection result in this case is referred to as "Inspection OK". An example of a journal Jo2, which is issued by receiving a visual inspection result that the type of at least one of the medicines accommodated in any sorting cup 141 is different from the type of the other medicines, is shown in (b) of FIG. 25. The visual inspection result in this case is referred to as "Inspection NG".

As shown in (a) of FIG. 25, when the visual inspection result is "Inspection OK", a barcode and character information are printed in the journal Jo1 as information on medicines indicating the visual inspection result. The information included in the barcode may include, for example, device-specific information for specifying a medicine sorting device 1, or the number of medicines accommodated in a sorting cup 141, in addition to the medicine-specific information (medicine identification code).

The device-specific information or information on the number of medicines is written in the journal Jo1. Thus, when returning (charging) the medicines to the packaging device 200, it is possible to read the above information at the packaging device 200. When the device-specific information is written, it is possible to discriminate which medicine sorting device 1 sorts the medicines at the packaging device 200.

The character information printed in the journal Jot may include, for example, respective pieces of information indicating an inspection date and time, an inspector's name, a medicine name, an engraving engraved on a medicine, the total number of medicines accommodated in a sorting cup 141, the total price of the medicine, and container-specific information for identifying a sorting cup 141, and a return destination.

As shown in (a) of FIG. 25, a plurality of return destinations as return candidates are printed in the journal Jo1. Specifically, the types of packaging devices 200 as return destinations, the device numbers of the packaging devices 200, and the cassette numbers of cassettes provided in the packaging devices 200 are printed. Further, the shelf number of a medicine shelf 300 is printed.

As shown in (b) of FIG. 25, when the visual inspection result is "Inspection NG", a barcode and character information are printed in the journal Jo2 as information on the medicine indicating the visual inspection result, but the journal Jo2 differs from the journal Jo1 in the following points.

Since the journal Jo2 is issued when a "Inspection NG" medicine (a type of a medicine different from other medicines) is accommodated in a sorting cup 141, the number of medicines accommodated in the sorting cup 141 is not included as information included in the barcode. In this case, it is impossible to specify the number of medicines to be returned at the packaging device 200. For this reason, in the journal Jo2, a text, which prompts the user to count the number of medicines (medicines for which the visual inspection result is OK) remaining after removal of the medicine for which the visual inspection result is NG (medicines of the "Inspection NG") and prompts the user to input the counted number, is printed. Further, in the journal Jo2, instead of the total number of medicines printed in the journal Jo1, the number of medicines for which the visual inspection result is OK (the number of medicines having Inspection OK), and the number of medicines for which the visual inspection result is NG (the number of medicines having Inspection NG) are printed. Further, in the journal Jo2, as shown in (b) of FIG. 25, the characters "Inspection NG" are printed such that the visual inspection result can be understood at a glance.

Further, the bar code is also provided in the packaging paper in the return method shown in FIG. 24. The barcode provided in the packaging paper may be the above-described barcode. That is, regarding the barcode provided in the packaging paper, the information included in the barcode may be different depending upon whether the inspection result is "Inspection OK" or "Inspection NG".

(Example of Display Image: Sorting Image and Inspection Image)

Next, examples of display images are described with reference to FIGS. 26 to 29.

Figure 27:
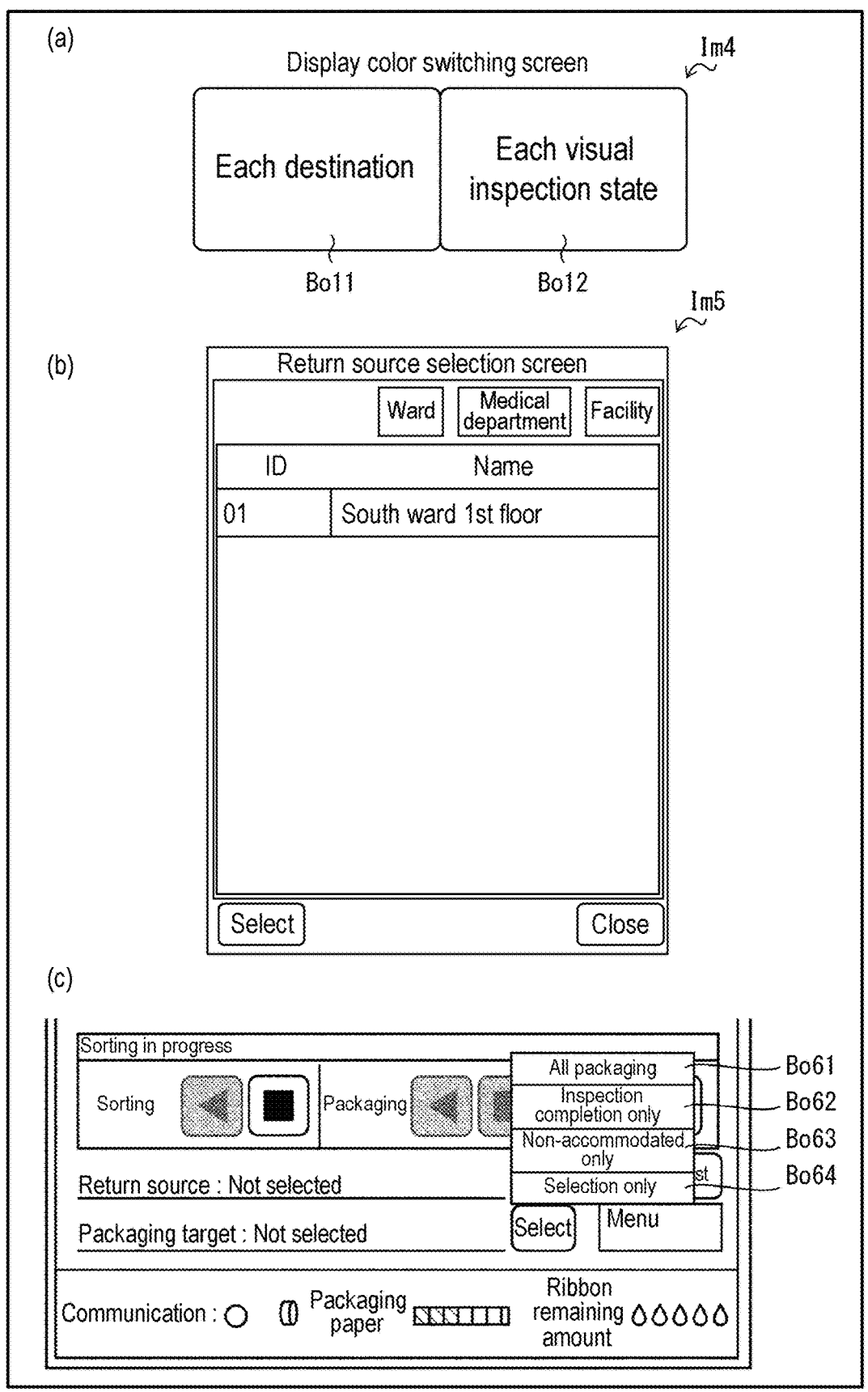
FIG. 27 ((a) to (c) of FIG. 27) is a view showing an example of an image that are displayed when a user input on a sorting image is received.

FIG. 26 shows, in (a) of FIG. 26, an example of a sorting image Im1, and shows, in (b) of FIG. 26, an example of a sorted medicine list image Im3 showing information related to sorted medicines. The sorting image Im1 shown in (a) of FIG. 26 is another example of the display image shown in (b) of FIG. 11. In the sorting image Im1 shown in (a) of FIG. 26, the lower configuration is mainly different from the display image shown in (a) of FIG. 11. Here, in the sorting image Im1, portions different from the display image shown in (a) of FIG. 11 is mainly described. In FIG. 27, (a) to (c) of FIG. 27 are views showing examples of images that are displayed upon receiving a user input for the sorting image Im1.

In the sorting image Im1, a plurality of rectangular portions Rs corresponding to the sorting cups 141 disposed in the second accommodating part 14 can receive a user input. A medicine sorting device 1 displays an inspection image Im2 (see (a) of FIG. 28) corresponding to a rectangular portion Rs in response to a user input on the rectangular portion Rs. Further, as in (a) of FIG. 11, the medicine sorting device 1 displays the number of sorted medicines in the rectangular portion Rs corresponding to the sorting cup 141 into which the medicines are sorted.

A "display switching" button Bo1 is a manipulation button for receiving a user input for selecting a color-coding method for the rectangular portions Rs. When the medicine sorting device 1 receives a user input on the "display switching" button Bo1, a display color switching image Im4 showing the color-coding method as shown in (a) of FIG. 27 is displayed in a pop-up manner.

The display color switching image Im4 includes, for example, a "color-coding for each return destination" button Bo11 and a "color-coding for each visual inspection state" button Bo12. The "color-coding for each return destination" button Bo11 is a manipulation button for receiving a user input for color-coding for each return destination. The "color-coding for each visual inspection state" button Bo12 is a manipulation button for receiving a user input for color-coding for each visual inspection state.

In case where there is a user input on the "color-coding for each return destination" button Bo11, for example, when the medicine sorting device 1 determines the medicine name of the medicines stored in a sorting cup 141, the color-coding of the rectangular portions Rs is performed by referring to return destination information associated with medicine data related to the medicines. Further, the medicine sorting device 1 displays a rectangular portion Rs, for which the medicine name is not discriminated, and a rectangular portion Rs corresponding to the sorting cup 141, in which no medicine is accommodated, with colors different from the case of discrimination the medicine name. The rectangular portion Rs, for which the medicine name is not discriminated, and the rectangular portion Rs corresponding to the sorting cup 141, in which no medicine is accommodated, may be displayed with different colors. The display example of the rectangular portions Rs for each return destination includes the above-described display image shown in FIG. 12.

When there is a user input on the "color-coding for each visual inspection state" button Bo12, for example, the medicine sorting device 1 displays the following with different colors: (1) a rectangular portion Rs having a visual inspection result of "Inspection OK"; (2) a rectangular portion Rs having a visual inspection result of "Inspection NG"; and (3) a rectangular portion Rs for non-visual inspection. FIG. 26 shows, in (a) of FIG. 26, an example of the sorting image Im1 in which color-coding is done for each visual inspection state. Further, at least one of the three types of visual inspection states may be displayed with a color different from the other visual inspection states.

Further, the sorting image Im1 includes a "sorting" button Bo3 that receives a user input for starting and stopping sorting performed by the medicine sorting device 1, and a "packaging" button Bo4 that receives a user input for starting and stopping packaging performed by the packaging mechanism 6.

This embodiment may have a specification in which the medicine sorting process by the medicine sorting device 1 and the packaging process by the packaging mechanism 6 cannot be performed simultaneously. In case of such a specification, as shown in (a) of FIG. 26, for example, when the medicine sorting process is in progress, the "packaging" button Bo4 becomes inactive (only a button for stopping sorting (square button) becomes active). Further, when the packaging process is in progress, the "sorting" button Bo3 becomes inactive (only a button for stopping the packaging (square button) becomes active). Further, when the medicine sorting device 1 does not include the packaging mechanism 6, the "packaging" button Bo4 may not be displayed.

Further, a "return source selection" button Bo5 is a manipulation button for receiving a user input for selecting a medicine return source. The return source is a place in which the medicines have been stored before being put into the medicine sorting device 1, and is, for example, a ward, a medical department, or a facility (e.g., a medical institution). When a user input on the "return source selection" button Bo5 is received, the medicine sorting device 1 displays, for example, a return source selection image Im5 shown in (b) of FIG. 27. For example, when a medicine sorting device 1 is linked to the packaging device 200 (connected to be communicable), the medicine sorting device 1 may acquire information specifying a ward or the like (e.g., a ward ID) equipped with the packaging device 200. Therefore, the medicine sorting device 1 may store the information specifying the ward ID or the like in the storage part 80 or the RFID tag of a sorting cup 141 in association with the medicine data related to the medicines put thereto.

When a return source displayed in the return source selection image Im5 shown in (b) of FIG. 27 is selected, the selected return source is displayed on a return source shown in (a) of FIG. 26 (displayed as "unselected" in the figure).

A "packaging target selection" button Bo6 is a manipulation button for receiving a user input for selecting a medicine packaging method performed by the packaging mechanism 6. When receiving a user input on the "packaging target selection" button Bo6, the medicine sorting device 1 performs, for example, pop-up display as shown in (c) of FIG. 27. In the example of (c) of FIG. 27, the following is displayed: (1) an "all packaging" button Bo61 for packaging all sorted medicines; (2) a "inspection completion only" button Bo62 for packaging only the medicines on which visual inspection has been completed among all the sorted medicines by the packaging mechanism 6; (3) a "non-accommodated only" button Bo63 for packaging only the non-accommodated medicines in a return destination among all the sorted medicines by the packaging mechanism 6; and (4) a "selection only" button Bo64 for packaging only the medicines accommodated in the sorting cup 141 individually selected by the user among all the sorted medicines by the packaging mechanism 6. In accordance with the user's selection, a selected packaging method is displayed in a packaging method shown in (a) of FIG. 26 (displayed as "unselected" in the figure). Further, return destination information may be associated with medicine data related to sorted medicines. In this case, a user input on the "packaging target selection" button Bo6 may be applied only to the rectangular portion Rs corresponding to a sorting cup 141 accommodating the medicines whose return destination is the packaging mechanism 6 indicated by the return destination information.

A "sorting list" button Bo7 is a manipulation button for switching the display image from the sorting image Im1 to the sorting medicine list image Im3. When there is a user input on the "sorting list" button Bo7, the medicine sorting device 1 is switched to display the sorted medicine list image Im3.

As shown in (b) of FIG. 26, the sorted medicine list image Im3 shows the history of sorting by the medicine sorting device 1 for each medicine type. To make it possible to create the sorted medicine list image Im3, medicine data related to medicines, container-specific information for specifying a sorting cup 141, the number of medicines accommodated in the sorting cup 141, return destination information, and the like are stored in association with one other in the storage part 80 or the RFID tag of a sorting cup 141.

When any medicine included in the sorted medicine list image Im3 is selected and a user input on the "visual inspection" button Bo31 is received, the medicine sorting device 1 displays the inspection image Im2 of the medicine. Further, the list of medicines included in the sorted medicine list image Im3 may be scrolled up and down, and may be sorted by a user input. Further, by receiving a user input on a "container list" button Bo32 of the sorted medicine list image Im3, the medicine sorting device 1 switches the display from the sorted medicine list image Im3 to the sorting image Im1.

Further, the sorting image Im1 is a display image that shows the medicine sorting state (current sorting state) during the medicine sorting process performed by the medicine sorting device 1. Further, the sorted medicine list image Im3 is a display image that includes the past medicine sorting state by the medicine sorting device 1 in addition to the medicine sorting state during the medicine sorting process. That is, by displaying the sorted medicine list image Im3, the user may confirm information related to, for example, medicines which have been sorted in the past and on which visual inspection has not been completed.

Figure 28:
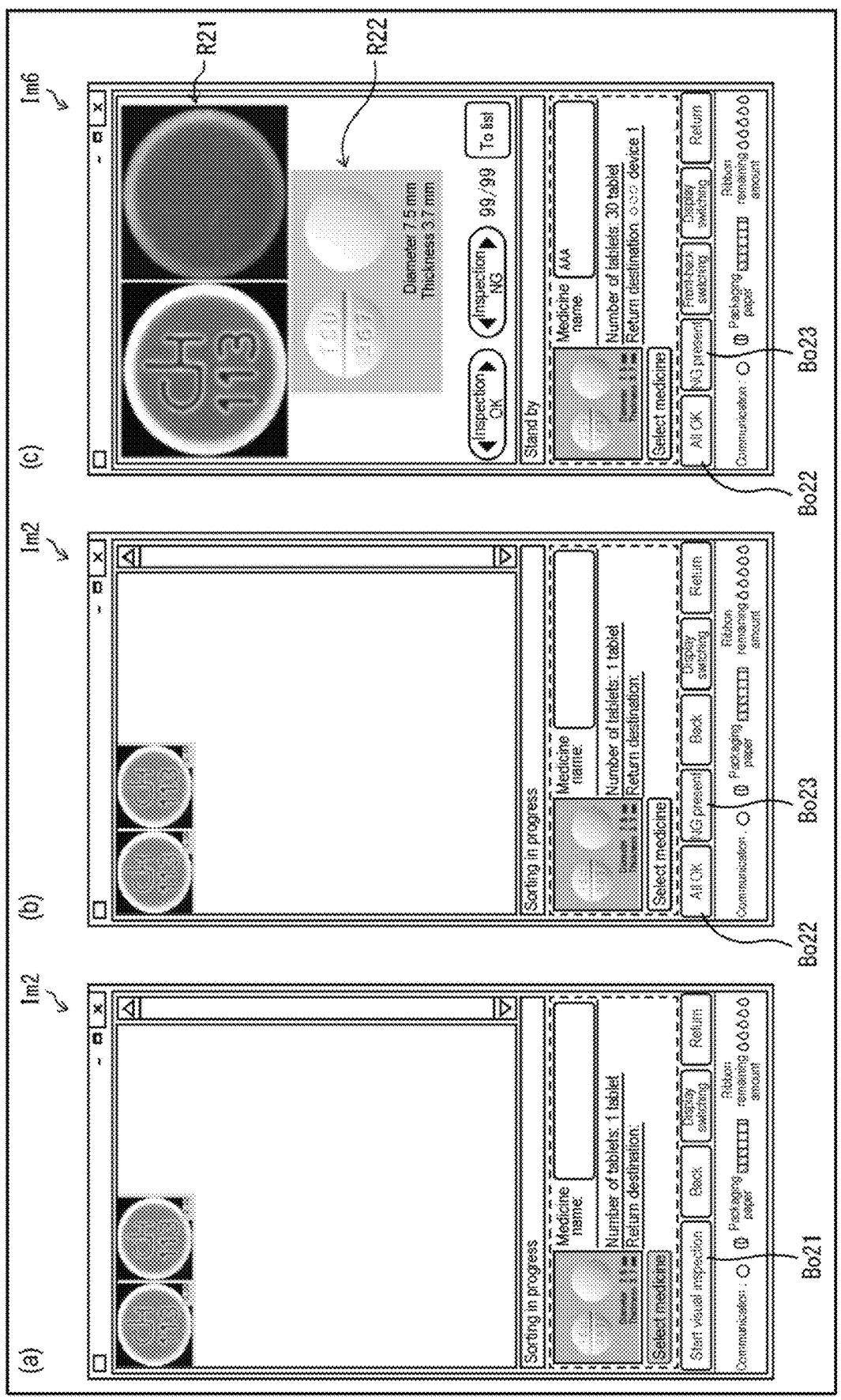
FIG. 28 ((a) to (c) of FIG. 28) is a view showing an example of an inspection image.

In FIG. 28, (a) to (c) of FIG. 28 are views showing an example of inspection images Im2. Further, the inspection images Im2 shown in (a) and (b) of FIG. 28 is another example of the display image shown in (b) of FIG. 11. Portions in the inspection image Im2 different from the display image shown in (b) of FIG. 11 are mainly described.

As shown in (a) of FIG. 28, when any medicine is selected in the sorting image Im1 or the sorted medicine list image Im3, the medicine sorting device 1 displays an inspection image Im2 of the medicine. When a user input on a "visual inspection start" button Bo21 in the inspection image Im2 is received, the medicine sorting device 1 displays the inspection image Im2 from which the result of visual inspection can be received as shown in (b) of FIG. 28.

The inspection image Im2 shown in (b) of FIG. 28 includes a "All OK" button Bo22 through which the visual inspection results for the displayed medicines (the medicines accommodated in a sorting cup 141) can be collectively registered, and an "NG present" button Bo23. The "All OK" button Bo22 and the "NG present" button Bo23 are manipulation buttons that are in place of a "register" button included in the display image shown in (b) of FIG. 11.

When a user input on the "All OK" button Bo22 is received, the medicine sorting device 1 assumes that the visual inspection result of all the displayed medicines is "Inspection OK", and writes the visual inspection result in the RFID tag of the sorting cup 141 in which the medicines are accommodated. Further, when a user input on the "NG present" button Bo22 is received, the medicine sorting device 1 assumes that the visual inspection result of at least one of all the displayed medicines is "Inspection NG", and writes the visual inspection result in the RFID tag of the sorting cup 141 in which the medicine are accommodated.

Further, in the inspection images Im2 shown in (a) and (b) of FIG. 28, when a user input is received on an image of a medicine stored in the sorting cup 141 (a visible light image of the medicine imaged by the imaging unit 13), the medicine sorting device 1 displays an enlarged display image Im6 of the medicine as shown in (c) of FIG. 28.

In an enlarged display area R21 of the enlarged display image Im6, an enlarged image of a selected medicine is displayed. Images of the front and back surfaces of the medicine imaged by the imaging unit 13 are displayed. Further, in a proper image display area R22, the image (a master image) (e.g., a bare tablet image) and the size of the selected medicine registered in the medicine database are displayed.

When the visual inspection result for the selected medicine is "Inspection OK", the medicine sorting device 1 receives "Inspection OK" as the visual inspection result of the medicine by receiving a user input on the "Inspection OK" button Bo22. Further, when the visual inspection result for the selected medicine is "Inspection NG", the medicine sorting device 1 receives "Inspection NG" as the visual inspection result of the medicine by receiving a user input on the "NG present" button Bo23.

Further, in the inspection image Im2 shown in (a) and (b) of FIG. 28, the image may be enlarged or reduced (e.g., pinch-in or pinch-out) by a user input on to the image of the imaged medicine. Therefore, in the inspection images Im2 shown in (a) and (b) of FIG. 28, a "display size" button for changing the display size of the display image shown in (b) of FIG. 11 becomes unnecessary.

Further, in the inspection image Im2, the medicine sorting device 1 may arrange images of a plurality of medicines accommodated in the sorting cup 141 in descending order of matching accuracy with the medicine images registered in the medicine database (e.g., from the upper left). Alternatively, the images may be arranged in ascending order of matching accuracy from the upper left). Therefore, it is possible to sequentially display medicines with low matching accuracy from the position at which an operator can most easily visually look at them, thereby improving the efficiency and accuracy of visual inspection. Further, in case where the user stores (returns) medicines, stored in the sorting cup 141, in a cassette (not shown) in the packaging device 200 in which the medicines are accommodated, or stores (returns) the medicines at a predetermined position in the medicine shelf 300, when the lid of the cassette or the door of the shelf has a locking mechanism, the locking mechanism for the cassette lid or shelf door may be made to be unlocked on the condition that the matching accuracy of all the medicines accommodated in the sorting cup 141 to be returned is not less than a predetermined value. The level or threshold value of the matching accuracy may be set based on a height of recognition reliability of information indicated by an engraving or print on a medicine recognized by the medicine sorting device 1 (engraving information or print information).

Figure 29:
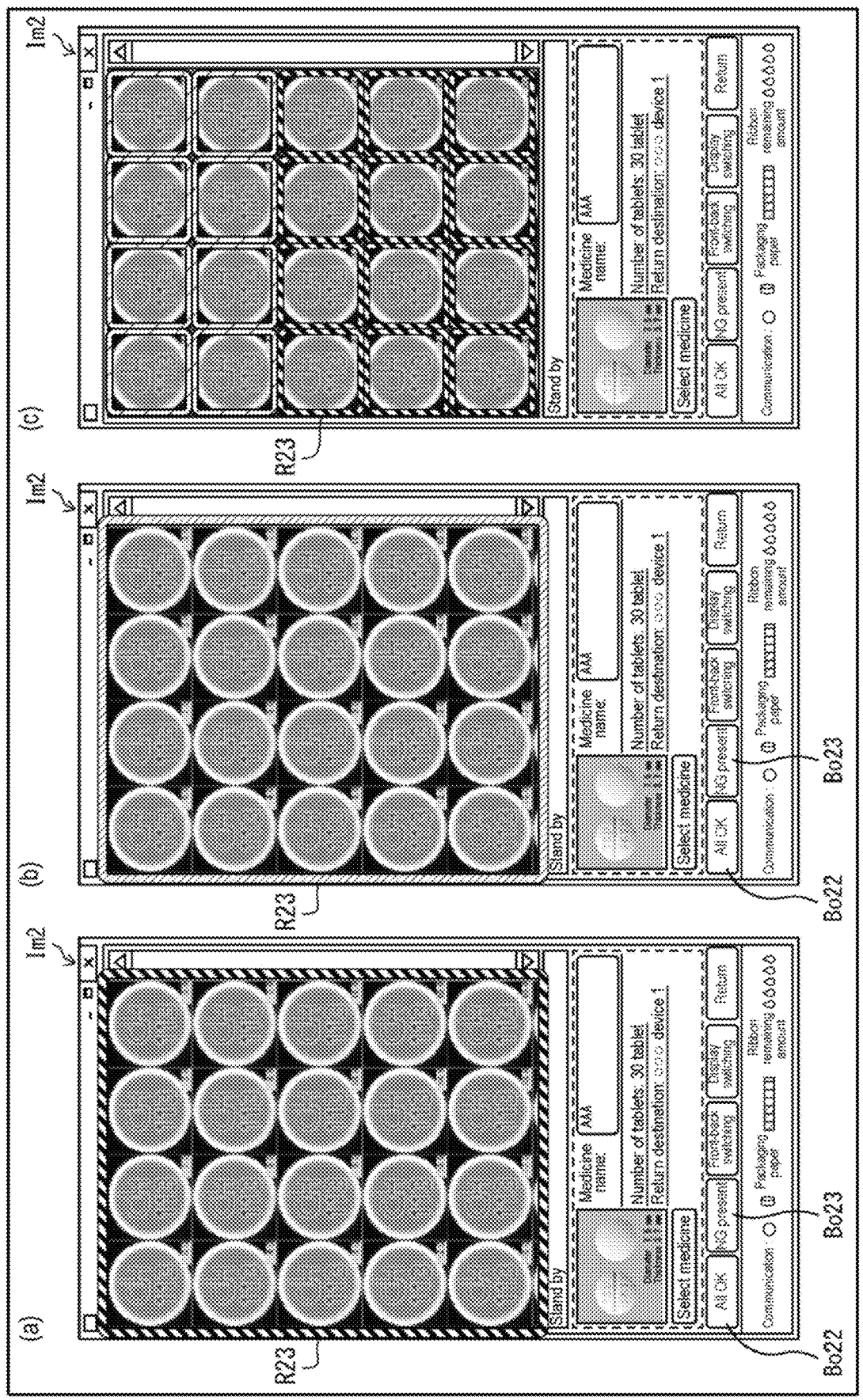
FIG. 29 ((a) to (c) of FIG. 29) is a view showing another example of an inspection image.

Next, in FIG. 29, (a) to (c) of FIG. 29 are views showing another example of the inspection image Im2. As shown in (a) to (c) of FIG. 29, the medicine sorting device 1 may display inspection images Im2 reflecting the presence/absence of execution of visual inspection and the visual inspection result.

For example, as shown in (a) and (b) of FIG. 29, the medicine sorting device 1 may perform the display method differently in case of receiving a user input on the "All OK" button Bo22 and in case of receiving a user input on the "NG present" button Bo23. For example, as shown in (a) of FIG. 29, when receiving a user input on the "All OK" button Bo22, the medicine sorting device 1 surrounds the entire display area R23 of medicines to be inspected with a predetermined pattern (e.g., green color). Further, as shown in (b) of FIG. 29, when receiving a user input on the "NG present" button Bo23, the medicine sorting device 1 surrounds the entire display area R23 with a pattern (e.g., yellow color) different from the predetermined pattern.

Further, as shown in (c) of FIG. 29, the medicine sorting device 1 may display an inspection image Im2 in which a pattern, from which the presence/absence of execution of visual inspection and a visual inspection result can be discriminated, is provided at each medicine image displayed in the display area R23. For example, for each medicine, a pattern is provided from which it is possible to discriminate three states such as the nonexecution of visual inspection, the visual inspection result of "Inspection OK", and the visual inspection result of "Inspection NG". In (c) of FIG. 29, the image of each medicine in the upper two rows of the display area R23 is provided with a pattern indicating the nonexecution of visual inspection (e.g., surrounded by a blue color), and the image of each medicine of the lower three rows of the display area R23 is provided with a pattern indicating "Inspection OK" (e.g., surrounded by a green color).

(Example of Display Image: Totalization Image)

Figure 30:
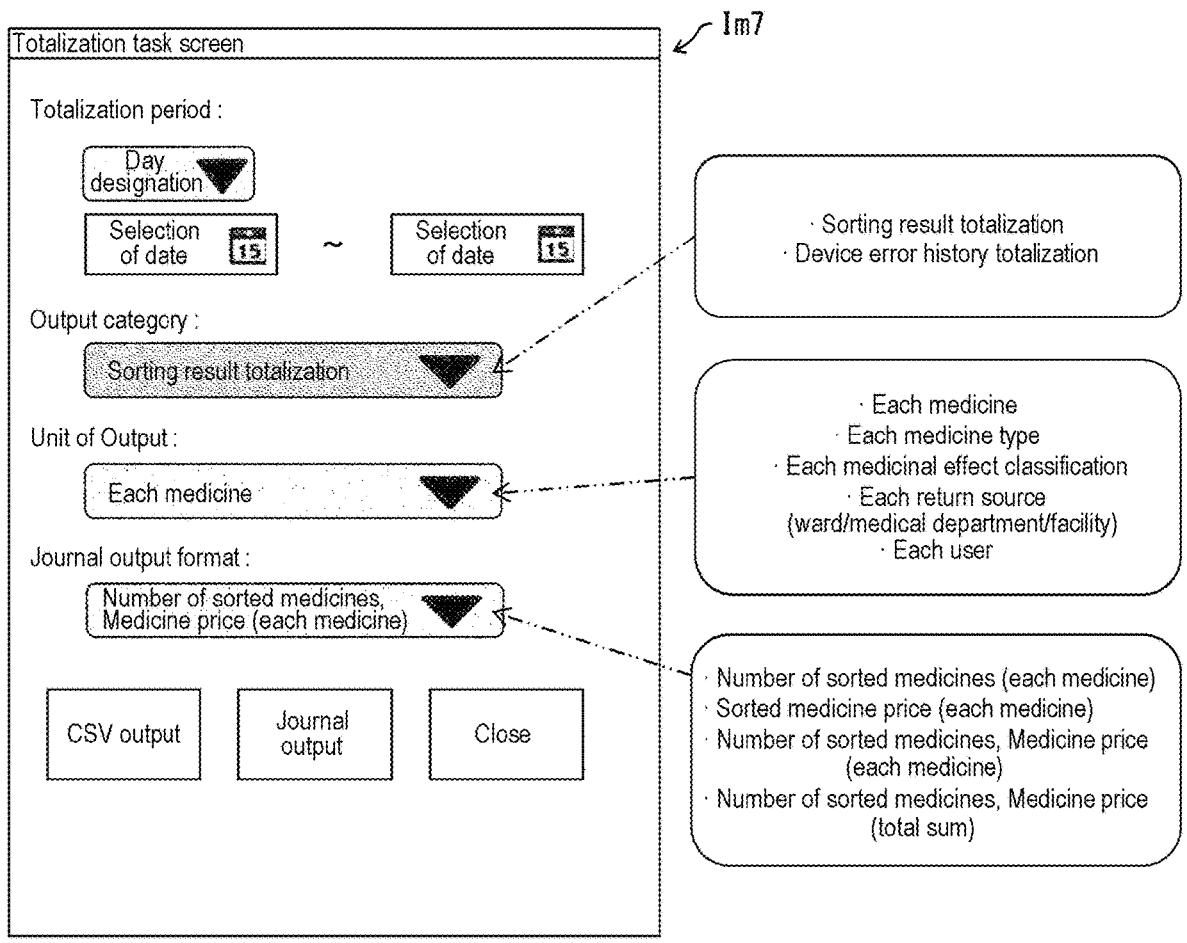
FIG. 30 is a view showing an example of a display image related to a totalization task of medicines sorted by a medicine sorting device.

Next, an example of a totalization image is described with reference to FIGS. 30 to 31. FIG. 30 is a view showing an example of a display image (totalization image Im7) related to a totalization task for medicines sorted by the medicine sorting device 1. The medicine sorting device 1 displays a totalization image Im7 as shown in FIG. 30 by receiving a user input for performing a medicine totalization task. The totalization image Im7 can receive user inputs for specifying, for example, "totalization period", "output category", "unit of output", and "journal output format". The medicine sorting device 1 displays a totalization result (e.g., outputting a comma separated value (CSV)) or outputs a journal in accordance with the user inputs.

In "totalization period", the totalization period desired by the user is set.

In "output category", a method of outputting a totalization result is set. As selection items for "output category", for example, "sorting result totalization" and "device error history totalization" are displayed in a pull-down manner. When "sorting result totalization" is selected, the medicine sorting device 1 performs totalization related to sorted medicines. When "device error history totalization" is selected, the medicine sorting device 1 totalizes error histories in the medicine sorting device 1. By storing logs when a malfunction such as an operation error of the conveyance/sorting unit 12, a communication error in the medicine sorting device 1, or a medicine adsorption error by the adsorption mechanism occurs, the medicine sorting device 1 totalize the logs as an error history.

In "unit of output", an output method at the time of performing totalization related to sorted medicines is set. As selection items for "unit of output", for example, "each medicine", "each medicine type", "each medicinal effect category", "each return source (ward/medical department/facility)" and "each user" are displayed in a pull-down manner. The medicine sorting device 1 performs totalization related to the sorted medicines for each medicine, for each medicine type, for each medicinal effect, for each return source, or for each user in accordance with the selected item.

In "journal output format", an output method at the time of printing and outputting the totalization result of sorted medicines in the journal is selected. As the selection items for "journal output format", for example, "number of sorted medicines (each medicine)", "medicine price of sorted medicines (each medicine)", "number and medicine price of sorted medicines (each medicine)" and "number and medicine price of sorted medicines (total sum)" are displayed in a pull-down manner. In accordance with the selected item, the medicine sorting device 1 performs totalization with respect to the number of sorted medicines for each sorted medicine, the medicine price of sorted medicines for each sorted medicine (sum, i.e., the number of medicines×the unit price of a medicine), the number and medicine price of sorted medicines for each sorted medicine (sum), or the number of all sorted medicines and the total sum of medicine prices.

In FIG. 31, (a) to (d) of FIG. 31 are views showing an output example when a totalization result is output by a journal.

An example where the number of medicines is printed in a journal for each sorted medicine is shown in (a) of FIG. 31. In this example, "journal output format" and "number of sorted medicines (each medicine)" are selected in the totalization image Im7. An example where the medicine price of medicines is printed in a journal for each sorted medicine is shown in (b) of FIG. 31. In this example, "journal output format" and "medicine price of sorted medicines (each medicine)" are selected in the totalization image Im7. An example where both the number and medicine price of medicines are printed in a journal for each sorted medicine is shown in (c) of FIG. 31. In this example, "journal output format" and "number and medicine price of sorted medicines (each medicine)" are selected in the totalization image Im7. An example where both the total number and medicine price of all the sorted medicines are printed in a journal is shown in (d) of FIG. 31. In this example, "journal output format" and "number and medicine price of sorted medicines (total sum)" are selected in the totalization image Im7.

Further, in the journal output examples of (a) to (c) of FIG. 31, the number of all the sorted medicines and the total sum of medicine prices of all the sorted medicines are printed together, but this printing is optional.

By receiving a user input on the totalization image Im7 during the totalization task, the medicine sorting device 1 can perform the totalization of the sorted medicines, for example, "for each time of sorting process (for each ward, each medical department or each facility)" and "for each designated period". Further, the medicine sorting device 1 can totalize the number of medicines (the number of sorted tablets) or the medicine price (total sum) "for each medicine", "for each medicinal effect", or "for each medicine type". Further, the medicine sorting device 1 can output the totalization result by displaying or printing it on a journal. Further, regarding the medicine price, the unit price of each medicine may be output. Further, regarding medicines that cannot be sorted, the medicine sorting device 1 may totalize and output, for example, the number of such medicines (total number of tablets).

<Configuration Example of Sorting Cup>

Figure 32:
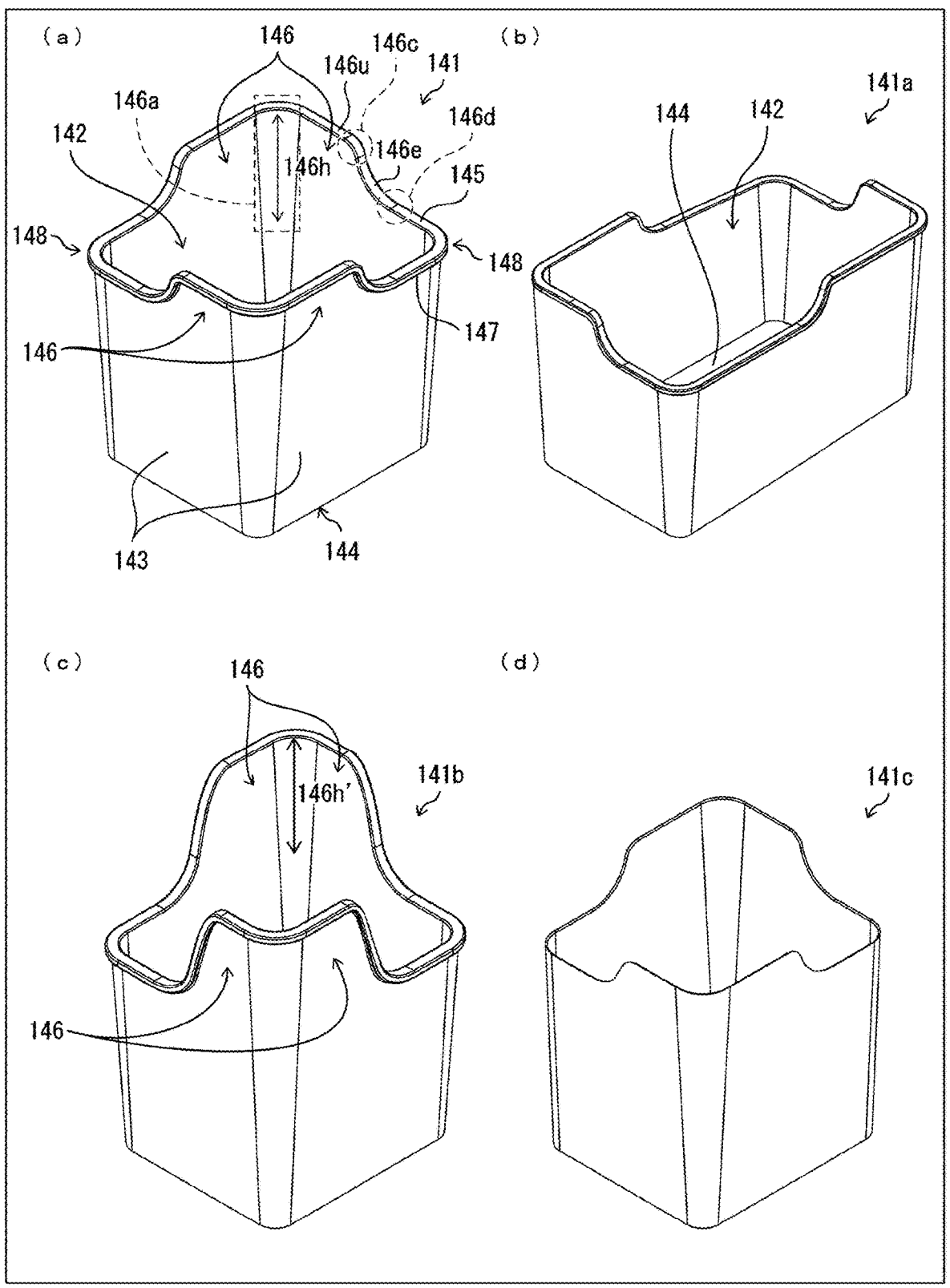
FIG. 32 ((a) of FIG. 32) is a view showing an example of a specific configuration of a sorting cup, and FIG. 32 ((b) to (d) of FIG. 32) is a view views showing a variation example of a sorting cup.
Figure 33:
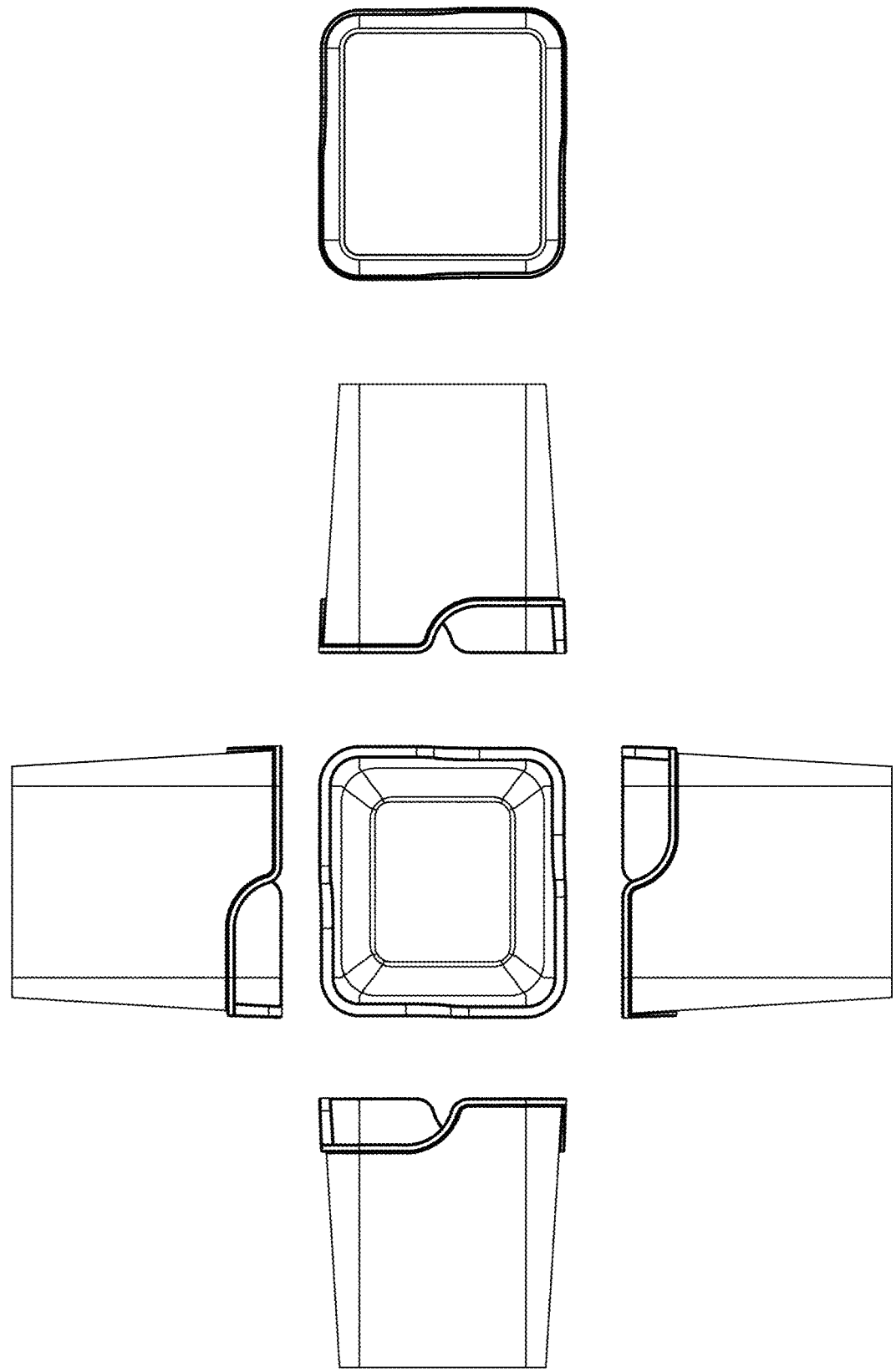
FIG. 33 is a set of six views of the sorting cup shown in (a) of FIG. 32.

A specific configuration example of a sorting cup 141 is described below. In FIG. 32, (a) of FIG. 32 is a view showing an example of a specific configuration of the sorting cup 141. FIG. 33 is a set of six views of the sorting cup 141 shown in (a) of FIG. 32.

As described above, the sorting cup 141 is a sorting container that accommodates the medicines sorted by the medicine sorting device 1 (specifically, the conveyance/sorting unit 12) by being disposed in the second accommodating part 14.

As shown in (a) of FIG. 32 and FIG. 33, the sorting cup 141 has a substantially rectangular parallelepiped shape and includes side walls 143 (outer walls) and a bottom portion 144. That is, when viewed from an opening 142 side, the shape of the sorting cup 141 (the shape of the opening 142 and the bottom portion 144) is substantially rectangular. In this case, when compared with a case where a sorting cup 141 has a substantially cylindrical shape, it is possible to disposed the sorting cups 141 in the second accommodating part 14 without a gap. Therefore, it is possible to effectively use an accommodation space for the sorting cups 141 in the second accommodating part 14. Further, in this embodiment, the "rectangular shape" in the shape of the sorting cup 141 includes a case where four corners are formed in a curved shape.

In particular, in case where the shape of the sorting cup 141 viewed from the opening 142 side is substantially rectangular, it is possible to define the directionality of the sorting cup 141 when the sorting cup 141 is disposed in the second accommodating part 14. That is, it is possible to align and dispose the plurality of sorting cups 141 such that long sides (or short sides) of the plurality of sorting cups 141 are oriented in the same direction. Further, by forming placement places for the sorting cups 141 in the second accommodating part 14 so as to fit with the shape of the sorting cups 141, it is possible to uniformly dispose the plurality of sorting cups 141 in a predetermined direction without a gap therebetween.

In the sorting cup 141, the opening 142 into which the medicine sorted by the conveyance/sorting unit 12 is inserted is formed at a top side of the sorting cup 141 by the side walls 143. Further, top portions of the side walls 143 define edge portions 145 as an outer periphery of the opening 142.

Further, the size of the opening 142 may be larger than the size of the bottom portion 144 so that the medicines conveyed by the conveyance/sorting unit 12 can be easily accommodated in the sorting cup 141 and the medicines accommodated in the sorting cup 141 can be easily taken out. That is, a sectional shape of the sorting cup 141, which is taken by cutting the sorting cup along a plane including a perpendicular line of the bottom portion 144 (a sectional shape of the sorting cup 141 viewed from the side wall 143 side), may be a substantially trapezoidal shape where the bottom portion 144 side is smaller than the opening 142 side. The shape of the sorting cup is not limited thereto. The sorting cup 141 may have a rectangular parallelepiped shape in which the size of the bottom portion 144 and the size of the opening 142 are substantially the same.

The sorting cup 141 is provided with a convex portion 146 in at least a portion of the edge portion 145. Specifically, the convex portion 146 is provided in at least one of a plurality of sides constituting the edge portion 145. That is, the edge portion 145 includes the convex portion 146 and a base portion 148 that is a portion other than the convex portion 146.

The user can lift up the sorting cup 141 disposed in the second accommodating part 14 by holding the convex portion 146. That is, by providing the edge portion 145 with the convex portion 146, each of the plurality of sorting cups 141 accommodated in the second accommodating part 14 can be easily taken out from the second accommodating part 14.

In (a) of FIG. 32, one convex portion 146 is provided in each of the four sides of the edge portion 145. Further, the convex portions 146 provided in the two adjacent sides located adjacent to each other. And, heights 146h of adjacent portions 146a adjacent to each other are the same. Therefore, since it is possible to widen the convex portions 146, the ease of handling the sorting cup 141 is improved.

Further, in (a) of FIG. 32, the convex portions 146 are provided at the corners opposed to each other. In addition, as described above, the opening 142 and the bottom portion 144 are substantially rectangular. Therefore, the user can easily dispose the sorting cups 141 in the second accommodating part 14 by aligning the directions of the sorting cups, and as a result, the user can easily dispose the sorting cups 141 such that the convex portions 146 provided at the corners are not adjacent to each other. That is, the user can dispose the sorting cups 141 so as to easily take out the sorting cups 141 without being conscious of it.

In case the opening 142 and the bottom portion 144 are square, the convex portions 146 may be adjacent to each other in the adjacent sorting cups 141 if the user does not consciously dispose the sorting cups 141. In this case, since it is difficult for the user to hold the convex portions 146, it is difficult to take out the sorting cup 141. However, for example, when the placement places for the sorting cups 141 are defined in the second accommodating part 14 so that the sorting cups 141 can be easily taken out, the shape of the sorting cup 141 viewed from the opening 142 side may be square.

Further, as long as the sorting cups 141 can be disposed such that the user can unconsciously take out the sorting cups 141, the convex portions 146 may not be provided at the corners as described above. For example, the convex portions 146 may be provided in respective sides so as to be point-symmetric to each other on the sides opposed to each other.

Further, the shape of the sorting cup 141 may be any shape if the above-described points are not taken into consideration. For example, the shape of the opening 142 or the bottom portion 144 may be circular or elliptical, and a portion of the outer periphery of the opening 142 or the bottom portion 144 may be curved. Further, the convex portions 146 may not be provided in all the sides, and may not be provided so as to adjoin each other at the corner portions and to be opposed to each other. Further, the heights of the adjacent portions 146a in the adjacent convex portions 146 may differ from each other.

The edge portion 145 functions as a protruding portion (a return portion) that protrudes outward from the side walls 143 at a connection portion between the edge portion and the side walls 143 (top portion of the side walls 143). This enables the user to hook a finger on the protruding portion, and thus the ease of being taken out is further improved.

However, unless this point is taken into consideration, it is not necessary that the edge portion 145 protrudes outward from the side walls 143.

Further, in (a) of FIG. 32, top portions 146u of the convex portions 146 are not inclined, and are linear. Extension portions 146e of the convex portions 146, which extend up to the base portion 148, are inclined from the top portions 146u toward the base portions 148. The base portions 148 are not inclined, and are linear. Connection portions 146c between the top portions 146u and the extension portions 146e of the convex portions 146 and connection portions 146d between the extension portions 146e of the convex portions 146 and the base portions 148 are all substantially arc-shaped.

The sorting cup 141 in this example has a hue (for example, black color) so that the medicines can be easily specified in the imaging using the second camera 121. However, as long as the medicine can be imaged, the sorting cup 141 may have light transmission property.

(Variation Example of Sorting Cup 141)

Variation examples of the sorting cup 141 are shown in (b) to (d) of FIG. 32. In the sorting cup 141a shown in (b) of FIG. 32, the opening 142 and the bottom portion 144 have a rectangular shape that is horizontally longer (or vertically longer) than the opening 142 and the bottom portion 144 of the sorting cup 141 shown in (a) of FIG. 32. In the sorting cup 141b shown in (c) of FIG. 32, the height 146h' of the convex portions 146 is higher than the height 146h of the convex portion 146 of the sorting cup 141 shown in (a) of FIG. 32. The sorting cup 141c shown in (d) of FIG. 32 is not provided with the protruding portion (return portion) in the edge portion 145 in the sorting cup 141.

Figure 34:
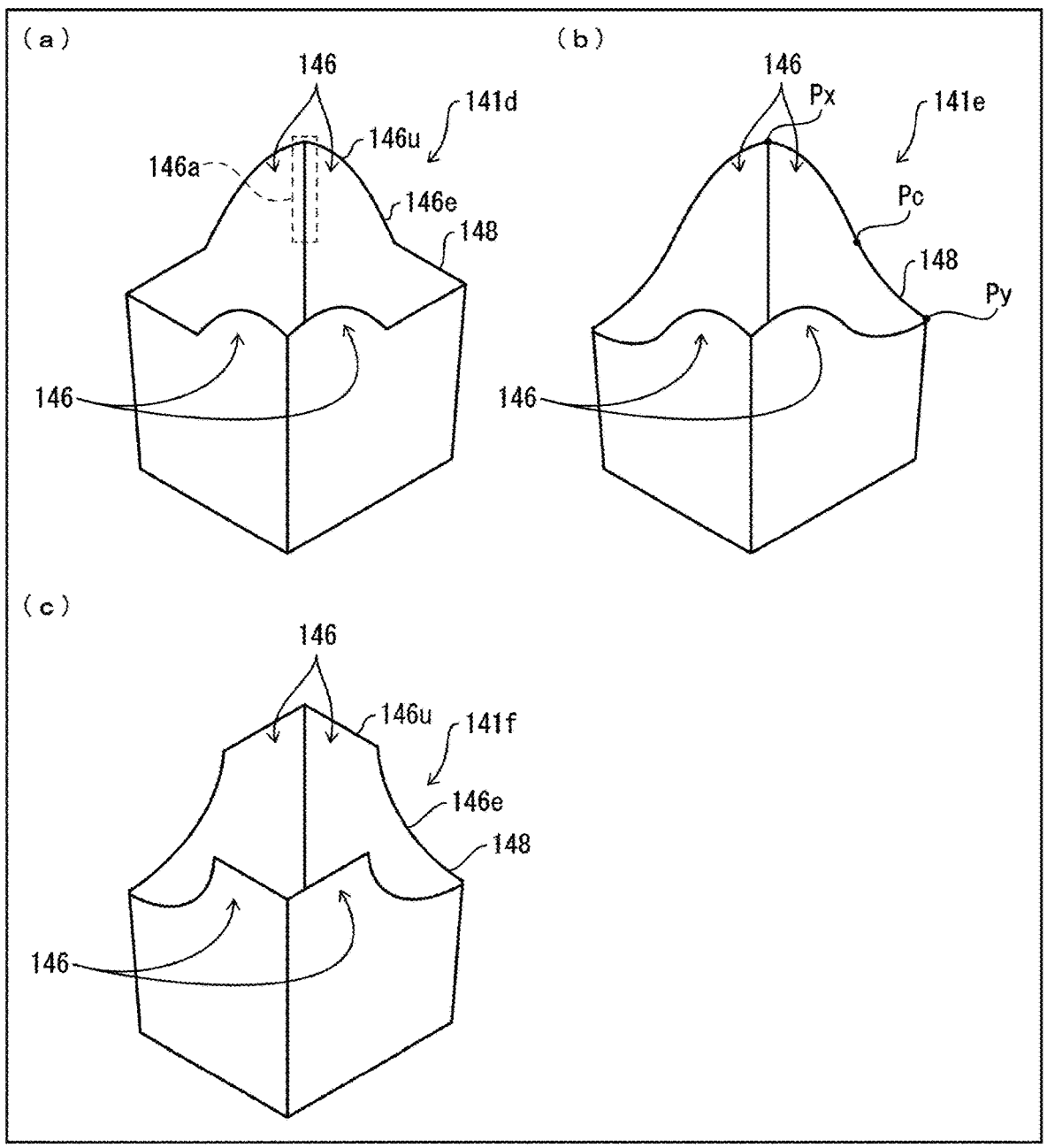
FIG. 34 ((a) to (c) of FIG. 34) is a view showing a further variation example of a sorting cup.
Figure 35:
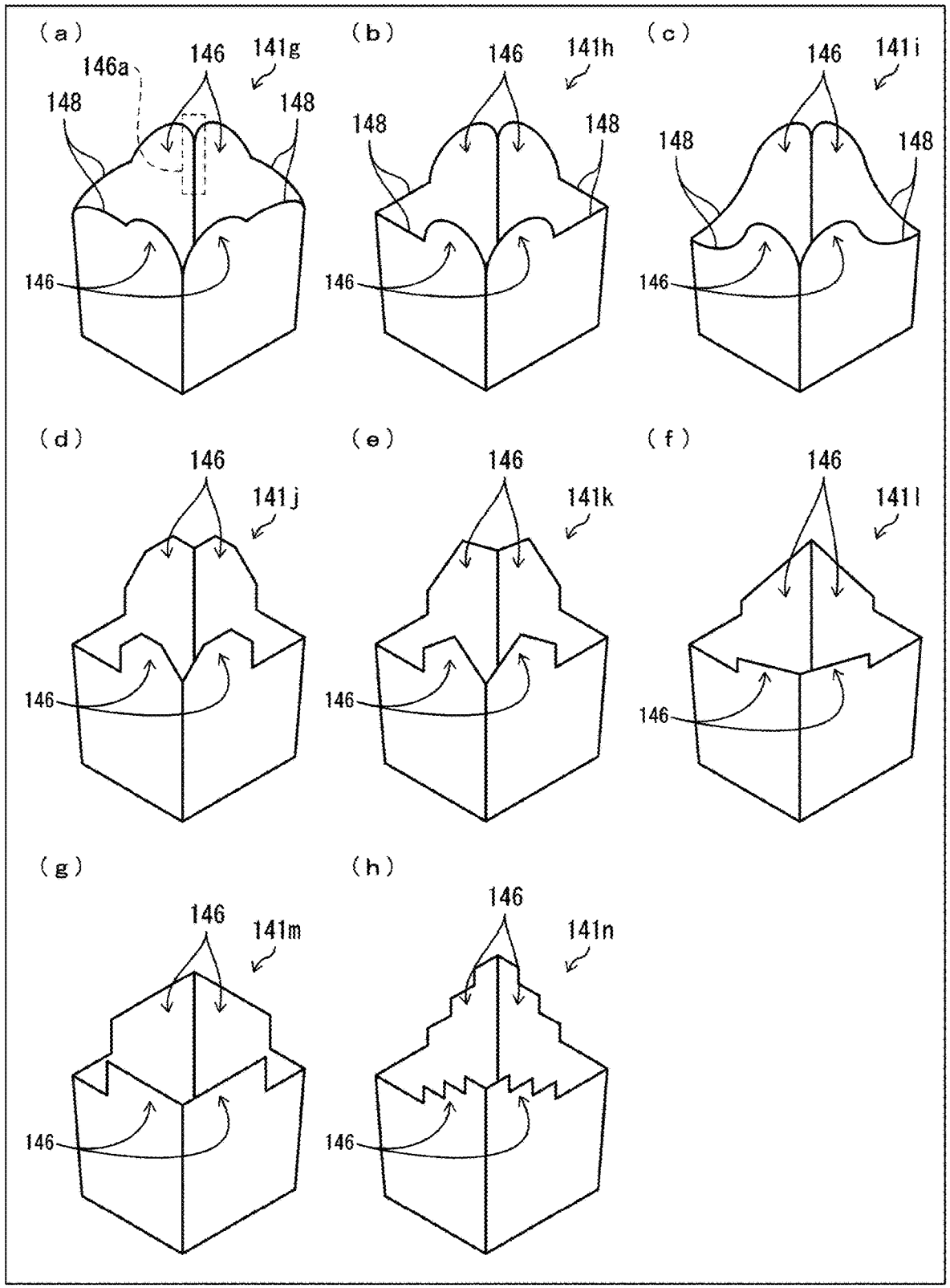
FIG. 35 ((a) to (h) of FIG. 35) is a view showing another variation example of a sorting cup.

Further variation examples of the sorting cup 141 are shown in (a) to (c) of FIG. 34 and (a) to (h) of FIG. 35. It is shown in (a) to (c) of FIG. 34 and (a) to (h) of FIG. 35 that no protruding portion is provided in the edge portion 145. However, like the sorting cup 141, the protruding portion may be provided in the edge portion 145.

In the sorting cup 141d shown in (a) of FIG. 34, the convex portions 146 (that is, the top portions 146u and the extension portions 146e) are substantially arc-shaped. That is, end portions of the top portions 146u, which are located opposite to end portions connecting with the extension portions 146e (the adjacent portions 146a where the convex portions 146 are adjacent to each other in (a) of FIG. 34), protrude most upward. In the sorting cup 141e shown in (b) of FIG. 34, in addition to the convex portions 146 and the extension portions 146e, the base portions 148 are also substantially arc-shaped. In the sorting cup 141d, at least the base portions 148 have a concave shape. That is, in the sorting cup 141d, a curve connecting a point Px and a point Py is point symmetric with respect to an approximate center Pc thereof. In the sorting cup 141f shown in (c) of FIG. 34, the top portions 146u are linear, and the extension portions 146e and the base portions 148 are substantially arc-shaped. At least the base portions 148 have a concave shape.

In the sorting cup 141g shown in (a) of FIG. 35, the vicinity of the center of each convex portion 146 has a curved shape protruding upward. That is, the sorting cup 141g is different from the sorting cup 141d shown in (a) of FIG. 34 since the portions protruding most upward of the convex portions 146 are not the adjacent portions 146a, but the vicinities of the centers thereof. Further, the base portions 148 also have a curved shape in which the vicinity of the center thereof protrudes upward. In the sorting cup 141h shown in (b) of FIG. 35, the convex portions 146 have a curved shape, which is the same as that in (a) of FIG. 35, but the base portions 148 are linear. In the sorting cup 141i shown in (c) of FIG. 35, the convex portions 146 have a curved shape, which is the same as that in (a) of FIG. 35, but the base portions 148 have a concave shape like the sorting cup 141e shown in (b) of FIG. 34.

In the sorting cups 141g to 141i shown in (a) to (c) of FIG. 35, the convex portions 146 have a curved shape, but may have a polygonal shape like the sorting cups 141j to 141m shown in (d) to (g) of FIG. 35. Further, as shown in (h) of FIG. 35, the convex portions 146 may have a stepped shape.

(Others: Bottom Portion Shape of Sorting Cup)

Fine projections may be provided on the inner bottom portion surface of the sorting cup 141. If the adsorption mechanism approaches the inner bottom portion surface of the sorting cup 141 and sucks the sorting cup 141, then the sorting cup 141 may be lifted. Providing the fine projections on the inner bottom portion surface can make it difficult to adsorb the sorting cup 141.

Further, to prevent the first accommodating part 11 from being lifted, fine projections may be provided on the inner bottom portion surface of the first accommodating part 11.

<Other Various Process Examples or Operation Examples>

(Character Recognition)

Next, a further example of a character recognition process by the discrimination part 64 is described. Here, it is assumed that the storage part 80 stores, as medicine master information, for example, image data (master image) indicating a medicine image including a character, an engraving, a dividing line line, and the like in association with identification information indicating a medicine name. This image data may be managed by a medicine database. Further, in this case, the discrimination part 64 performs pattern-matching of the medicine image captured by the first camera 131 in the placement area Ar with a plurality of pieces of image data stored in the storage part 80.

Generally, when performing an OCR process, the orientations and sizes of characters included in target images need to be constant. Therefore, the discrimination part 64 performs the OCR process while rotating a visible light image. However, in this case, since it is necessary to rotate the visible light image for each analysis, the processing time is required accordingly. Moreover, there is a possibility that the character recognition accuracy of the OCR process is not necessarily high.

Thus, in this example, symbol specifying information for specifying symbols indicated on medicines are registered in advance in association with identification information, wherein the symbol specifying information indicates types (e.g., characters (numeral characters and alphabet letters), maker marks, and dividing lines), sizes, and angles of the symbols indicated on medicines. The discrimination part 64 specifies the types of medicines by referring to the symbol specifying information.

Figure 36:
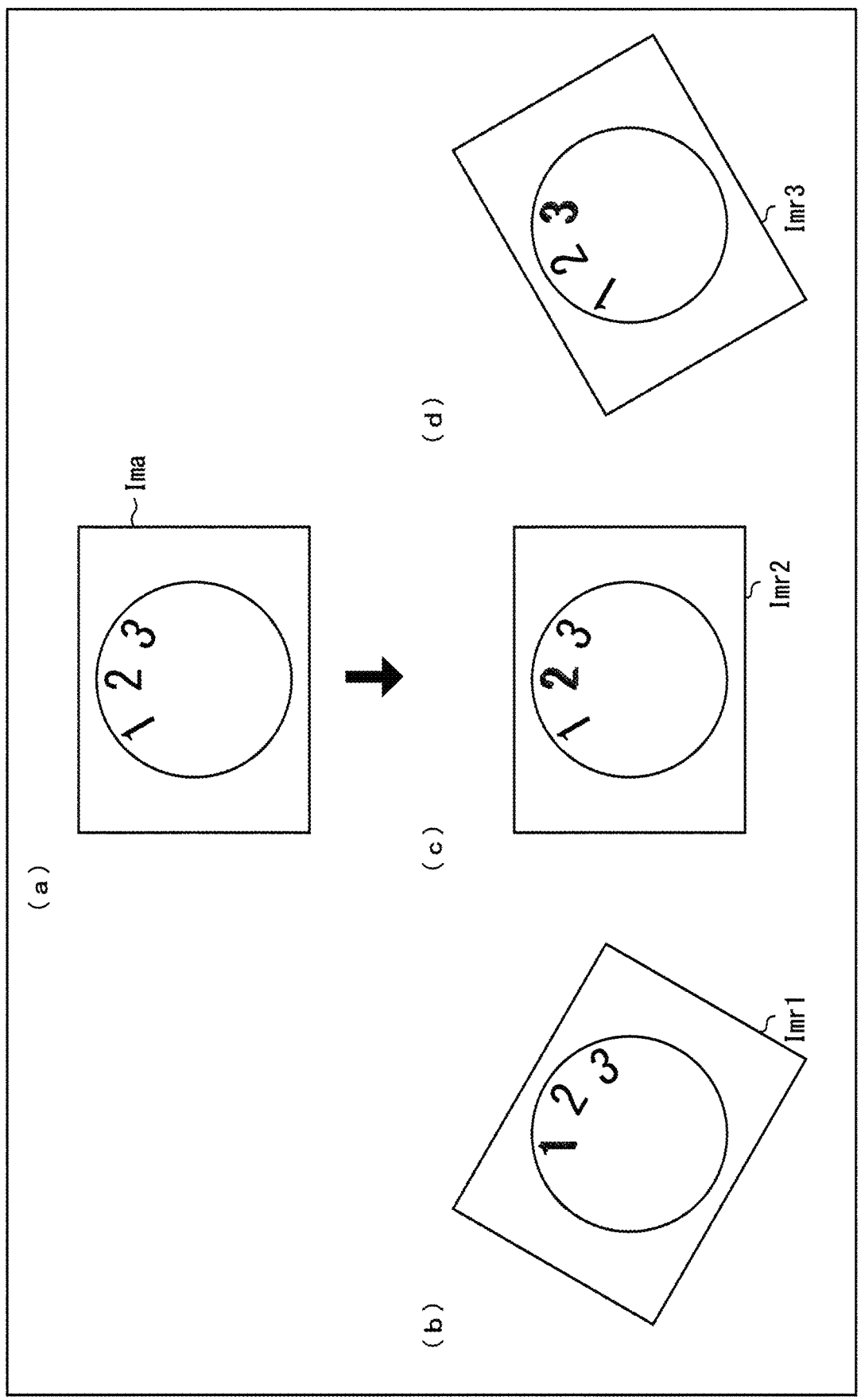
FIG. 36 is a view illustrating an example of a method of creating symbol specifying information, wherein (a) of FIG. 36 shows an example of an image of a medicine for which symbol registration information is to be created, and (b) to (d) of FIG. 36 are views showing examples of images of a medicine when acquiring symbol specifying information.

A method of creating the symbol specifying information is described with reference to FIG. 36. FIG. 36 is a view illustrating an example of a method of creating the symbol specifying information. In FIG. 36, (a) of FIG. 36 is a view showing an example of a medicine image Ima for which symbol registration information is to be created, and (b) to (d) of FIG. 36 are views showing examples of medicine images Imr1 to Imr3 at the time of acquiring the symbol specifying information. Further, a symbol specifying information creating process is executed by an information creating device that creates symbol specifying information. The information creation device may be provided in the medicine sorting device 1, and the symbol registration information may be created by the medicine sorting device 1. Further, it is assumed that the information creation device has the above-described master information.

First, as shown in (a) of FIG. 36, the information creation device acquires an image Ima of a medicine for which symbol registration information is to be created. In this example, the image Ima includes characters (numeral characters) of 1, 2, and 3.

Next, as shown in (b) to (d) of FIG. 36, the information creation device acquires symbol specifying information by performing pattern-matching of the image Ima with the image data included in the master information of the medicine while rotating the image Ima. For example, in the state of (b) of FIG. 36, "1" is acquired from the image Imr1 by performing the pattern matching. At this time, the information creation device specifies a plurality of pixels forming "1" by drawing a line so as to trace "1" in the image Imr1. Therefore, the information creation device specifies the size of "1" in the image Imr1. Further, at this time, the character type may be specified as a numeral character. Further, when a position of the image Ima shown in (a) of FIG. 36 is used as a reference, the information creation device also acquires the angle of the image Imr1 from the reference. Therefore, the information creation device specifies the angle of "1" in the image Imr1. In the states (c) and (d) of FIG. 36 as well, the size and angle of "2" in the image Imr2 and the size and angle of "3" in the image Imr3 are specified.

The information creation device stores the type, size, and angle of the specified character as identification information in the storage part 80 of the medicine sorting device 1 in association with identification information (master information).

The discrimination part 64 performs pattern matching of the captured medicine image with a plurality of pieces of image data stored in the storage part 80, thereby narrowing down a plurality of types (e.g., ten types) of medicines in descending order of matching score. The discrimination part 64 collates the captured image with the symbol specifying information with respect to each of the narrowed-down medicines (applies the symbol specifying information to the captured image). The discrimination part 64 specifies a medicine image having the highest degree of coincidence with the symbol specifying information among the captured images of the narrowed-down medicine, and specifies that the medicine corresponds to the type of a medicine (medicine name) associated with the symbol specifying information.

By performing the collation by using the symbol specifying information as described above, the discrimination part 64 can specify the type of a medicine more easily and accurately that the OCR process. Therefore, the discrimination part 64 can specify the type of a medicine rapidly and highly accurately.

(Medicine Adsorption Method)

Figure 37:
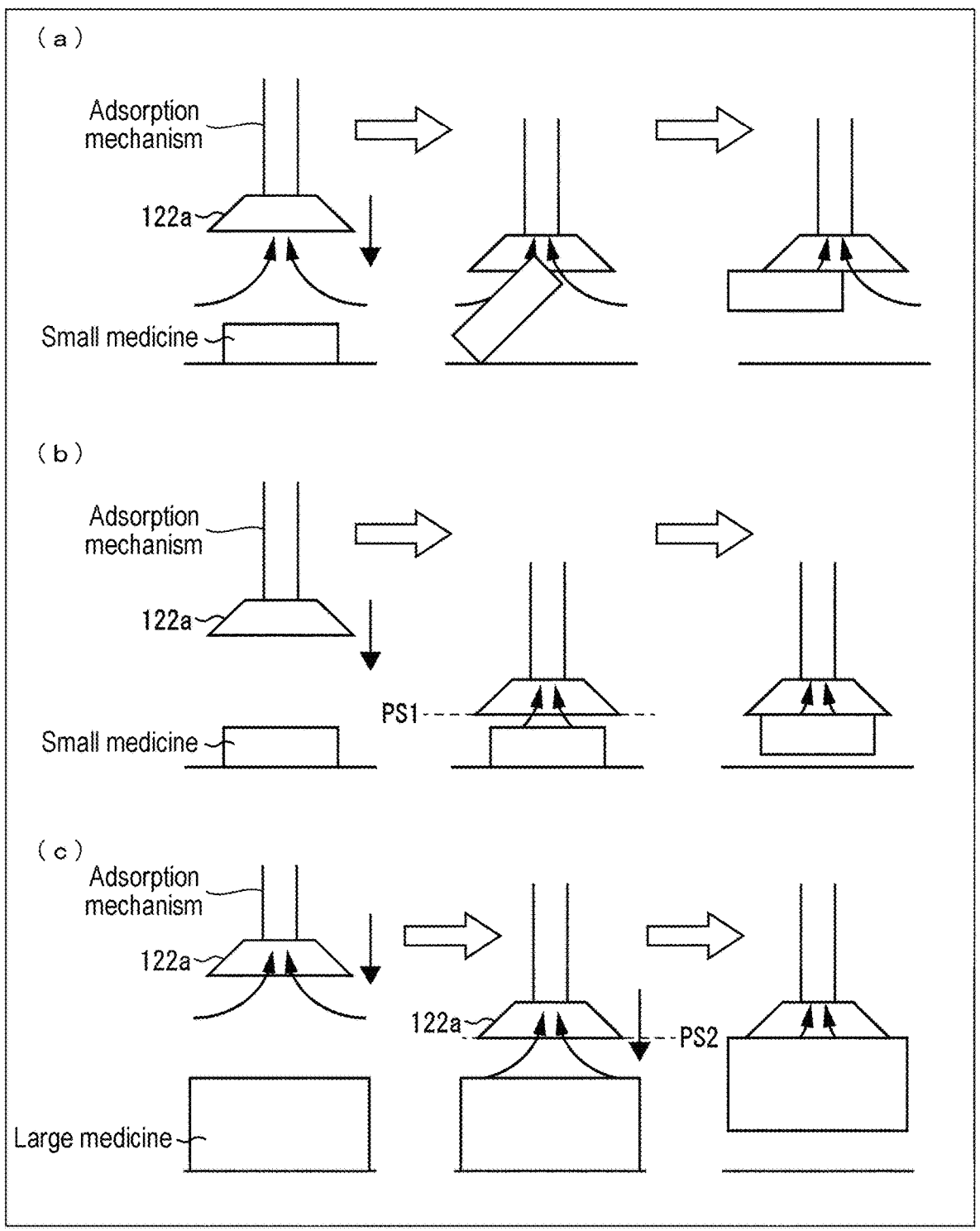
FIG. 37 is a view illustrating an example of a medicine adsorption method, wherein (a) of FIG. 37 is a view illustrating the state where a relatively small medicine is adsorbed while moving an adsorption mechanism, and (b) to (c) of FIG. 37 are views illustrating the state where a medicine is adsorbed when an adsorption method is changed due to the size of a medicine.

Next, a medicine adsorption method is described with reference to FIG. 37. FIG. 37 is a view illustrating an example of a medicine adsorption method In FIG. 37, (a) of FIG. 37 is a view illustrating the state where a relatively small medicine is adsorbed while the adsorption mechanism is being moved, and (b) and (c) of FIG. 37 are views illustrating the states where medicine are adsorbed when the adsorption method is changed due to the sizes of medicines.

As described above, the adsorption mechanism changes the moving speed in the Z-axis direction during medicine adsorption (moving speed when descending) based on, for example, a change in suction force detected by a pressure sensor. For example, when the adsorption mechanism adsorbs a medicine in the first accommodating part 11, the adsorption mechanism stops immediately before the medicine (before contact with the medicine) so as not to push the medicine because of the descending. In this case, since the adsorption mechanism adsorbs the medicine immediately before the medicine, the adsorption mechanism descends in the state where air is sucked by the vacuum pump 122d.

Here, a relatively small medicine has a relatively light mass. Therefore, as shown in (a) of FIG. 37, when a relatively small medicine is to be adsorbed by the above-described method, the medicine may be sucked up obliquely immediately before the adsorption mechanism. In this case, since a gap is formed between the adsorption pad 122a and a medicine, or the suction force (flow rate) varies depending upon the position of the adsorption pad 122a, the suction force becomes unstable. Therefore, it may be difficult to specify whether or not the medicine is adsorbed to the adsorption pad 122a from the change in the suction force.

Further, when adsorbing a medicine, the second camera 121 images the medicine placed on the medicine placement table 133a. Therefore, the sorting control part 62 can calculate the size (area) of a medicine to be adsorbed by analyzing the captured image. In particular, since one medicine is placed on the medicine placement table 133a at least during the adsorption of the medicine, the sorting control part 62 can relatively easily calculate the size of the medicine to be adsorbed. The size of the medicine is specified by, for example, counting the number of pixels of the medicine image in the acquired image.

In this example, the sorting control part 62 changes the medicine adsorption method by determining whether or not the calculated size of the medicine is equal to or greater than a predetermined value. This predetermined value is set in advance through, for example, experiments or the like.

Specifically, when the calculated area of the medicine is less than the predetermined value (when the medicine is relatively small), the sorting control part 62 lowers the adsorption mechanism to a predetermined position PS1 without suction, as shown in (b) of FIG. 37. Thereafter, the sorting control part 62 starts suction at the predetermined position PS1 and adsorbs the medicine. The predetermined position PS1 is a position where the medicine can be adsorbed by suction, and substantially coincides with, for example, a place where the suction force changes in the above-described method changes. If the medicine is adsorbed in this manner, then it is possible to lift the medicine upward. Thus, it is possible to stabilize the suction force in the state where the medicine is adsorbed, unlike the case of (a) of FIG. 37. Therefore, it is possible for the sorting control part 62 to stably perform adsorption determination of a relatively small medicine.

Further, the predetermined position PS1 may be uniformly set at the same position (height), or may be calculated from, for example, the distance to the medicine detected by the distance measurement sensor. Further, when the type of a medicine is specified, the predetermined position PS1 may be calculated based on information related to the sizes of medicines included in the medicine database (e.g., diameter, thickness).

Further, when the calculated area of a medicine is equal to or larger than a predetermined value (when the medicine is relatively large), the sorting control part 62 adsorbs the medicine by the above-described method, as shown in (c) of FIG. 37. That is, the sorting control part 62 lowers the adsorption mechanism with suction, and stops the adsorption mechanism at the timing of the change in the suction force (i.e., at a predetermined position PS2). That is, the adsorption mechanism stops immediately before the medicine. In this state, the adsorption mechanism adsorbs the medicine. When the medicine is relatively large, even with this method, the possibility of lifting the medicine obliquely is low. Thus, it is possible to stabilize the suction force in the state where the medicine is adsorbed. Further, since the adsorption mechanism is stopped at the predetermined position PS2 based on the change in the suction force, it is possible to stop the adsorption mechanism in a simple and reliable manner immediately before the medicine (without crushing the medicine).

As described above, by changing the adsorption method depending upon the size of a medicine (i.e., the weight of a medicine), it is possible for the medicine to be stably adsorbed to the adsorption pad 122a regardless of the weight of the medicine. Therefore, since the failure of medicine adsorption can be reduced, it is possible to speed up the medicine sorting process.

Further, even when a relatively large medicine is adsorbed, the suction may be started at the predetermined position PS2 after the adsorption mechanism is moved to the predetermined position PS2 without suction, as described above with reference to (b) of FIG. 37. In this case, the medicine size determination process is unnecessary.

Further, the method described with reference to (b) and (c) of FIG. 37 may also be adopted for adsorbing medicines in the first accommodating part 11 and the sorting cup 141. In this case, the conveyance control part 61 specifies a medicine to be adsorbed from the captured image, and thereafter calculates the size of the medicine. Further, the predetermined position PS1 is calculated, for example, by detecting the distance to the medicine to be adsorbed by the distance measurement sensor.

(Air Blowing Operation)

Next, an air blowing operation by the adsorption mechanism is described.

Depending upon a position at which a medicine to be adsorbed by the adsorption mechanism is placed or depending upon a posture of the medicine, there is a possibility that the adsorption mechanism cannot adsorb the medicine. For example, when the medicine is placed at an end portion of the first accommodating part 11, the sorting cup 141, or the medicine placement table 133a, or stands obliquely, there is a possibility that the adsorption mechanism cannot adsorb the medicine. When the medicine to be adsorbed cannot be adsorbed, the adsorption mechanism attempts to adsorb the medicine, for example, by repeating the adsorption operation (picking operation) for predetermined number of times. That is, in this case, the number of times of reattempting the medicine adsorption increases.

Thus, in this example, when it is determined that the medicine adsorption for a medicine to be adsorbed has failed, the conveyance control part 61 or the sorting control part 62 blows out air from the adsorption mechanism. It is possible to change the state of the medicine into the state different from the adsorption failure, for example, by laying down the standing medicine or changing the position of the medicine to a position away from the end portion. Therefore, the possibility of adsorbing the medicine can be increased, and thus, the number of times of reattempting the medicine adsorption.

Further, when it is determined that the adsorption of a medicine to be adsorbed has failed, the adsorption mechanism may blow out air for a predetermined number of times toward the medicine and the vicinity thereof. That is, the adsorption mechanism may blow out air for a predetermined number of times toward the same place.

For example, in this case, after the adsorption mechanism blows out air, the second camera 121 images the first accommodating part 11 or the like. This blowing operation and the imaging operation are repeated for a predetermined number of times, and an image captured by the second camera 121 is stored in the storage part 80 on all such occasions. The conveyance control part 61 or the sorting control part 62 specifies, with respect to the images captured for a plurality of times, an image change in the area where the adsorption mechanism blows air. Then, with respect to the images excluding the image of the housing such as the first accommodating part 11, the conveyance control part or the sorting control part determines whether or not an unchanged image exists in the images captured for a plurality of times. When a medicine exists in the area where the air has been blown, the position or posture of the medicine is somewhat changed by the blown air. Therefore, when the unchanged image exists in the images captured for a plurality of times, the conveyance control part 61 or the sorting control part 62 determines that such an image is the contamination adhered to the first accommodating part 11 or the like. Further, the presence/absence of a change in the images may be determined by using an image acquired by the second camera 121 when the medicine adsorption has failed.

In this manner, it is possible to determine whether or not the contamination is adhered to to the first accommodating part 11 or the like through a plurality of air blowing operations. Therefore, it is possible to notify the user of the fact that the contamination is adhered to the first accommodating part 11 or the like (that cleaning is necessary).

Further, a plurality of air blowing operations are not limited to when the medicine adsorption fails. For example, a plurality of air blowing operations may be performed in the state where no medicine is accommodated in the first accommodating part 11 or the like. In this case, by the above-described comparison of the images, an object, whose image is not changed, other than the medicine placement table 133a, may be determined as the contamination adhered to to the medicine placement table 133a.

Further, when fragments or powder dust of a medicine is accommodated in the medicine placement table 133a or the like, there is a possibility that the accuracy of medicine identification may decrease due to the fragments or the like. For example, depending upon the position or size of the fragments or the like, the fragment can be erroneously recognized as a medicine (or a portion thereof). In particular, in the medicine placement table 133a, the type of a medicine may be discriminated based on the captured image, but this discrimination may be affected depending upon the position or size of the fragments or the like.

Thus, in this example, the adsorption mechanism blows out air toward the medicine placement table 133a. This makes it possible to blow off the fragments or the like to the outside of the medicine placement table 133a. Further, it is possible to prevent the fragments or the like from being adhered to the medicine placement table 133a. For example, the adsorption mechanism performs the air blowing operation in the state where the medicine is not placed on the medicine placement table 133a (e.g., before placing the medicine on the medicine placement table 133a or after taking out the medicine from the medicine placement table 133a).

Further, the adsorption mechanism may also blow out air to the first accommodating part 11, the sorting cup 141, and the like, thus blowing off the fragments or the like or preventing the fragments or the like from being adhered. The adsorption mechanism may change the posture or position of the medicine and may blow off the fragments or the like by blowing out air, for example, when the adsorption mechanism fails to adsorb the medicine, as described above. Without being limited to this, the adsorption mechanism may perform the air blowing operation, for example, in the state where no medicine is accommodated in the first accommodating part 11 and the sorting cup 141.

(Adsorption Position Specifying Process)

Next, an adsorption position specifying process is described.

The conveyance control part 61 or the sorting control part 62 specifies the position of a medicine in the first accommodating part 11 or the sorting cup 141 by analyzing the image captured by the second camera 121. When the first accommodating part 11 has a hue (e.g., black color or gray color), the conveyance control part 61 specifies the position of the medicine from the difference between the hue of the first accommodating part 11 and the hue of the medicine in the image captured by, for example, the second camera 121. Even in case where the sorting cup 141 has a hue, the sorting control part 62 also performs the same process to specify the position of the medicine. However, there may be a possibility that the position of a medicine cannot be specified by this method when a medicine has a dark color (a medicine whose color is close to the hue of the first accommodating part 11 or the like) or when the medicine is transparent.

Figure 38:
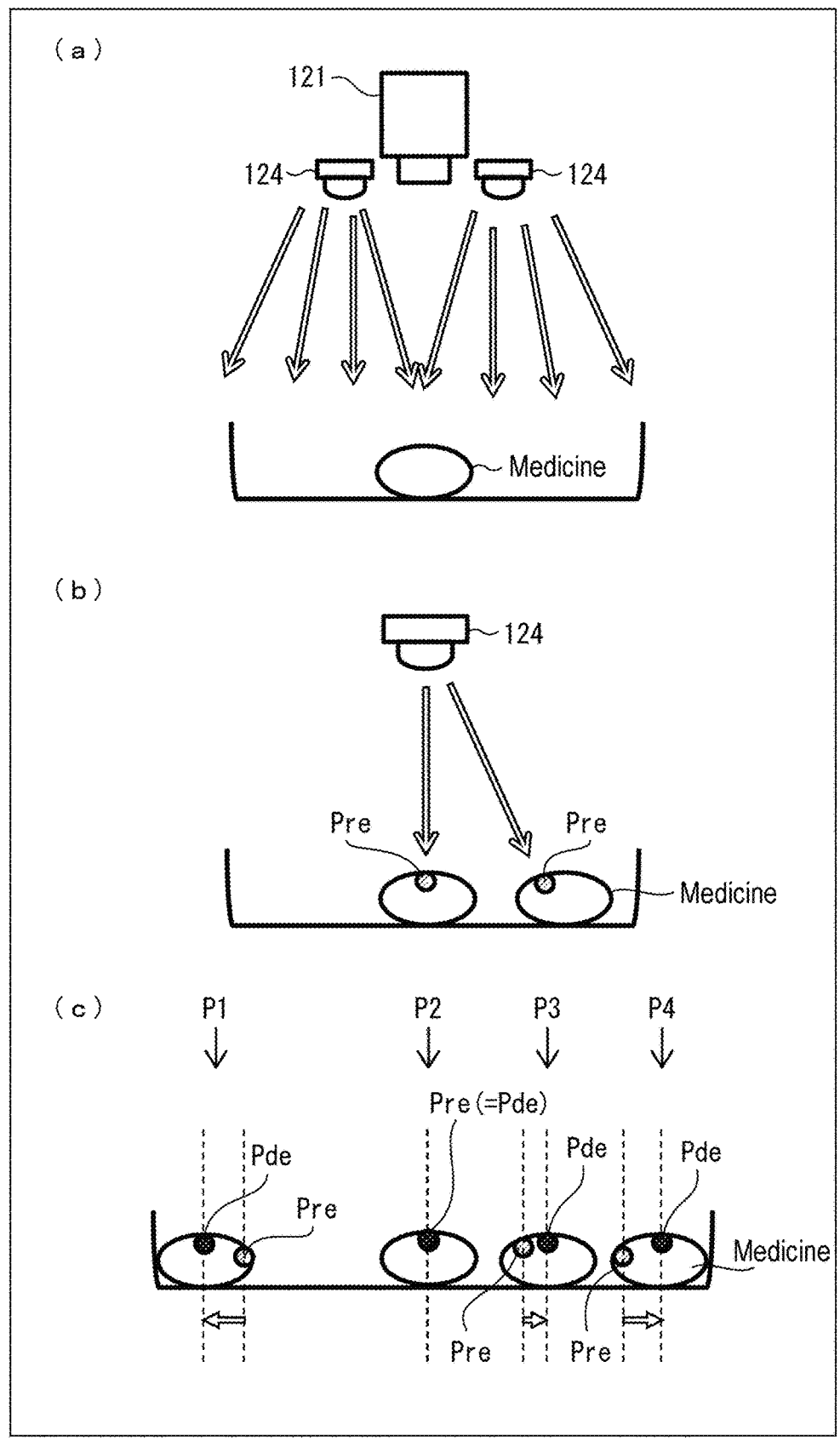
FIG. 38 ((a) to (c) of FIG. 38) is a view illustrating an example of an adsorption position specifying process.

Thus, in this example, the conveyance control part 61 or the sorting control part 62 specifies the position of a reflected light, which is radiated to a surface of the medicine and reflected by the surface, as the position of the medicine. In FIG. 38, (a) to (c) of FIG. 38 are views illustrating an example of an adsorption position specifying process.

As shown in (a) of FIG. 38, the conveyance/sorting unit 12 of this example includes a light source 124 that emits light when the second camera 121 captures an image. The light source 124 is provided in the vicinity of the second camera 121, and emits light toward the first accommodating part 11 or the sorting cup 141. This enables the second camera 121 to capture an image including an image of reflected light reflected by the surface of a medicine. Therefore, the conveyance control part 61 or the sorting control part 62 can specify the position of the reflected light included in the image captured by the second camera 121 as the position of the medicine.

In (a) of FIG. 38, the conveyance/sorting unit 12 includes two light sources 124. However, the number of the light sources 124 may be one or three or more as long as the position of a medicine can be specified in the image captured by the second camera 121.

Here, when two light sources 124 are considered as one light source, as shown in (b) of FIG. 38, the position of the reflected light in the medicine varies depending upon the position at which the medicine is placed. Specifically, when the position of the medicine is immediately below the light source 124, the position of the reflected light is at or near the center position of the medicine. Further, as the position of the medicine becomes away from immediately below the light source 124, the position of the reflected light becomes away from the center position of the medicine accordingly.

Thus, in this example, the conveyance control part 61 or the sorting control part 62 corrects the position of the reflected light on the medicine. The storage part 80 stores correction value information indicating a correction value (correction amount and direction) for correcting the position of the reflected light. Further, the correction value information is set through experiments or the like.

The correction value is associated with each position of a medicine (that is, each position of the reflected light) imaged in advance by changing the position of the medicine. As shown in (c) of FIG. 38, the correction value is set so as to increase as a distance increases from the position immediately below the light source 124. Specifically, in the medicines at positions P1, P3, and P4 that are deviated from immediately below the light source 124, the positions Pre of the reflected light are deviated from the center positions of the medicines. Therefore, the correction value is determined such that the position Pre of the reflected light becomes the center position of the medicine (detection position Pde for detecting the reflected light). Further, in the medicine at the position P2 immediately below the light source 124, the correction value is zero because the position Pre of the reflected light is the same as the center position of the medicine.

The conveyance control part 61 or the sorting control part 62 specifies the position Pre of the reflected light included in the image captured by the second camera 121, and then corrects the position Pre of the reflected light to the detection position Pde of the reflected light by referring to the correction value information. The conveyance control part 61 or the sorting control part 62 specifies the detection position Pde of the reflected light as the medicine adsorption position.

Therefore, even in the case where the first accommodating part 11 or the sorting cup 141 has a hue and a medicine has a hue close to the hue of the first accommodating part 11 or the sorting cup 141 or is transparent, it is possible to specify the medicine adsorption position with high accuracy. Further, since the accuracy of the adsorption position is required in the case where a medicine is particularly small, the above-described process makes it possible to determine the adsorption position with higher accuracy.

(Method of Determining Rotation Direction of First Camera)

Next, a method of determining the rotation direction of the first camera 131 is described.

It is assumed that the position of the first camera 131 at the time of imaging a medicine from above is set to 0°. Further, it is considered a case where a medicine (e.g., a capsule) is placed on the medicine placement table 133a in the state where information such as identification information given to the medicine is oriented in the direction of 315°. In this case, the imaging control part 63 may acquire information such as identification information (hereinafter, simply referred to as identification information) by analyzing the medicine imaged by the first camera 131 from the position of 315°.

Here, it is considered a case where the rotation mechanism 132 rotates the first camera 131 so as to turn around the disposition area Ar2 only in one direction (e.g., clockwise when viewed from the front of the medicine sorting device 1). When imaging the identification information of the medicine placed in the above state, the rotation mechanism 132 needs to move the first camera 131 to three positions of 45°, 135°, and 225°, and to move the first camera 131 to the position of 315° after the first camera 131 images the medicine. This is because it is difficult to acquire identification information even if images captured from the positions of 45°, 135°, and 225° are analyzed.

Thus, in this example, the rotation mechanism 132 rotates the first camera 131 so as to turn in any of the clockwise and counterclockwise directions around the disposition area Ar2. The imaging control part 63 controls the rotation mechanism 132 based on the image captured from the position of 0°, and determines the rotation direction of the first camera 131.

For example, the imaging control part 63 sets two areas on the medicine by bisecting the medicine in a direction parallel with the direction in which the shaft portion 133c extends (a direction perpendicular to the rotation direction of the first camera) in the image captured from the position of 0°. The imaging control part 63 specifies an area that includes at least a portion of the identification information given to the medicine among the two areas, and determines the direction in which the specified area exists as the rotation direction of the first camera 131. When the identification information is included in any of the two areas, the imaging control part 63 determines the direction in which the area having the larger area occupied by the identification information exists as the rotation direction of the first camera 131. Further, when the identification information is not included in the image obtained by imaging the medicine from the position of 0°, the imaging control part 63 rotates the first camera 131 in the initially set direction (e.g., clockwise).

This makes it possible to shorten the time spent until the identification information is acquired, and the time spent until the type of medicine is specified.

<Configuration Example of Medicine Sorting Device>

Figure 39:
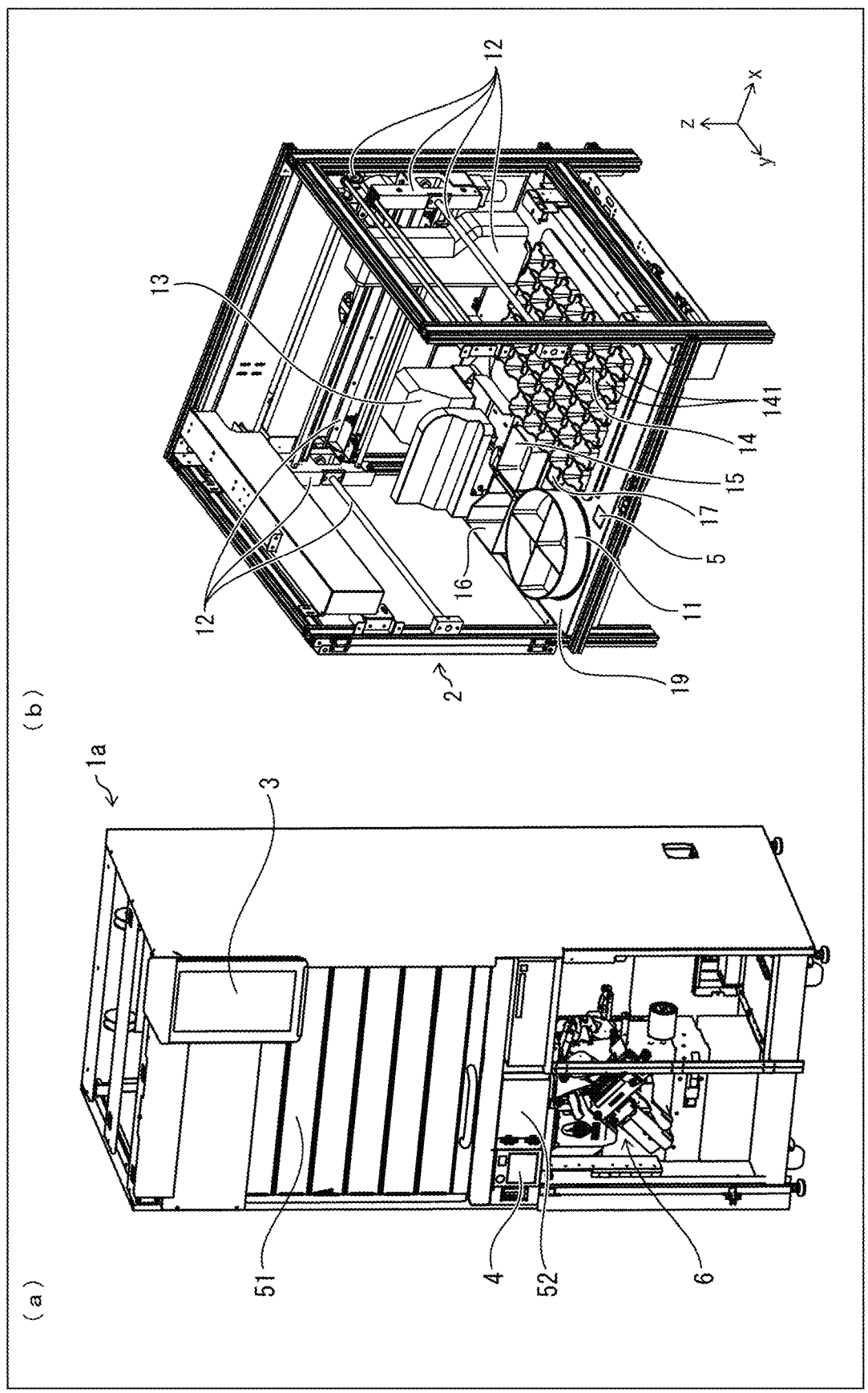
FIG. 39 is a view showing a further configuration example of a medicine sorting device, wherein (a) of FIG. 39 is a perspective view of the medicine sorting device and (b) of FIG. 39 is a perspective view showing a basic configuration of a medicine sorting area included in the medicine sorting device.

Next, a configuration example of a medicine sorting device 1a is described with reference to FIG. 39. FIG. 39 is a view showing a configuration example of the medicine sorting device 1a, wherein (a) of FIG. 39 is a perspective view of the medicine sorting device 1a and (b) of FIG. 39 is a perspective view showing a basic configuration of a medicine sorting area 2 included in the medicine sorting device 1a.

In the medicine sorting device 1 shown in FIG. 2, the first RFID reader/writer unit 5 is provided on a medicine take-out side (front side). However, as shown in (b) of FIG. 39, in the medicine sorting device 1a, the first RFID reader/writer unit 5 is provided on the medicine take-out side of the pedestal 19. Since the first RFID reader/writer unit 5 is provided on the pedestal 19, it is not necessary to take out a sorting cup 141 to the outside of the medicine sorting device 1a when reading information of the RFID tag of the sorting cup 141. Therefore, it is possible to reduce the possibility that the sorting cup 141 falls outside the medicine sorting device 1a and the medicines in the sorting cup 141 are scattered. That is, it is possible to improve operational safety.

Further, as the installation position of the first RFID reader/writer unit 5 is changed, in the medicine sorting device 1a, an opening/closing door 52 is provided on the medicine take-out side as shown in (a) of FIG. 39. To move a medicine accommodated in the second accommodating part 14 to the packaging mechanism 6, the medicine sorting device 1a includes, for example, a packaging hopper that temporarily holds the medicine, and a movement path for allowing the medicine held in the packaging hopper to move to the packaging mechanism 6. Further, at least the movement path is configured to be separable. By opening the opening/closing door 52, it is possible to take out the movement path to the outside of the medicine sorting device 1a.

That is, by providing the opening/closing door 52, it is possible to take out and clean the movement path. Further, it is possible to clean a member provided between the medicine inlet 17 and the packaging mechanism 6 (e.g., the packaging hopper) in the state where the movement path is separated.

Further, the medicine sorting device 1a includes an opening/closing shutter 51 that can open/close the medicine take-out side. The medicine sorting device 1 shown in FIG. 2 is also provided with an opening/closing, shutter similar to the opening/closing shutter 51 (FIG. 2 shows the opening/closing shutter to be substantially transparent such that the medicine sorting area 2 can be visually recognized).

[Supplementary Note]

The present invention is not limited to each of the above-described embodiments, and various modifications are possible within the scope indicated in the claims. Further, embodiments obtained by appropriately combining technical means disclosed in different embodiments are also included in the technical scope of the present invention.

DESCRIPTION OF REFERENCE SYMBOLS 1 medicine sorting device, 11 first accommodating part, 14 second accommodating part, 12 conveyance/sorting unit (sorting part), 61 conveyance control part (detection area changing part), 62 sorting control part (detection area changing part), 63 imaging control part, 64 discrimination part, 65 image classification part, 122 adsorption/shutter mechanism (adsorption mechanism), 131 first camera (imaging part), 132 rotation mechanism (rotation part), 133a medicine placement table, 133b turning mechanism (movement mechanism), 133c shaft portion, 134 illuminator (ultraviolet light radiation part, visible light radiation part), 134a first radiation part (visible light radiation part), 134b second radiation part (visible light radiation part), 134c ultraviolet light radiation part, 141, 141a to 141j sorting cup (sorting container), 142 opening, 143 side wall (outer wall), 145 edge portion, 146 convex portion, 146a adjoining portion, Ar1 receiving area (placement area, sorting standby area), Ar2 placement area, Dr detection area, Jo, Jo1, Jo2 journal, Im1 sorting image, Im2 inspection image

What is claimed is:

1. A medicine sorting device comprising:
a first accommodating part configured to accommodate a plurality of types of medicines in a mixed state;
a second accommodating part configured to accommodate the medicines in a state of being sorted by each type;
an imaging part configured to image the medicines;
a discrimination part configured to discriminate the types of the medicines based on images captured by the imaging part;
a sorting part configured to sort the medicines by each type based on a discrimination result performed by the discrimination part and to store the sorted medicines in the second accommodating part; and
an ultraviolet light radiation part configured to radiate ultraviolet light to the medicine to be imaged,
wherein the discrimination part performs discrimination by:
narrowing down candidates of medicine data related to a specific medicine from a medicine database, which manages medicine data related to the plurality of types of medicines, based on a first feature that is color data obtained from an image captured for the specific medicine in the state where the ultraviolet light is radiated; and
collating a second feature, which is different from the first feature and includes a logo of the specific medicine, obtained from an image captured for the specific medicine in a state where a visible light is radiated by the imaging part, with the narrowed-down candidates of medicine data.

2. The medicine sorting device of claim 1, further comprising a rotation part configured to rotate the imaging part such that the imaging part turns around a disposition area in which the medicine to be imaged is disposed,
   wherein the imaging part images the medicine disposed in the disposition area from a plurality of positions where the imaging part is rotated by the rotation part.

3. The medicine sorting device of claim 1, further comprising an image classification part configured to classify the image captured by the imaging part for each type of the medicine discriminated by the discrimination part.

4. The medicine sorting device of claim 1, wherein the determination part extracts a feature of the medicine from each of the images captured by the imaging part, and performs discrimination by collating the feature with the medicine database.

5. The medicine sorting device of claim 1, wherein the determination part extracts features of the medicine from each of the images captured by the imaging part, and performs discrimination in accordance with whether or not the features are the same by comparing the features with each other.

6. The medicine sorting device of claim 5, wherein, when the images of the medicines imaged by the imaging part are used as reference images, the discrimination part compares the features of the medicines in the images of the medicines, which are imaged by the imaging part after the reference images are acquired, with the features of the medicines in the reference images.

7. The medicine sorting device of claim 1, wherein, when medicine data related to the medicine is uniquely specified by a user's visual inspection, the medicine data is registered in the medicine database.

8. The medicine sorting device of claim 1, wherein, when the medicine whose type is discriminated corresponds to a sorting-unneeded medicine that does not need sorting, the discrimination part excludes the sorting-unneeded medicine from a sorting target.

9. A medicine sorting device comprising:
   a first accommodating part configured to accommodate a plurality of types of medicines in a mixed state;
   a second accommodating part configured to accommodate the medicines in a state of being sorted by each type;
   an imaging part configured to image the medicines;
   a discrimination part configured to discriminate the types of the medicines based on images captured by the imaging part;
   a sorting part configured to sort the medicines by each type based on a discrimination result performed by the discrimination part and to store the sorted medicines in the second accommodating part;
   an ultraviolet light radiation part configured to radiate ultraviolet light to the medicines to be imaged;
   a medicine placement table on which the medicine to be imaged is placed; and
   a movement mechanism configured to move the medicine placement table,
   wherein the discrimination part performs discrimination based on an imaging result of the medicine captured in the state where the ultraviolet light is radiated, and
   wherein the movement mechanism moves the medicine placement table from a placement area where the medicine is placed to a disposition area where the medicine is disposed such that the medicine is opposed to the imaging part, and moves the medicine placement table from the disposition area to a sorting standby area where the medicine placement table waits for sorting the medicine to the second accommodating part.

10. The medicine sorting device of claim 9, wherein two medicine placement tables are provided and each of the medicine placement tables is provided at an end portion of a shaft portion, and
   wherein, when one of the two medicine placement tables is disposed in the disposition area by turning the shaft portion, the movement mechanism disposes the other of the two medicine placement tables in the placement area or the sorting standby area.

11. A medicine sorting device comprising:
   a first accommodating part configured to accommodate a plurality of types of medicines in a mixed state;
   a second accommodating part configured to accommodate the medicines in a state of being sorted by each type;
   an imaging part configured to image the medicines;
   a discrimination part configured to discriminate the types of the medicines based on images captured by the imaging part; and
   a sorting part configured to sort the medicines b each type based on a discrimination result performed by the discrimination part and to store the sorted medicines in the second accommodating part,
   wherein the sorting part comprises:
   an adsorption mechanism that moves to the first accommodating part in a position opposed to the first accommodating part to adsorb the medicine accommodated in the first accommodating part; and
   a sensor that detects a suction force for adsorbing the medicine by the adsorption mechanism,
   wherein a first threshold value for determining whether or not the medicine exists in a vicinity of a tip portion of the adsorption mechanism and a second threshold value for determining that the medicine is adsorbed to the tip portion are set in the sensor.

12. The medicine sorting device of claim 11, wherein the discrimination part performs a recognition process on a plurality of characters given to a medicine included in an image captured by the imaging part, and
   wherein, among the plurality of characters recognized in the recognition process, the discrimination part determines characters, which are determined as having a size in a predetermined range and forming a string, as a plurality of characters actually formed in the medicine.

13. A medicine sorting device comprising:
   a first accommodating part configured to accommodate a plurality of types of medicines in a mixed state;
   a second accommodating part configured to accommodate the medicines in a state of being sorted by each type;
   an imaging part configured to image the medicines;
   a discrimination part configured to discriminate the types of the medicines based on images captured by the imaging part;
   a sorting part configured to sort the medicines by each type based on a discrimination result performed by the discrimination part and to store the sorted medicines in the second accommodating part;
   an ultraviolet light radiation part configured to radiate ultraviolet light to the medicines to be imaged;
   a rotation part configured to rotate the imaging part such that the imaging part turns around a disposition area in which the medicine to be imaged is disposed; and
   an imaging control part configured to control the imaging part,
   wherein the discrimination part performs discrimination by:
   narrowing down candidates of medicine data related to a specific medicine from a medicine database, which manages medicine data related to the plurality of types of medicines, based on a first feature of an image captured for the specific medicine in the state where the ultraviolet light is radiated; and collating a second feature, which is different from the first feature, of an image captured for the specific medicine by the imaging part, with the candidates of medicine data, wherein the imaging part images the medicine disposed in the disposition area from a plurality of positions where the imaging part is rotated by the rotation part, and wherein the imaging control part determines whether or not an imaging position of the imaging part is a predefined position by comparing a pattern of a predetermined portion other than a medicine, which is included in an image captured by the imaging part, with a predetermined pattern included in an image captured in advance by the imaging part.

14. The medicine sorting device of claim 13, further comprising a shaft portion that supports a medicine placement table which is disposed in the disposition area and on which the medicine to be imaged is placed, wherein, when the medicine placement table is disposed in the disposition area, the shaft portion is parallel with an axial direction about which the imaging part is rotated, and wherein the patterns of the predetermined portion are different in at least a portion in a circumferential direction of the shaft portion.

15. A medicine sorting device comprising:
a first accommodating part configured to accommodate a plurality of types of medicines in a mixed state;
a second accommodating part configured to accommodate the medicines in a state of being sorted by each type;
an imaging part configured to image the medicines;
a discrimination part configured to discriminate the types of the medicines based on images captured by the imaging part;
a sorting part configured to sort the medicines by each type based on a discrimination result performed by the discrimination part and to store the sorted medicines in the second accommodating part; and
an ultraviolet light radiation part configured to radiate ultraviolet light to the medicines to be imaged,
wherein the discrimination part performs discrimination by:
narrowing down candidates of medicine data related to a specific medicine from a medicine database, which manages medicine data related to the plurality of types of medicines, based on a first feature of an image captured for the specific medicine in the state where the ultraviolet light is radiated; and
collating a second feature, which is different from the first feature, of an image captured for the specific medicine by the imaging part, with the candidates of medicine data,
wherein the sorting part sorts a medicine, which is one of the medicines and is specified as a target to be taken out from the medicine sorting device based on return destination information related to a return destination of a sorted medicine, to a medicine take-out side in the medicine sorting device.

16. A medicine sorting device comprising:
a first accommodating part configured to accommodate a plurality of types of medicines in a mixed state;
a second accommodating part configured to accommodate the medicines in a state of being sorted by each type;
an imaging part configured to image the medicines;
a discrimination part configured to discriminate the types of the medicines based on images captured by the imaging part;
a sorting part configured to sort the medicines by each type based on a discrimination result performed by the discrimination part and to store the sorted medicines in the second accommodating part;
an ultraviolet light radiation part configured to radiate ultraviolet light to the medicines to be imaged;
a rotation part configured to rotate the imaging part such that the imaging part turns around a disposition area in which the medicine to be imaged is disposed; and
a medicine placement table on which the medicine to be imaged is placed,
wherein the discrimination part performs discrimination based on an imaging result of the medicine captured in the state where the ultraviolet light is radiated,
wherein the imaging part images the medicine disposed in the disposition area from a plurality of positions where the imaging part is rotated by the rotation part,
wherein the imaging part images the medicine from a first direction opposed to a placement surface of the medicine placement table on which the medicine is placed, or from a second direction opposite to the first direction, and
wherein the determination part determines whether or not the medicine is a tablet based on a shape of the medicine included in an image captured from the first direction or the second direction.

17. The medicine sorting device of claim 16, wherein, when the determination part cannot determine whether or not the medicine is a tablet based on the image captured from the first direction or the second direction, the imaging part images the medicine from an oblique direction with respect to the placement surface, and
wherein the determination part determines whether or not the medicine is a tablet based on the shape of the medicine included in the images captured from the first direction or the second direction and from the oblique direction.

18. A medicine sorting device comprising:
a first accommodating part configured to accommodate a plurality of types of medicines in a mixed state;
a second accommodating part configured to accommodate the medicines in a state of being sorted by each type;
an imagine part configured to image the medicines;
a discrimination part configured to discriminate the types of the medicines based on images captured by the imaging part;
a sorting part configured to sort the medicines by each type based on a discrimination result performed by the discrimination part and to store the sorted medicines in the second accommodating part; and
a detection area changing part,
wherein the detection area changing part changes a detection area for detecting the medicine accommodated in a sorting container which is disposed in the second accommodating part and accommodates the medicine sorted by the sorting part, in accordance with whether or not an image obtained by imaging the sorting container includes at least a portion of a bottom portion of the sorting container, or changes a detection area for detecting the medicine accommodated in the first accommodating part in accordance with whether or not an image obtained by imaging the first accommodating part includes at least a portion of a bottom portion of the first accommodating part.

19. The medicine sorting device of claim 18, wherein a plurality of pieces of medicine-specific information for specifying a medicine is assigned to each of the plurality of types of medicines,
- wherein, among the plurality of pieces of medicine-specific information, at least one medicine-specific information related to the medicine sorted by the sorting part is acquired from a return destination to which the sorted medicine is returned or a return assisting device for returning to the return destination, and
- wherein the at least one medicine-specific information is stored in an information recording medium provided in the sorting container that stores the sorted medicine, or the at least one piece of medicine-specific information is printed in a journal in which medicine data related to a medicine reflecting a user's visual inspection result is printed.

20. The medicine sorting device of claim 19, wherein a plurality of sorting containers that accommodate medicines sorted by the sorting part are disposed in the second accommodating part,
- wherein in regard to a medicine, which a user desires to sort into a predetermined sorting container of the plurality of sorting containers, among medicines included in a medicine database that manages medicine data related to the plurality of types of medicines, sorting identification information for sorting the medicine to the predetermined sorting container is given by a user input, and
- wherein the sorting part sorts the medicine, to which the sorting identification information is given, to the predetermined sorting container to which the sorting identification information is given.

* * * * *